US006841383B2

(12) United States Patent
Reff et al.

(10) Patent No.: US 6,841,383 B2
(45) Date of Patent: *Jan. 11, 2005

(54) METHOD FOR INTEGRATING GENES AT SPECIFIC SITES IN MAMMALIAN CELLS VIA HOMOLOGOUS RECOMBINATION AND VECTORS FOR ACCOMPLISHING THE SAME

(75) Inventors: Mitchell R. Reff, San Diego, CA (US); Richard Spence Barnett, San Marcos, CA (US); Karen Retta McLachlan, Solana Beach, CA (US)

(73) Assignee: Idec Pharmaceuticals Corporation, San Diego, CA (US)

( * ) Notice: Subject to any disclaimer, the term of this patent is extended or adjusted under 35 U.S.C. 154(b) by 154 days.

This patent is subject to a terminal disclaimer.

(21) Appl. No.: 10/109,853

(22) Filed: Apr. 1, 2002

(65) Prior Publication Data

US 2002/0192820 A1 Dec. 19, 2002

Related U.S. Application Data

(63) Continuation of application No. 09/343,485, filed on Jun. 30, 1999, now Pat. No. 6,413,777, which is a continuation of application No. 09/023,715, filed on Feb. 13, 1998, now Pat. No. 5,998,144, which is a continuation-in-part of application No. 08/819,866, filed on Mar. 14, 1997, now Pat. No. 5,830,698.

(51) Int. Cl.⁷ .............................. C12N 5/10; C12N 15/85

(52) U.S. Cl. ..................................... 435/325; 435/320.1

(58) Field of Search ............................... 435/325, 320.1

(56) References Cited

U.S. PATENT DOCUMENTS

| 5,202,238 | A | | 4/1993 | Fell et al. |
| 5,648,267 | A | | 7/1997 | Reff |
| 5,830,698 | A | * | 11/1998 | Reff et al. ................. 435/69.1 |
| 5,998,144 | A | * | 12/1999 | Reff et al. ...................... 435/6 |
| 6,413,777 | B1 | * | 7/2002 | Reff et al. .................. 435/463 |

OTHER PUBLICATIONS

Ramirez–Solis R et al., "Gene targeting in embryonic stem cells," *Methods in Enzymology*, 225:855–878.
Al–Shawi R, et al., "Expression of a foreign gene in a line of transgenic mice is modulated by a chromosomal position effect," *Mol Cell Biol*, 1990, 10: 1192–8.
Barnett RS, et al., "Antibody production in chinese hamster ovary cells using an impaired selectable marker," *ACS Symposium Series: Antibody Expression and Engineering*, 1997, 604: 27–40.
Capecchi MR, "Altering the genome by homologous recombination," *Science*, 1989, 244: 1288–92.
Choulika A, et al., "Induction of homologous recombination in mammalian chromosomes by using the I–ScI system of *Saccharomyces cerevisiae*," *Mol Cell Biol*, 1995, 15: 1968–73.

Dariavach P, et al., "Human Ig superfamily CTLA–4 gene: chromosomal localization and identity of protein sequence between murine and human CTLA–4 cytoplasmic domains," *Eur J Immunol*, 1988, 18: 1901–5.
Donahue TF, et al., "The nucleotide sequence of the HIS4 region of yeast," *Gene*, 1982, 18: 47–59.
Flesher AR, et al., "Fluorohore–labeled carbohydrate analysis of immunoglobulin fusion proteins: Correlation of oligosachharide content with in vivo clearance profile," *Biotechnology & Bioengineering*, 1995, 46: 399–407.
Fukushige S, et al., "Genomic targeting with a positive–selection Iox integration vector allows highly reproducible gene expression in mammalian cells," *Proc Natl Acad Sci U S A*, 1992, 89: 7905–9.
Linsley PS, et al., "CTLA–4 is a second receptor for the B cell activation antigen B7," *J Exp Med*, 1991, 174: 561–9.
Meinkoth J, et al., "Unstable and stable CAD gene amplification: importance of flanking sequences and nuclear environment in gene amplification," *Mol Cell Biol*, 1987, 7: 1415–24.
Morrow B, et al., "Gene targeting in mammalian cells by homologous recombination," *Curr Opin Biotechnol*, 1993, 4: 577–82.
Newman R, et al., ""Primatization" of recombinant antibodies for immunotherapy f human diseases: a macaque/human chimeric antibody against human CD4," *Biotechnology (N Y)*, 1992, 10: 1455–60.
Peakman TC, et al., "Comparison of expression of a humaniz d monoclonal antibody in mouse NSO myeloma cells and Chinese hamster ovary cells," *Hum Antibodies Hybridomas*, 1994, 5: 65–74.
Reff ME, "High–level production of recombinant immunoglobulins in mammalian cells," *Curr Opin Biotechnol*, 1993, 4: 573–6.
Reff ME, et al., "Depletion of B cells in vivo by a chimeric mouse human monoclonal antibody to CD20," *Blood*, 1994, 83: 435–45.
Rothstein R, "Targeting, disruption, replacement, and allele rescue: integrative DNA transformation in yeast," *Methods Enzymol*, 1991, 194: 281–301.

(List continued on next page.)

Primary Examiner—John S. Brusca
(74) Attorney, Agent, or Firm—Pillsbury Winthrop LLP

(57) ABSTRACT

A method for achieving site specific integration of a desired DNA at a target site in a mammalian cell via homologous recombination is described. This method provides for the reproducible selection of cell lines wherein a desired DNA is integrated at a predetermined transcriptionally active site previously marked with a marker plasmid. The method is particularly suitable for the production of mammalian cell lines which secrete mammalian proteins at high levels, in particular immunoglobulins. Novel vectors and vector combinations for use in the subject cloning method are also provided.

16 Claims, 75 Drawing Sheets

OTHER PUBLICATIONS

Sherlock S, et al., "Delta virus hepatitis," *J Hepatol,* 1986, 3: 419–23.

Sutton BJ, et al., "The human IgE network," *Nature,* 1993, 366: 421–8.

Thomas KR, et al., "High frequency targeting of genes to specific sites in the mammalian genome," *Cell,* 1986, 44: 419–28.

Urlaub G, et al., "Effect of gamma rays at the dihydrofolate reductase locus: deletions and inversions," *Somat Cell Mol Genet,* 1986, 12: 555–66.

Wahl GM, et al., "Gene amplification causes overproduction of the first three enzymes of UMP synthesis in N–(phosphonacetyl)–L–aspartate–resistant hamster cells," *J Biol Chem,* 1979, 254: 8679–89.

Yoshimura FK, et al., "Different activities of viral enhancer elements before and after stable integration of transfected DNAs," *Mol Cell Biol,* 1987, 7: 1296–9.

* cited by examiner

DESMOND

HD = Salmonella HisD Gene
N3 = Neomycin Phosphotransferase Exon 3
D = Murine Dihydrofolate reductase
E = Cytomegalovirus and SV40 Enhancers
SA = Splice acceptor
BT = Mouse Beta Globin Major Promoter
B = Bovine Growth Hormone Polyadenylation
S = SV40 Early Polyadenylation
SV = SV40 Late Polyadenylation Desmond
14,683 bp Bst1107 I linear

FIG. 2A
Molly

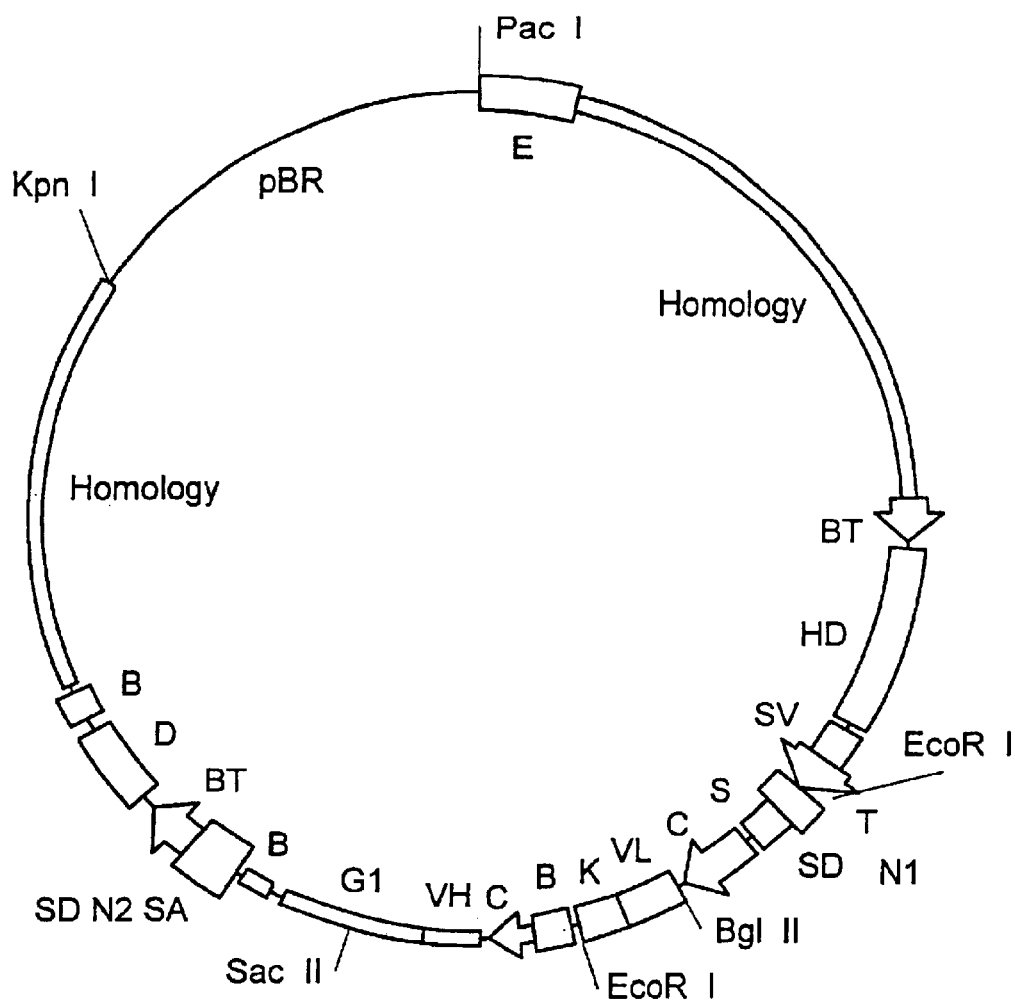

D = Dihydrofolate reductase
N1 + Neomycin Phosphotransferase Exon 1
N2 + Neomycin Phosphotransferase Exon 2
VL = Anti-CD20 Light chain leader + Variable
K = Human Kappa Constant
VH = Anti-CD20 Heavy chain Leader + Variable
G1 = Human Gamma 1 Constant
HD = Salmonella Histidinol Dehydrogenase
E = CMV and SV40 enhancers      S = SV40 Origin
SD = Splice donor               SA = Splice acceptor
C = CMV promoter/enhancer
T = HSV TK promoter and Poloma enhancers
BT = Mouse Beta Globin Major Promoter
SV = SV40 Late Polyadenylation
B = Bovine Growth Hormone Polyadenylation

Southern Analysis of Desmond Marked CHO Cells

FIG. 7A

```
TTTCTAGACC TAGGGCGGCC AGCTAGTAGC TTTGCTTCTC AATTTCTTAT TTGCATAATG    60
AGAAAAAAG  GAAAATTAAT TTTAACACCA ATTCAGTAGT TGATTGAGCA AATGCGTTGC   120
CAAAAGGAT  GCTTTAGAGA CAGTGTTCTC TGCACAGATA AGGACAAACA TTATTCAGAG   180
GGAGTACCCA GAGCTGAGAC TCCTAAGCCA GTGAGTGGCA CAGCATTCTA GGGAGAAATA   240
TGCTTGTCAT CACCGAAGCC TGATTCCGTA GAGCCACACC TTGGTAAGGG CCAATCTGCT   300
CACACAGGAT AGAGAGGGCA GGAGCCAGGG CAGAGCATAT AAGGTGAGGT AGGATCAGTT   360
GCTCCTCACA TTTGCTTCTG ACATAGTTGT GTTGGGAGCT TGGATAGCTT GGACAGCTCA   420
GGGCTGCGAT TTCGCGCCAA ACTTGACGGC AATCCTAGCG TGAAGGCTGG TAGGATTTTA   480
TCCCCGCTGC CATCATGGTT CGACCATTGA ACTGCATCGT CGCCGTGTCC CAAATATGG    540
GGATTGGCAA GAACGGAGAC CTACCCTGGC CTCCGCTCAG GAACGAGTTC AAGTACTTCC   600
AAAGAATGAC CACAACCTCT TCAGTGGAAG GTAAACAGAA TCTGGTGATT ATGGGTAGGA   660
```

FIG. 7B

```
AAACCTGGTT CTCCATTCCT GAGAAGAATC GACCTTTAAA GGACAGAATT AATATAGTTC
                                                                720
TCAGTAGAGA ACTCAAAGAA CCACCACGAG GAGCTCATTT TCTTGCCAAA AGTTTGGATG
                                                                780
ATGCCTTAAG ACTTATTGAA CAACCGGAAT TGGCAAGTAA AGTAGACATG GTTTGGATAG
                                                                840
TCGGAGGCAG TTCTGTTTAC CAGGAAGCCA TGAATCAACC AGGCCACCTT AGACTCTTTG
                                                                900
TGACAAGGAT CATGCAGGAA TTTGAAAGTG ACACGTTTTT CCCAGAAATT GATTGGGGA
                                                                960
AATATAAACT TCTCCCAGAA GTTTGAAGTC TACGAGAAGA AAGACTAACA GGAAAAGGCA
                                                                1020
TCAAGTATAA GTTTGAAGTC TACGAGAAGA AAGACTAACA GGAAGATGCT TTCAAGTTCT
                                                                1080
CTGCTCCCCT CCTAAAGCTA CTGTGCCTTC TAGTTGCCAG CCATCTGTTG GGACTTTTGC TGGCTTTAGA
                                                                1140
TCAGCCCTCGA CTGTGCCTTC TAGTTGCCAG CCATCTGTTG TTTGCCCCTC CCCGTGCCT
                                                                1200
TCCTTGACCC TGGAAGGTGC CACTCCCACT GTCCTTTCCT AATAAAATGA GGAAATTGCA
                                                                1260
TCGCATTGTC TGAGTAGGTG TCATTCT TT CTGGGGGGTG GGGTGGGGCA GGACAGCAAG
                                                                1320
```

FIG. 7C

```
GGGGAGGATT GGGAAGACAA TAGCAGGCAT GCTGGGGATG GCTGGGGCTC TATGGAACCA
                                                                    1380
GCTGGGGCTC GAAGCGGCCG CCCATTCGC TGGTGGTCAG ATGCGGGATG GCGTGGGACG
                                                                    1440
CGGCGGGGAC CGTCACACTG AGGTTTCCG CCAGACGCCA CTGCTGCCAG GCGCTGATGT
                                                                    1500
GCCCGGCTTC TGACCATGCG GTCGCGTTCG GGTAGTCGTG AGCCAGAGTT
                                                                    1560
GCCCGGGCGCT CTCCGGCTGC GGTAGTTCAG GCAGTTCAAT CAACTGTTTA CCTTGTGGAG
                                                                    1620
CGACATCCAG AGGCACTTCA CCGCTTGCTA GCGGCTTACC ATCCAGGGCC ACCATCCAGT
                                                                    1680
GCAGGAGCTC GTTATCGCTA TGACGGAACA GGTATTCGCT GGTCACTTCG ATGGTTTGCC
                                                                    1740
CGGATAAACG GAACTGGAAA AACTGCTGCT TACAGAACTG TTCCGTCAGC GCTGGATGCG
                                                                    1800
GCGTGCGGTC GGCAAAGACC AGACCGTTCA GACCACGGGT GCCGTTTTC ATCATATTTA ATCAGGACT
                                                                    1860
CAAAATCACC GCCGTAAGCC GACCACGGGT TGCCGTTTTC ATCATATTTA ATCAGGACT
                                                                    1920
GATCCACCCA GTCCCAGACG AAGCCCGGCCT GTAAACGGGG ATACTGACGA AACGCCTGCC
                                                                    1980
```

FIG. 7D

```
AGTATTTAGC GAAACCGCCA AGACTGTTAC CCATCGGCGTG GGCGTATTCG CAAAGGATCA
                                                                 2040
GCGGGCGCGT CTCTCCGGGT AGCGAAAGCC ATTTTTGAT GGACCATTTC GGACCAGCCG
                                                                 2100
GGAAGGGCTG GTCTTCATCC ACGGCGCGCGT ACATCGGGCA AATAATATCG GTGGCCGTGG
                                                                 2160
TGTCGGCTCC GCCGCCTTCA TACTGCACCG GGCGGGAAGG ATCGACAGAT TTGATCCAGC
                                                                 2220
GATACAGCGC GTCGTGATTA GCGCCGTGGC CTGATTCATT CCCCAGCGAC CAGATGATCA
                                                                 2280
CACTCGGGTG ATTACGATCG CGCTGCACCA TTCGCGTTAC GCGTTCGCTC ATCGCCGGTA
                                                                 2340
GCCAGCGCGG ATCATCGGTC AGACGATTCA TTGGCACCAT GCCGTGGGTT TCAATATTGG
                                                                 2400
CTTCATCCAC CACATACAGG CCGTAGCGGT CGCACAGCGT GTACCACAGC GGATGGTTCG
                                                                 2460
GATAATGCGA ACAGGCACG GCGTTAAAGT TGTTCTGCTT CATCAGCAGG ATATCCTGCA
                                                                 2520
CCATCGTCTG CTCATCCATG ACCTGACCAT GCAGAGGATG ATGCTCGTGA CGGTTAACGC
                                                                 2580
CTCGAATCAG CAACGGCTTG CCGTTCAGCA GCAGCAGACC ATTTCCAATC CGCACCTCGC
                                                                 2640
```

FIG. 7E

```
GGAAACCGAC ATCGCGAGGCT TCTGCTTCAA TCAGCGTGCC GTCGGCGGGTG TGCAGTTCAA
                                                                    2700
CCACCGCACG ATAGAGATTC GGGATTTCGG CGCTCCACAG TTTCGGGGTTT TCGACGTTCA
                                                                    2760
GACGCAGTGT GACGCGATCG GCATAACCAC CAGGCTCATC GATAATTTCA CCGCCGAAAG
                                                                    2820
GCGCGGGTGCC GCTGGGCGACC TGCGTTCAC CCTGCCATAA AGAAACTGTT ACCCGTAGGT
                                                                    2880
AGTCACGCAA CTCGCCGCAC ATCTGAACTT CAGCCTCCAG TACAGCGGCGG CTGAAATCAT
                                                                    2940
CATTAAAGCG AGTGGCAACA TGGAAATCGC TGATTTGTGT AGTCGGTTTA TGCAGCAACG
                                                                    3000
AGACGTCACG GAAAATGCCG CTCATCGCC ACATATCCTG ATCTTCCAGA TAACTGCCGT
                                                                    3060
CACTCCAACG CAGCACCATC ACCGGCGAGGC GGTTTCTCC GGCGCGTAAA AATGCGCTCA
                                                                    3120
GGTCAAATTC AGACGGGCAAA CGACTGTCCT GGCTGTAACC GACCCACGCC CCGTTGCACC
                                                                    3180
ACAGATGAAA CGCCGAGTTA ACGCCATCAA AAATAATTCG CGTCTGGCCT TCCTGTAGCC
                                                                    3240
AGCTTTCATC AACATTAAAT GTGAGCGAGT AACAACCCGT CGGATTCTCC GTGGGAACAA
                                                                    3300
```

FIG. 7F

```
ACGGCGGGATT GACCGTAATG GGATAGGTTA CGTTGGTGTA GATGGGGGCA TCGTAACCGT
                                                                3360
GCATCTGCCA GTTGAGGGG ACGACGACAG TATCGGCCTC AGGAAGATCG CACTCCAGCC
                                                                3420
AGCTTTCCGG CACTGCTTCT GGTGCCGGAA ACCAGGCAAA GCGCCATTCG CCATTCAGGC
                                                                3480
TGCGCAACTG TTGGGAAGGG CGATCGGTGC GGGCCTCTTC GCTATTACGC CAGCTGGCGA
                                                                3540
AAGCGGGGATG TGCTGCAAGG CGATTAAGTT GGGTAACGCC AGGGTTTTCC CAGTCACGAC
                                                                3600
GTTGTAAAAC GACTTAATCC GTCGAGGGGC TGCCTCGAAG CAGACGACCT TCCGTTGTGC
                                                                3660
AGCCAGCGGC GCCTGCGCCG GTGCCCACAA TCGTGCCGCGA ACAAACTAAA CCAGAACAAA
                                                                3720
TCATACCGGC GGCACGACCG CCACCACCTT CTCCTGTGCC TAACATTCCA GCGCCTCCAC
                                                                3780
CACTACCACC ACCATCGATG TCTGAATTGC CGCCCGCTCC ACCAATGCCG ACGGAACCTC
                                                                3840
AACCCGCTGC ACCTTTAGAC GACAGACAAC AATTGTTGGA AGCTATTAGA AACGAAAAAA
                                                                3900
ATCGGCACTCG TCTCAGACCG GCTCTCTTAA GGTAGCTCAA ACCAAAAACG GCGCCCGAAA
                                                                3960
```

FIG. 7G

```
CCAGTACAAT AGTTGAGGTG CCGACTGTGT TGCCTAAAGA GACATTTGAG CTTAAACCGC
                                                                4020
CGTCTGCACC ACCGCCACCA CCTCCGCCTC CGCCTCCGCC GCCAGCCCCG CCTGCCCTC
                                                                4080
CACCGATGGT AGATTCATCA TCAGCTCCAC CACCGCCGCC ATTAGTAGAT TTGCCGTCTG
                                                                4140
AAATGTTACC ACCGCCTGCA CCATCGCTTT CTAACGTGTT GTCTGAATTA AAATCGGGCA
                                                                4200
CAGTTAGATT GAAACCCGCC CAAAAACGCC CGCAATCAGA AATAATTCCA AAAAGCTCAA
                                                                4260
CTACAAATTT GATCGCGGAC GTGTTAGCCG ACACAATTAA TAGGCGTCGT GTGGCTATGG
                                                                4320
CAAAATCGTC TTCGGAAGCA ACTTCTAACG ACGAGGGTTG GGACGACGAC GATAATCGGC
                                                                4380
CTAATAAAGC TAACACGCCC GATGTTAAAT ATGTCCAAGC TACTAGTGGT ACCTTAATTA
                                                                4440
AGGGGCGGAG AATGGGGCGGA ACTGGGGCGGA GTTAGGGGCG GGATGGGGCCG AGTTAGGGAG
                                                                4500
GGGACTATGG TTGCTGACTA ATTGAGATGC ATGCTTTGCA TACTTCTGCC TGCTGGGGAG
                                                                4560
CCTGGGGACT TTCCACACCT GGTTGCTGAC TAATTGAGAT GCATGCTTTG CATACTTCTG
                                                                4620
```

FIG. 7H

```
CCTGCTGGGG AGCCTGGGGA CTTTCCACAC CCTAACTGAC ACACATTCCA CAGAATTAAT
                                                                4680
TCCCCTAGTT ATTAATAGTA ATCAATTACG GGGTCATTAG TTCATAGCCC ATATATGGAG
                                                                4740
TTCCGCGTTA CATAACTTAC GGTAAATGGC CCGCCTGGCT GACCGCTCAA CGACCCCGC
                                                                4800
CCATTGACGT CAATAATGAC GTATGTTCCC ATAGTAACGC CAATAGGGAC TTTCCATTGA
                                                                4860
CGTCAATGGG TGGACTATTT ACGGTAAACT GCCCACTTGG CAGTACATCA AGTGTATCAT
                                                                4920
ATGCCAAGTA CGCCCCCTAT TGACGTCAAT GACGGTAAAT GGCCCGCCTG GCATTATGCC
                                                                4980
CAGTACATGA CCTTATGGGA CTTTCCTACT TGGCAGTACA TCTACGTATT AGTCATCGCT
                                                                5040
ATTACCATGG TGATGCGGTT TTGGCAGTAC ATCAATGGGC GTGGATAGCG GTTTGACTCA
                                                                5100
CGGGGATTTC CAAGTCTCCA CCCCATTGAC GTCAATGGGA GTTTGTTTTG AAGCTTGGCC
                                                                5160
GGCCATATAA ACGGGCGGCA GCTTTATTTA ACGTGTTTAC GTCGAGTCAA TTGTACACTA
                                                                5220
ACGACAGTGA TGAAAGAAAT ACAAAAGCGC ATAATATTTT GAACGACGTC GAACCTTTAT
                                                                5280
```

FIG. 7I

| | | | | |
|---|---|---|---|---|
| TACAAAACAA | AACACAAACG | AATATCGACA | AAGCTAGATT | GCTGCTACAA | GATTGGCAA 5340 |
| GTTTGTGGC | GTTGAGCGAA | AATCCATTAG | ATAGTCCAGC | CATCGGTTCG | GAAAAACAAC 5400 |
| CCTGTTTGA | AACTAATCGA | AACCTATTTT | ACAAATCTAT | TGAGGATTTA | ATATTTAAAT 5460 |
| TCAGATATAA | AGACGCTGAA | AATCATTTGA | TTTTCGCTCT | AACATACCAC | CCTAAAGATT 5520 |
| ATAAATTTAA | TGAATTATTA | AAATACATCA | GCAACTATAT | ATTGATAGAC | ATTTCCAGTT 5580 |
| TGTGATATTA | GTTTGTGCGT | CTCATTACAA | TGGCTGTTAT | TTTTAACAAC | AAACAACTGC 5640 |
| TCGCAGACAA | TAGTATAGAA | AAGGGAGGTG | AACTGTTTTT | GTTAACGGT | TCGTACAACA 5700 |
| TTTTGGAAAG | TTATGTTAAT | CCGGTGCTGC | TAAAAAATGG | TGTAATTGAA | CTAGAAGAAG 5760 |
| CTGCGTACTA | TGCCGGCAAC | ATATTGTACA | AAACCGACGA | TCCCAAATTC | ATTGATTATA 5820 |
| TAAATTTAAT | AATTAAAGCA | ACACACTCCG | AAGAACTACC | AGAAAATAGC | ACTGTTGTAA 5880 |
| ATTACAGAAA | AACTATGCGC | AGCGGTACTA | TACACCCCAT | TAAAAAAGAC | ATATATATTT 5940 |

FIG. 7J

```
ATGACAACAA AAAATTTACT CTATACGATA GATACATATA TGGATACGAT AATAACTATG
                                                                6000
TTAATTTTTA TGAGGAGAAA AATGAAAAAG AGAAGGAATA CGAAGAAGAA GACGACAAGG
                                                                6060
CGTCTAGTTT ATGTGAAAAT AAAATTATAT TGTCGCAAAT TAACTGTGAA TCATTTGAAA
                                                                6120
ATGATTTTAA ATATTACCTC AGCGATTATA ACTACGCGTT TTCAATTATA GATAACACTA
                                                                6180
CAAATGTTCT TGTTGCGTTT GGTTGTATC GTTAATAAAA AACAAATTTA GCATTATAA
                                                                6240
TTGTTTTATT ATTCAATAAT TACAAATAGG ATTGAGACCC TTGCAGTTGC CAGCAAACGG
                                                                6300
ACAGAGCTTG TCGAGGAGAG TTGTTGATTC ATGTTTGCC TCCCTGCTGC GGTTTTTGAC
                                                                6360
CGAAGTTCAT GCCAGTCCAG GCAGAAAAGC CGCCGACTTC CGTTGCGGGT
                                                                6420
CGGCGAGTGAA GATCCCTTTC TTGTTACCGC CAACGCGCAA TATGCCTTGC GAGGTCGCAA
                                                                6480
AATCGGGCGAA ATTCCATACC TGTTCACCGA CGACGGCGCT GACGCGCGGT AAGACGCGGT
                                                                6540
GATACATATC CAGCCATGCA CACTGATACT CTTCACTCCA CATGTCGGTG TACATTGAGT
                                                                6600
```

FIG. 7K

```
GCAGCCCGGC TAACGTATCC ACGCCGTATT CGGTGATGAT AATCGGCTGA TGCAGTTTCT   6660
CCTGCCAGGC CAGAAGTTCT TTTTCCAGTA CCTTCTCTGC CGTTCCAAA TCGCCGCTTT    6720
GGACATACCA TCCGTAATAA CGGTTCAGGC ACAGCACATC AAAGAGATCG CTGATGGTAT   6780
CGGTGTGAGC GTCGCAGAAC ATTACATTGA CGCAGGTGAT CGGACGCGTC GGGTCGAGTT   6840
TACGCGTTGC TTCCGCCAGT GGCGCGAAAT ATTCCCGTGC ACCTTGCGGA CGGGTATCCG   6900
GTTCGTTGGC AATACTCCAC ATCACCACGC TTGGGTGGTT TTTGTCACGC GCTATCAGCT   6960
CTTTAATCGC CTGTAAGTGC GCTTGGGTGAG CTTCGAAAC GACTGCCTCT TCGTTGTACA   7020
GTTCTTTCGG CTGTTGCCC GCTTCGAAAC CAATGCCTAA AGAGAGGTTA AAGCCGACAG    7080
CAGCAGTTTC ATCAATCACC ACGATGCCAT GTTCATCTGC CCAGTCGAGC ATCTCTTCAG   7140
CGTAAGGGTA ATGCGAGGTA CGGTAGGAGT TGGCCCTAAT CCAGTCCATT AATGCGTGGT   7200
CGTGCCACCAT CAGCACGTTA TCGAATGCTT TGCCACGCAA GTCCGGCATCT TCATGACGAC  7260
```

FIG. 7L

```
CAAAGCCAGT AAAGTAGAAC GGTTGTGGT TAATCAGGAA CTGTTCGCCC TTCACTGCCA
                                                                7320
CTGACCGGAT GCCGACGCGA AGCGGGTAGA TATCACACTC TGTCTGGCTT TTGGCTGTGA
                                                                7380
CGCACAGTTC ATAGAGATAA CCTTCACCCG GTTGCCAGAG GTGCGGATTC ACCACTTGCA
                                                                7440
AAGTCCCGCT AGTGCCTTGT CCAGTTGCAA CCACCTGTTG ATCCGCATCA CGCAGTTCAA
                                                                7500
CGCTGACATC ACCATTGGCC ACCACCTGCC AGTCAACAGA CGCGTGGTTA CAGTCTTGCG
                                                                7560
CGACATGCGT CACTACGGTG ATATCGTCCA CCCAGGTGTT CGGCGTGGTG TAGAGCATTA
                                                                7620
CGCTGGATG GATTCCGGCA TAGTTAAAGA AATCATGGAA GTAAGATTGC TTTTCTTGC
                                                                7680
CGTTTTCGTT GGTAATCACC ATTCCCGGCG GGATAGTCTG CCAGTTCAGT TCGTTGTTCA
                                                                7740
CACAAACGGT GATACCCCTC GACGGATTAA AGACTTCAAG CGGTCAACTA TGAAGAAGTG
                                                                7800
TTCGTCTTCG TCCCAGTAAG CTATGTGTCT AGAATGTAGC CATCCATCCT TGTCAATCAA
                                                                7860
GGCGTTGGTC GCTTCCGGAT TGTTTACATA ACCGGACATA ATCATAGGTC CTCTGACACA
                                                                7920
```

FIG. 7M

```
TAATACGCCT CTCTGATTAA CGCCCAGCGT TTTCCCGGTA TCCAGATCCA CAACCTTCGC
                                                              7980
TTCAAAAAAT GGAACAACTT TACCGACCGC GCCCGGTTTA TCATCCCCCT CGGGTGTAAT
                                                              8040
CAGAATAGCT GATGTAGTCT CAGTGAGCCC ATATCCTTGT CGTATCCCTG GAAGATGGAA
                                                              8100
GCGTTTTGCA ACCGGCTTCCC CGACTCTCTT CGAAAGAGGT GCGCCCCCAG AAGCAATTTC
                                                              8160
GTGTAAATTA GATAAATCGT ATTTGTCAAT CAGAGTGCTT TTGGCGAAGA ATGAAAATAG
                                                              8220
GGTTGGTACT AGCAACGCAC TTTGAATTTT GTAATCCTGA AGGGATCGTA AAACAGCTC
                                                              8280
TTCTTCAAAT CTATACATTA AGACGACTCG AAATCTACAT ATCAAATATC CGAGTGTAGT
                                                              8340
AAACATTCCA AAACCGTGAT GGAATGGAAC AACACTTAAA ATCGCAGTAT CCGGAATGAT
                                                              8400
TTGATTGCCA AAATATAGGA CTCTGGCATG CGAGAATCTA GCGCAGGCAG TTCTATGCGG
                                                              8460
AAGGGCCACA CCCTTAGGTA ACCCAGTAGA TCCAGAGGAA TTGTTTTGTC ACGATCAAAG
                                                              8520
GACTCTGGTA CAAAATCGTA TTCATTAAAA CCGGGAGGTA GATGAGATGT GACGAAGGTG
                                                              8580
```

FIG. 7N

```
TACATCGACT GAAATCCCTG GTAATCCGTT TTAGAATCCA TGATAATAAT TTTCTGGATT
                                                                8640
ATTGGTAATT TTTTTGCAC GTTCAAAATT TTTTGCAACC CCTTTTTGGA AACAAACACT
                                                                8700
ACGGTAGGCT GCGAAATGTT CATACTGTTG AGCAATTCAC GTTCATTATA AATGTCGTTC
                                                                8760
GCGGGCGCAA CTGCAACTCC GATAAATAAC GCGCCCAACA CCGGCATAAA GAATTGAAGA
                                                                8820
GAGTTTTCAC TGCATACGAC GATTCTGTGA TTTGTATTCA GCCCATATCG TTTCATAGCT
                                                                8880
TCTGCCAACC GAACGGACAT TTCGAAGTAT TCCGCGTACG TGATGTTCAC CTCGATATGT
                                                                8940
GCATCTGTAA AAGGAATTGT TCCAGGAACC AGGGCGTATC TCTTCATAGC CTTATGCAGT
                                                                9000
TGCTCTCCAG CGGTTCCATT CTCTAGCTTT GCTTCTCAAT TTCTTATTTG CATAATGAGA
                                                                9060
AAAAAAGGAA AATTAATTTT AACACCAATT CAGTAGTTGA TTGAGCAAAT GCGTTGCCAA
                                                                9120
AAAGGATGCT TTAGAGACAG TGTTCTCTGC ACAGATAAGG ACAAACATCA TTCAGAGGGA
                                                                9180
GTACCCAGAG CTGAGACTCC TAAGCCAGTG AGTGGCACAG CATTCTAGGG AGAAATATGC
                                                                9240
```

FIG. 7P

```
TTGTCATCAC CGAAGCCTGA TTCCGTAGAG CCACACCTTG GTAAGGGCCA ATCTGCTCAC
                                                                9300
ACAGGATAGA GAGGGCAGGA GCCAGGGCAG AGCATATAAG GTGAGGTAGG ATCAGTTGCT
                                                                9360
CCTCACATTT GCTTCTGACA TAGTTGTGTT GGGAGCTTGG ATCGATCCAC CATGGGCTTC
                                                                9420
AATACCCTGA TTGACTGGAA CAGCTGTAGC CCTGAACAGC AGCGTGCGCT GCTGACGCGT
                                                                9480
CCGGCGATTT CCGCCTCTGA CAGTATTACC CGGACGGTCA GCGATATTCT GGATAATGCA
                                                                9540
AAAACGGCCG GTGACGATGC CCTGCGTGAA TACAGCGGCTA AATTGATAA AACAGAAGTG
                                                                9600
ACAGCGGCTAC GCGTCACCCC TGAAGAGATC GCCGCCGCCG GCGCGCGTCT GAGCGACGAA
                                                                9660
TTAAAACAGG CGATGACCGC TGCCGTCAAA AATATTGAAA CGTTCCATTC CGGCAGACG
                                                                9720
CTACCGCTTG TAGATGTGGA AACCCAGCCA GGCGTGCCGTT GCCAGCAGGT TACGCGTCCC
                                                                9780
GTCTCGTCTG TCGGTCTGTA TATTCCCGGC GGCTCGGCTC CGCTCTTCTC AACGGTGCTG
                                                                9840
ATGCTGGCGA CGCCGGCGCG CATTGCGGGA TGCTAGAAGG TGGTTCTGTG CTCGCCGCCG
                                                                9900
```

FIG. 7Q

```
CCCATCGCTG ATGAAATCCT CTATGCGGGCG CAACTGTGTG GCGTGCAGGA ATTCTTTAAC
                                                                    9960
CTCGGGGGCG CGCAGGGGAT TGCCGCTCTG GCCTTCGGCA GCGAGTCCGT ACCGAAAGTG
                                                                   10020
GATAAAATTT TTGGCCCCGG CAACGCCTTT GTAACCGAAG CCAAACGTCA GGTCAGCCAG
                                                                   10080
CGTCTCGACG GCGCGGGCTAT CGATATGCCA GCCGAGCCGT CTGAAGTACT GGTGATCGCA
                                                                   10140
GACAGCGGGCG CAACACCGGA TTTCGTCGCT TCTCCCAGAC TGAGCACGGC
                                                                   10200
CCGGATTCCC AGGTGATCCT GCTGACGCCT GATGCTGACA TTGCCCGCAA GGTGCGGGAG
                                                                   10260
GCGGTAGAAC GTCAACTGGC GGAACTGCCG CGGGGGACA CCGCCTGGCA GGCCCTGAGC
                                                                   10320
GCCAGTCGTC TGATTGTGAC CAAAGATTTA GCGCAGTGCG TCGCCATCTC TAATCAGTAT
                                                                   10380
GGGCCGGAAC ACTTAATCAT CCAGACGCGC AATGCCGCGCG ATTTGGTGGA TGCGATTACC
                                                                   10440
AGCGCAGGCT CGGTATTTCT CGGCGACTGG TCGCCGGAAT CCGCCGGTGA TTACGCTTCC
                                                                   10500
GGAACCAACC ATGTTTTACC GACCTATGGC CATACTGCTA CCTGTTCCAG CCTTGGGTTA
                                                                   10560
```

FIG. 7R

```
GCGGGATTTCC AGAAACGGAT GACCGTTCAG GAACTGTCGA AAGCGGGCTT TTCCGCTCTG
                                                                10620
GCATCAACCA TTGAAACATT GGCGGGGGCA GAACGTCTGA CCGCCCATAA AAATGCCGTG
                                                                10680
ACCCTGCGCG TAAACGCCCT CAAGGAGCAA GCATGAGCAC TGAAAACACT CTCAGCGTCG
                                                                10740
CTGACTTAGC CCGTGAAAAT GTCCGCAACC TGGAGATCCA GACATGATAA GATACATTGA
                                                                10800
TGAGTTTGGA CAAACCACAA CTAGAATGCA GTGAAAAAAA TGCTTTATTT GTGAAATTTG
                                                                10860
TGATGCTATT GCTTTATTTG TAACCATTAT AAGCTGCAAT AAACAAGTTA ACAACAACAA
                                                                10920
TTGCATTCAT TTTATGTTTC AGGTTCAGGG GGAGGTGTGG GAGGTTTTTT AAAGCAAGTA
                                                                10980
AAACCTCTAC AAATGTGGTA TGGCTGATTA TGATCTCTAG TCAGGCTCAA GGCCTGGCCG
                                                                11040
CTACTAACTC TCTCCTCCCT CCTTTTTCCT GCAGGCTCAA GGCGGATGCC CCGACGGCG
                                                                11100
AGGATCTCGT CGTGACCCAT GGCGATGCCT GCTTGCCGAA TATCATGGTG GAAAATGGCC
                                                                11160
GCTTTTCTGG ATTCATCGAC TGTGGCCGGC TGGGTGTGGC GGACCGCTAT CAGGACATAG
                                                                11220
```

FIG. 7S

```
CGTTGGCTAC CCGTGATATT GCTGAAGAGC TTGGCGGGCGA ATGGGCTGAC CGCTTCCTCG    11280
TGCTTTACGG TATCGCCCGCT CCCGATTCGC AGCGCATCGC CTTCTATCGC CTTCTTGACG    11340
AGTTCTTCTG AGCGGGACTC TGGGGTTCGA AATGACCGAC CAAGCGACGC CCAACCTGCC    11400
ATCACGAGAT TTCGATTCCA CCGCCGCCTT CTATGAAAGG TTGGGCTTCG GAATCGTTTT    11460
CCGGGACGCC GGCTGGATGA TCCTCCAGCG CGGGGATCTC ATGCTGGAGT TCTTCGCCCA    11520
CCCCAACTTG TTTATTGCAG CTTATAATGG TTACAAATAA AGCAATAGCA TCACAAATTT    11580
CACAAATAAA GCATTTTTT CACTGCATTC TAGTTGTGGT TTGTCCAAAC TCATCAATCT    11640
ATCTTATCAT GTCTGGATCG CGGCCGGGTCT CTCTCTAGCC CTAGGTCTAG ACTTGGCAGA    11700
ACATATCCAT CGGCGTCCGCC ATCTCCAGCA GCCGCACGCG GCGCATCTCG GGCAGCGTTG    11760
GGTCCTGGCC ACGGGTGCGC ATGATCGTGC TCCTGTCGTT GAGGACCCGG CTAGGCTGGC    11820
GGGGTTGCCT TACTGGTTAG CAGAATGAAT CACCGATACG CGAGCGAACG TGAAGCGACT    11880
```

FIG. 7T

```
GCTGCTGCAA AACGTCTGCG ACCTGACCAA CAACATGAAT GGTCTTCGGT TTCCGTGTTT   11940
CGTAAAGTCT GGAAACGCGG AAGTCAGCGC CCTGCACCAT TATGTTCCGG ATCTGCATCG   12000
CAGGATGCTG CTGGCTACCC TGTGGAACAC CTACATCTGT ATTAACGAAG CGCTGGCATT   12060
GACCCTGAGT GATTTTTCTC TGGTCCCGCC GCATCCATAC CGCCAGTTGT TTACCCTCAC   12120
AACGTTCCAG TAACCGGGCA TGTTCATCAT CAGTAACCCG TATCGTGAGC ATCCTCTCTC   12180
GTTTCATCGG TATCATTACC CCCATGAACA GAAATCCCCC TTACACGGAG GCATCAGTGA   12240
CCAAACAGGA AAAACCGGCC CTAAACATGG CCCGCTTTAT CAGAAGCCAG ACATTAACGC   12300
TTCTGGAGAA ACTCAACGAG CTGGACGCGG ATGAACAGGC AGACATCTGT GAATCGCTTC   12360
ACGACCACGC TGATGAGCTT TACCGCAGCT GCCTCGGCGCG TTTCGGTGAT GACGGTGAAA   12420
ACCTCTGACA CATGCAGCTC CCGGAGACGG TCACAGCTTG TCTGTAAGCG GATGCCGGGA   12480
GCAGACAAGC CCGTCAGGGC GCGTCAGCGG GTGTTGGCGG GTGTCGGGGC GCAGCCATGA   12540
```

FIG. 7U

```
CCCAGTCACG TAGCGATAGC GGAGTGTATA CTGGCTTAAC TATGCGGGCAT CAGAGCAGAT    12600
TGTACTGAGA GTGCACCATA TGCGGGTGTGA AATACCGCAC AGATGCGTAA GGAGAAATA     12660
CCGCATCAGG CGCTCTTCCG CTTCCTCGCT CACTGACTCG CTGCGCTCGG TCGTTCGGCT     12720
GCGGCGAGCG GTATCAGCTC ACTCAAAGGC GGTAATACGG TTATCCACAG AATCAGGGGA     12780
TAACGCAGGA AAGAACATGT GAGCAAAAGG CCAGCAAAAG GCCAGGAACC GTAAAAAGGC     12840
CGCGTTGCTG GCGTTTTTCC ATAGGCTCCG CCCCCCTGAC GAGCATCACA AAAATCGACG     12900
CTCAAGTCAG AGGTGGCGAA ACCCGACAGG ACTATAAAGA TACCAGGCGT TTCCCCTGG     12960
AAGCTCCCTC GTGCGCTCTC CTGTTCCGAC CCTGCCGCTT ACCGGATACC TGTCCGCCTT    13020
TCTCCCTTCG GGAAGCGTGG CGCTTTCTCA TAGCTCACGC TGTAGGTATC TCAGTTCGGT    13080
GTAGGTCGTT CGCTCCAAGC TGGGCTGTGT GCACGAACCC CCGTTCAGC CCGACCGCTG     13140
CGCCTTATCC GGTAACTATC GTCTTGAGTC CAACCCGGTA AGACACGACT TATCGCCACT    13200
```

FIG. 7V

```
GGCAGCAGCC ACTGGTAACA GGATTAGCAG AGCGAGGTAT GTAGGCGGTG CTACAGAGTT
                                                              13260
CTTGAAGTGG TGGCCTAACT ACGGCTACAC TAGAAGGACA GTATTTGGTA TCTGCGCTCT
                                                              13320
GCTGAAGCCA GTTACCTTCG GAAAAAGAGT TGGTAGCTCT TGATCCGGCA AACAAACCAC
                                                              13380
CGCTGGTAGC GGTGGTTTTT TTGTTTGCAA GCAGCAGATT ACGCGCAGAA AAAAGGATC
                                                              13440
TCAAGAAGAT CCTTTGATCT TTTCTACGGG GTCTGACGCT CAGTGGAACG AAAACTCACG
                                                              13500
TTAAGGGATT TTGGTCATGA GATTATCAAA AAGGATCTTC ACCTAGATCC TTTTAAATTA
                                                              13560
AAAATGAAGT TTTAAATCAA ATATGAGTAA ACTTGGTCTG ACAGTTACCA
                                                              13620
ATGCTTAATC AGTGAGGCAC CTATCTCAGC GATCTGTCTA TTTCGTTCAT CCATAGTTGC
                                                              13680
CTGACTCCCC GTCGTGTAGA TAACTACGAT ACGGGAGGGC TTACCATCTG GCCCCAGTGC
                                                              13740
TGCAATGATA CCGCGAGACC CACGCTCACC GGCTCCAGAT TTATCAGCAA TAAACCAGCC
                                                              13800
AGCCGGAAGG GCCGAGCGCA GAAGTGGTCC TGCAACTTTA TCCGCCTCCA TCCAGTCTAT
                                                              13860
```

FIG. 7W

```
TAATTGTTGC CGGGAAGCTA GAGTAAGTAG TTCGCCAGTT AATAGTTTGC GCAACGTTGT     13920
TGCCATTGCT GCAGGCATCG TGGTGTCACG CTCGTCGTTT GGTATGGCTT CATTCAGCTC     13980
CGGTTCCCAA CGATCAAGGC GAGTTACATG ATCCCCCATG TTGTGCAAAA AAGCGGGTTAG    14040
CTCCTTCGGT CCTCCGATCG TTGTCAGAAG TAAGTTGGCC GCAGTGTTAT CACTCATGGT    14100
TATGGCAGCA CTGCATAATT CTCTTACTGT CATGCCATCC GTAAGATGCT TTTCTGTGAC    14160
TGGTGAGTAC TCAACCAAGT CATTCTGAGA ATAGTGTATG CGGGCGACCGA GTTGCTCTTG   14220
CCCGGCGTCA ACACGGGATA ATACCGCGCC ACATAGCAGA ACTTTAAAAG TGCTCATCAT    14280
TGGAAAACGT TCTTCGGGGC GAAAACTCTC AAGGATCTTA CCGCTGTTGA GATCCAGTTC    14340
GATGTAACCC ACTCGTGCAC CCAACTGATC TTCAGCATCT TTTACTTTCA CCAGCGTTTC    14400
TGGGTGAGCA AAAACAGGAA GGCAAAATGC CGCAAAAAAG GGAATAAGGG CGACACGGAA    14460
ATGTTGAATA CTCATACTCT TCCTTTTTCA ATATTATTGA AGCATTTATC AGGGTTATTG    14520
```

FIG. 7X

TCTCATGAGC GGATACATAT TTGAATGTAT TTAGAAAAAT AAACAAATAG GGGTTCCGCG 14580
CACATTTCCC CGAAAAGTGC CACCTGACGT CTAAGAAACC ATTATTATCA TGACATTAAC 14640
CTATAAAAAT AGGCGTATCA CGAGGCCCTT TCGTCTTCAA GAA 14683

FIG. 8A

```
TTAATTAAGG GGGGGAGAAT GGGCGGAACT GGGCGGAGTT AGGGGCGGGA TGGGCGGAGT    60
TAGGGGCGGG ACTATGGTTG CTGACTAATT GAGATGCATG CTTGCATAC  TTCTGCCTGC   120
TGGGGAGCCT GGGGACTTTC CACACCTGGT TGCTGACTAA TTGAGATGCA TGCTTTGCAT   180
ACTTCTGCCT GCTGGGGAGC CTGGGGACTT TCCACACCCT AACTGACACA CATTCCACAG   240
AATTAATTCC CCTAGTTATT AATAGTAATC AATTACGGGG TCATTAGGTC ATAGCCCATA   300
TATGGAGTTC CGCGTTACAT AACTTACGGT AAATGCCCG CCTGGCTGAC CGCCCAACGA    360
CCCCCGCCCA TTGACGTCAA TAATGACGTA TGTTCCCATA GTAACGCCAA TAGGGACTTT   420
CCATTGACGT CAATGGGTGG ACTATTTACG GTAAACTGCC CACTTGGCAG TACATCAAGT   480
GTATCATATG CCAAGTACGC CCCCTATTGA CGTCAATGAC GGTAAATGGC CCGCCTGGCA   540
TTATGCCCAG TACATGACCT TATGGGACTT TCCTACTTGG CAGTACATCT ACGTATTAGT   600
CATCGCTATT ACCATGGTGA TGCGGTTTTG GCAGTACACC CATTGACGTC AATGGGCGTT   660
TGACTCACGG GGATTTCCAA GTCTCCACCC CATTGACGTC AATGGGAGTT TGTTTTGAAG   720
CTTGGCCGGC CATATAAACG GCGGCCAGCT TTATTTAACG TGTTTACGTC GAGTCAATTG   780
TACACTAACG ACAGTGATGA AGAAATACA  AAGCGGCATA ATATTTTGAA CGACGTCGAA   840
```

FIG. 8B

```
CCTTATTAC AAAACAAAAC ACAAACGAAT ATCGACAAAG CTAGATTGCT GCTACAAGAT    900
TTGGCAAGTT TTGTGGCGTT GAGCGAAAAT CCATTAGATA GTCCAGCCAT CGGTTCGGAA    960
AACAACCCT TGTTTGAAAC TAATCGAAAC CTATTTTACA AATCTATTGA GGATTTAATA   1020
TTTAAATTCA GATATAAAGA CGCTGAAAAT CATTGATTT TCGCTCTAAC ATACCACCCT   1080
AAAGATTATA AATTTAATGA ATTATTAAAA TACATCAGCA ACTATATATT GATAGACATT   1140
TCCAGTTTGT GATATTAGTT TGTGCGTCTC ATTACAATGG CTGTTATTTT TAACAACAAA   1200
CAACTGCTCG CAGACAATAG TATAGAAAAG GGAGGTGAAC TGTTTTTGTT TAACGGTTCG   1260
TACAACATTT TGGAAAGTTA TGTTAATCCG GTGCTGCTAA AAAATGGTGT AATTGAACTA   1320
GAAGAAGCTG CGTACTATGC CGGCAACATA TTGTACAAAA CCGACGATCC CAAATTCATT   1380
GATTATATAA ATTTAATAAT TAAAGCAACA CACTCCGAAG AACTACCAGA AAATAGCACT   1440
GTGTAAATT ACAGAAAAAC TATGCGCAGC GGTACTATAC ACCCCATTAA AAAGACATA   1500
TATATTTATG ACAACAAAAA ATTTACTCTA TACGATAGAT ACATATATGG ATACGATAAT   1560
AACTATGTTA ATTTTATGA GGAGAAAAT GAAAAGAGA AGGAATACGA AGAAGAAGAC   1620
GACAAGGGCGT CTAGTTATG TGAAAATAAA ATTATATTGT CGCAAATTAA CTGTGAATCA   1680
```

FIG. 8C

```
TTTGAAAATG ATTTAAATA TTACCTCAGC GATTATAACT ACGCGTTTTC AATTATAGAT    1740
AATACTACAA ATGTTCTTGT TGCGTTTGGT TTGTATCGTT AATAAAAAAC AAATTTAGCA    1800
TTTATAATTG TTTTATTATT CAATAATTAC AAATAGGATT GAGACCCTTG CAGTTGCCAG    1860
CAAACGGACA GAGCTTGTCG AGGAGAGTTG TTGATTCATT GTTGCCTCC CTGCTGCGGT    1920
TTTTCACCGA AGTTCATGCC AGTCCAGCGT TTTTGCAGCA GAAAGCCGC CGACTTCGGT    1980
TTGCGGTCGC GAGTGAAGAT CCCTTTCTTG TTACCGCCAA CGCGCAATAT GCCTTGCGAG    2040
GTCGCAAAAT CGGCGAAATT CCATACCTGT TCACCGACGA CGGGCGCTGAC GTCGGTGTAC    2100
ACGCGGTGAT ACATATCCAG CCATGCACAC TGATACTCTT CACTCCACAT GTCGGTGTAC    2160
ATTGAGTGCA GCCCGGCTAA CGTATCCACG CCGTATTCGG TGATGATAAT CGGCTGATGC    2220
AGTTCTCCT GCCAGGCCAG AAGTTCTTT TCCAGTACCT TCTCTGCCGT TTCCAAATCG    2280
CCGCTTTGGA CATACCATCC GTAATAACGG TTCAGGCACA GCACATCAAA GAGATCGCTG    2340
ATGGTATCGG TGTGAGCGTC GCAGAACATT ACATTGACGC AGGTGATCGG ACGCGTCGGG    2400
TCGAGTTTAC GCGTTGCTTC CGCCAGTGGC GCGAAATATT CCCGTGCACC TTGCGGACGG    2460
GTATCCGGTT CGTTGGCAAT ACTCCACATC ACCACGCTTG GGTGGTTTTT GTCACGCGCT    2520
```

FIG. 8D

```
ATCAGCTCTT TAATCGCCTG TAAGTGCGCT TGCTGAGTTT CCCCGTTGAC TGCCTCTTCG   2580
CTGTACAGTT CTTTCGGCTT GTTGCCCGCT TCGAAACCAA TGCCTAAAGA GAGGTTAAAG   2640
CCGACAGCAG CAGTTTCATC AATCACCACG ATGCCATGTT CATCTGCCCA GTCGAGCATC   2700
TCTTCAGCGT AAGGGTAATG CGAGGTACGG TAGGAGTTGG CCCCAATCCA GTCCATTAAT   2760
GCGTGGTCGT GCACCATCAG CACGTTATCG AATCCTTTGC CACGCAAGTC CGCATCTTCA   2820
TGACGACCAA AGCCAGTAAA GTAGAACGGT TTGTGGTTAA TCAGGAACTG TTCGCCCTTC   2880
ACTGCCACTG ACCGGATGCC GACGCGAAGC GGGTAGATAT CACACTCTGT CTGGCTTTTG   2940
GCTGTGACGC ACAGTTCATA GAGATAACCT TCACCCGGTT GCCAGAGGTG CGGATTCACC   3000
ACTTGCAAAG TCCCGCTAGT GCCTTGTCCA GTTGCAACCA CCTGTTGATC CGCATCACGC   3060
AGTTCAACGC TGACATCACC ATTGGCCACC ACCTGCCAGT CAACAGACGC GTGGTTACAG   3120
TCTTGGCGGA CATGCGTCAC CACGGTGATA TCGTCCACCC AGGTGTTCGG CGTGGTGTAG   3180
AGCATTACGC TGCGATGGAT TCCGGCATAG TTAAAGAAAT CATGGAAGTA AGACTGCTTT   3240
TTCTTGCCGT TTCGTCGGT AATCACCATT CCCGGGCGGA TAGTCTGCCA GTTCAGTTCG   3300
TTGTTCACAC AAACGGGTGAT ACCCCTCGAC GGATTAAAGA CTTCAAGCGG TCAACTATGA   3360
```

FIG. 8E

```
AGAAGTGTTC GTCTTCGTCC CAGTAAGCTA TGTCTCCAGA ATGTAGCCAT CCATCCTTGT    3420
CAATCAAGGC GTTGGTCGCT TCCGGATTGT TTACATAACC GGACATAATC ATAGGTCCTC    3480
TGACACATAA TTCGCCTCTC TGATTAACGC CCAGCGTTTT CCCGGTATCC AGATCCACAA    3540
CCTTCGCTTC AAAAAATGGA ACAACTTTAC CGACCGGCC CGGTTTATCA TCCCCCTCGG     3600
GTGTAATCAG AATAGCTGAT GTAGTCTCAG TGAGCCCATA TCCTTGTCGT ATCCCTGGAA    3660
GATGGAAGCG TTTTGCAACC GCTTCCCCGA CTTCTTTCGA AAGAGGTGCG CCCCCAGAAG    3720
CAATTTCGTG TAAATTAGAT AAATCGTATT TGTCAATCAG AGTGCTTTTG GCGAAGAATG    3780
AAAATAGGGT TGGTACTAGC AACGCACTTT GAATTTGTA ATCCTGAAGG GATCGTAAAA     3840
ACAGCTCTTC TTCAAATCTA TACATTAAGA CGACTCGAAA TCCACATATC AAATATCCGA    3900
GTGTAGTAAA CATTCCAAAA CCGTGATGGA ATGGAACAAC ACTTAAAATC GCAGTATCCG    3960
GAATGATTTG ATTGCCAAAA ATAGGATCTC TGGCATGCGA GAATCTAGCG CAGGCAGTTC    4020
TATGCGGAAG GGCCACACCC TTAGGTAACC CAGTAGATCC AGAGGAATTG TTTTGTCACG    4080
ATCAAAGGAC TCTGGTACAA AATCGTATTC ATTAAAACCG GGAGGTAGAT GAGATGTGAC    4140
GAACGTGTAC ATCGACTGAA ATCCCTGGTA ATCCGTTTTA GAATCCATGA TAATAATTTT    4200
```

FIG. 8F

```
CTGGATTATT GGTAATTTTT TTTGCACGTT CAAAATTTTT TGCAACCCCT TTTTGGAAAC   4260
AAACACTACG GTAGGCTGCG AAATGTTCAT ACTGTTGAGC AATTCACGTT CATTATAAAT   4320
GTCGTTCGCG GGCGCAACTG CAACTCCGAT AAATAACGCG CCCAACACCG GCATAAAGAA   4380
TTGAAGAGAG TTTTCACTGC ATACGACGAT TCTGTGATTT GTATTCAGCC CATATCGTTT   4440
CATAGCTTCT GCCAACCGAA CGGACATTC GAAGTATTCC GCGTACGTGA TGTTCACCTC   4500
GATATGTGCA TCTGTAAAAG GAATTGTTCC AGGAACCAGG GCGTATCTCT TCATAGCCTT   4560
ATGCAGTTGC TCTCCAGCGG TTCCATCCTC TAGCTTTGCT TCTCAATTTC TTATTGCAT    4620
AATGAGAAAA AAAGGAAAAT TAATTTTAAC ACCAATTCAG TAGTTGATTG AGCAAATGCG   4680
TTGCCAAAAA GGATGCTTTA GAGACAGTGT TCTCTGCACA GATAAGGACA AACATTATTC   4740
AGAGGGAGTA CCCAGAGCTG AGACTCCTAA GCCAGTGAGT GGCACAGCAT TCTAGGGAGA   4800
AATATGCTTG TCATCACCGA AGCCTGATTC CGTAGAGCCA CACCTTGGTA AGGGCCAATC   4860
TGCTCACACA GGATAGAGAG GGCAGGAGC AGGGCAGAGC ATATAAGGTG AGGTAGGATC   4920
AGTTGCTCCT CACATTTGCT TCTGACATAG TTGTGTTGGG AGCTTGGATC GATCCACCAT   4980
GGGCTTCAAT ACCCTGATTG ACTGGAACAG CTGTAGCCCT GAACAGCAGC GTGCGCTGCT   5040
```

FIG. 8G

```
GACGCGTCCG GCGATTCCG CCTCTGACAG TATTACCCGG ACGGTCAGCG ATATTCTGGA  5100
TAATGTAAAA ACGGGCGGTG ACGATGCCCT GCGTGAATAC AGCGCTAAAT TTGATAAAAC  5160
AGAAGTGACA GCGCTACGCG TCACCCCTGA AGAGATCGCC GCCGCCGGCG CGGCGTCTGAG  5220
CGACGAATTA AAACAGGCGA TGACCGCTGC CGTCAAAAAT ATTGAAACGT TCCATTCCGC  5280
GCAGACGCTA CCGCCTGTAG ATGTGGAAAC CCAGCCAGGC GTGCGTTGCC AGCAGGTTAC  5340
GCGTCCCGTC TCGTCTGTCG GTCTGTATAT TCCCGGGGGC TCGGCTCCGC TCTTCTCAAC  5400
GGTGCTGATG CTGGCGACGC CGGCGGCGCAT TGCGGGATGC CAGAAGGTGG TTCTGTGCTC  5460
GCCGCCGCCC ATCGCTGATG AAATCCTCTA TGCGGGCGCAA CTGTGTGGCG TGCAGGAAAT  5520
CTTTAACGTC GGCGGGCGGC AGGGCGATTGC CGCTCTGGCC TTCGGCAGCG AGTCCGTACC  5580
GAAAGTGGAT AAAATTTTTG GCCCCGGGCAA CGCCTTTGTA ACCGAAGCCA AACGTCAGGT  5640
CAGCCAGCGT CTCGACGGCG CGGCTATCGA TATGCCAGCC GGGCCGTCTG AAGTACTGGT  5700
GATCGCAGAC AGCGGGCGCAA CACCGGATTT CGTCGCTTCT GACCTGCTCT CCCAGGCTGA  5760
GCACGGCCCG GATTCCCAGG TGATCCTGCT GACGCCTGAT GCTGACATTG CCCGCAAGGT  5820
GGCGGAGGCG GTAGAACGTC AACTGGGCGGA ACTGCCGGCG CGGGACACCG CCCGGCAGGC  5880
```

FIG. 8H

```
CCTGAGCGCC AGTCGTCTGA TTGTGACCAA AGATTAGCG CAGTGCGTCG CCATCTCTAA    5940
TCAGTATGGG CCGGAACACT TAATCATCCA GACGCGCAAT GCGCGCGATT TGGTGGATGC    6000
GATTACCAGC GCAGGCTCGG TATTTCTCGG CGACTGGTCG CCGGAATCCG CCGGTGATTA    6060
CGCTTCCGGA ACCAACCATG TTTTACCGAC CTATGGCTAT ACTGCTACCT GTCCAGCCT    6120
TGGGTTAGCG GATTTCCAGA AACGGATGAC CGTTCAGGAA CTGTCGAAAG CGGGCTTTTC    6180
CGCTCTGGCA TCAACCATTG AAACATTGGC GGCGGCAGAA CGTCTGACCG CCCATAAAAA    6240
TGCCCGTGACC CTGCGCGTAA ACGCCCTCAA GGAGCAAGCA TGAGCACTGA AAACACTCTC    6300
AGCGTCGCTG ACTTAGCCCG TGAAAATGTC CGCAACCTGG AGATCCAGAC ATGATAAGAT    6360
ACATTGATGA GTTTGGACAA ACCACAACTA GAATGCAGTG AAAAAAATGC TTTATTTGTG    6420
AAATTTGTGA TGCTATTGCT TTATTTGTAA TCATTATAAG CTGCAATAAA CAAGTTAACA    6480
ACAACAATTG CATTCATTTT ATGTTTCAGG TTCAGGGGGA GGTGTGGGAG GTTTTTTAAA    6540
GCAAGTAAAA CCCTCTACAAA TGTGGTATGG CTGATTATGA TCTCTAGCTC GACGGCCGC    6600
CTCTAGAGCA GTGTGGTTTT GCAAGAGGAA GCAAAAGCC TCTCCACCCA GGCCTGGAAT    6660
GTTCCACCC AATGTCGAGC AGTGTGGTTT TGCAAGAGGA AGCAAAAGC CTCTCCACCC    6720
```

FIG. 81

```
AGGCCTGGAA TGTTCCACC CAATGTCGAG CAAACCCGC CCAGCGTCTT GTCATTGGCG     6780
AATTCGAACA CGCAGATGCA GTCGGGGCGG CGCGGTCCCA GTCCCACTTC GCATATTAAG   6840
GTGACGCGTG TGGCCTCGAA CACCGAGCGA CCCTGCAGCC AATATGGGAT CGGCCATTGA   6900
ACAAGATGGA TTGCACGCAG GTTCTCCGGC CGCTTGGGTG GAGAGGCTAT TCGGCTATGA   6960
CTGGGCACAA CAGACAATCG GCTGCTCTGA TGCCGCCGTG TTCCGGCTGT CAGCGCAGGG   7020
GCGCCCGGTT CTTTTGTCA AGACCGACCT GTCCGGTGCC CTGAATGAAC TGCAGGTAAG    7080
TGCGGCCGTC GATGGCCGAG GCGGACTCGG CCTCTGCATA AATAAAAAAA ATTAGTCAGC   7140
CATGCATGGG GCGGAGAATG GGCGGAACTG GGCGGGGGAT GGGCGGAGTT              7200
AGGGGCGGGA CTATGGTTGC TGACTAATTG AGATGCATGC TTTGCATACT TCTGCCTGCT   7260
GGGGAGCCTG GGGACTTTCC ACACCTGGTT GCTGACTAAT TGAGATGCAT GCTTTGCATA   7320
CTTCTGCCTG CTGGGGAGCC TGGGGACTTT CCACACCCTA ACTGACACAC ATTCCACAGA   7380
ATTAATTCCC CTAGTTATTA ATAGTAATCA ATTACGGGGT CATTAGTTCA TAGCCCATAT   7440
ATGGAGTTCC GCGTTACATA ACTTACGGTA AATGGCCCGC CTGGCTGACC GCCCAACGAC   7500
CCCGCCCAT TGACGTCAAT AATGACGTAT GTTCCCATAG TAACGCCAAT AGGGACTTTC    7560
```

FIG. 8J

```
CATTGACGTC AATGGGTGGA CTATTTACGG TAAACTGCCC ACTTGGCAGT ACATCAAGTG    7620
TATCATATGC CAAGTACGCC CCCTATTGAC GTCAATGACG GTAAATGGCC CGCCTGGCAT    7680
TATGCCCAGT ACATGACCTT ATGGGACTTT CCTACTTGGC AGTACATCTA GCTATTAGTC    7740
ATCGCTATTA CCATGGTGAT GCGGTTTTGG CAGTACATCA ATGGGCGTGG ATAGCGGTTT    7800
GACTCACGGG GATTTCCAAG TCTCCACCCC ATTGACGTCA ATGGGAGTTT GTTTTGGCAC    7860
CAAAATCAAC GGGACTTTCC AAAATGTCGT AACAACTCCG CCCCATTGAC GCAAATGGGC    7920
GGTAGGCGTG TACGGTGGGA GGTCTATATA AGCAGAGCTG GGTACGTGAA CCGTCAGATC    7980
GCCTGGAGAC GCCATCACAG ATCTCTCACT ATGGATTTTC AGGTGCAGAT TATCAGCTTC    8040
CTGCTAATCA GTGCTTCAGT CTGCATCTCC AGAGGACAAA TTGTTCTCTC CCAGTCTCCA    8100
GCAATCCTGT CTGCATCTCC AGGGGAGAAG GTCACAATGA CTTGCAGGGC CAGCTCAAGT    8160
GTAAGTTACA TCCACTGGTT CCAGCAGAAG CCAGGATCCT CCCCAAACC CTGGATTTAT    8220
GCCACATCCA ACCTGGCTTC TGGAGTCCCT GTTCGCTTCA GTGGCAGTGG GTCTGGGACT    8280
TCTTACTCTC TCACAATCAG CAGAGTGGAG GCTGAAGATG CTGCCACTTA TTACTGCCAG    8340
CAGTGGGACTA GTAACCCACC CACGTTCGGA GGGGGGACCA AGCTGGAAAT CAAACGTACG    8400
```

FIG. 8K

```
GTGGCTGCAC CATCTGTCTT CATCTTCCCG CCATCTGATG AGCAGTTGAA ATCTGGAACT  8460
GCCTCTGTTG TGTGCCTGCT GAATAACTTC TATCCCAGAG AGGCCAAAGT ACAGTGGAAG  8520
GTGGATAACG CCCTCCAATC GGGTAACTCC CAGGAGAGTG TCACAGAGCA GGACAGCAAG  8580
GACAGCACCT ACAGCCTCAG CAGCACCCTG ACGCTGAGCA AAGCAGACTA CGAGAAACAC  8640
AAAGTCTACG CCTGCGAAGT CACCCATCAG GGCCTGAGCT CGCCCGTCAC AAAGAGCTTC  8700
AACAGGGGAG AGTGTTGAAT TCAGATCCGT TAACGGTAC CAACTACCTA GACTGGATTC  8760
GTGACAACAT GCGGCCGTGA TATCTACGTA TGATCAGCCT CGACTGTGCC TTCTAGTTGC  8820
CAGCCATCTG TTGTTTGCCC CTCCCCCGTG CCTTCCTTGA CCCTGGAAGG TGCCACTCCC  8880
ACTGTCCTTT CCTAATAAAA TGAGGAAATT GCATCGCATT GTCTGAGTAG GTGTCATTCT  8940
ATTCTGGGGG GTGGGGTGGG GCAGGACAGC AAGGGGGAGG ATTGGGAAGA CAATAGCAGG  9000
CATGCTGGGG ATGCGGTGGG CTCTATGGAA CCAGCTGGGG CTCGACAGCT ATGCCAAGTA  9060
CGCCCCTAT TGACGTCAAT GACGGTAAAT GGCCCGCCTG GCATTATGCC CAGTACATGA  9120
CCTTATGGGA CTTTCCTACT TGGCAGTACA TCTACGTATT AGTCATCGCT ATTACCATGG  9180
TGATGCGGTT TTGGCAGTAC ATCAATGGGC GTGGATAGCG GTTTGACTCA CGGGGATTTC  9240
```

FIG. 8L

```
CAAGTCTCCA CCCCATTGAC GTCAATGGGA GTTTGTTTTG GCACCAAAAT CAACGGGACT    9300
TTCCAAAATG TCGTAACAAC TCCGCCCCAT TGACGCAAAT GGGCGGTAGG CGTGTACGGT    9360
GGGAGGTCTA TATAAGCAGA GCTGGGTACG TCCTCACATT CAGTGATCAG CACTGAACAC    9420
AGACCCGTCG ACATGGGTTG GAGCCTCATC TTGCTCTCTCC TTGTCGCTGT TGCTACGCGT    9480
GTCCTGTCCC AGGTACAACT GCAGCAGCCT GGGGCTGAGC TGGTGAAGCC TGGGGCCTCA    9540
GTGAAGATGT CCTGCAAGGC TTCTGGCTAC ACATTACCA GTTACAATAT GCACTGGGTA    9600
AAACAGACAC CTGGTCGGGG CCTGGAATGG ATTGGAGCTA TTTATCCCGG AAATGGTGAT    9660
ACTTCCTACA ATCAGAAGTT CAAAGGCAAG GCCACATTGA CTGCAGACAA ATCCTCCAGC    9720
ACAGCCTACA TGCAGCTCAG CAGCCTGACA TCTGAGGACT CTGCGGTCTA TTACTGTGCA    9780
AGATCGACTT ACTACGGGCGG TGACTGGTAC TTCAATGTCT GGGGCGCAGG GACCACGGTC    9840
ACCGTCTCTG CAGCTAGCAC CAAGGGCCCA TCGGTCTTCC CCCTGGCACC CTCCTCCAAG    9900
AGCACCTCTG GGGGCACAGC GGCCCTGGGC TGCCTGGTCA AGGACTACTT CCCCGAACCG    9960
GTGACGGTGT CGTGGAACTC AGGCGCCCTG ACCAGCGGCG TGCACACCTT CCCGGCTGTC   10020
CTACAGTCCT CAGGACTCTA CTCCCTCAGC AGCGTGGTGA CCGTGCCCTC CAGCAGCTTG   10080
```

FIG. 8M

```
GGCACCCAGA CCTACATCTG CAACGTGAAT CACAAGCCCA GCAACACCAA GGTGGACAAG   10140
AAGCAGAGC  CCAAATCTTG TGACAAAACT CACACATGCC CACCGTGCCC AGCACCTGAA   10200
CTCCTGGGGG GACCGTCAGT CTTCCTCTTC CCCCCAAAAC CCAAGGACAC CCTCATGATC   10260
TCCCGGACCC CTGAGGTCAC ATGCGTGGTG GTGGACGTGA GCCACGAAGA CCCTGAGGTC   10320
AAGTTCAACT GGTACGTGGA CGGCGTGGAG GTGCATAATG CCAAGACAAA GCCGCGGGAG   10380
GAGCAGTACA ACAGCACGTA CCGTGTGGTC AGCGTCCTCA CCGTCCTGCA CCAGGACTGG   10440
CTGAATGGCA AGGAGTACAA GTGCAAGGTC TCCAACAAAG CCCTCCCAGC CCCCATCGAG   10500
AAAACCATCT CCAAAGCCAA AGGGCAGCCC CGAGAACCAC AGGTGTACAC CCTGCCCCCA   10560
TCCCGGGATG AGCTGACCAA GAACCAGGTC AGCCTGACCT GCCTGGTCAA AGGCTTCTAT   10620
CCCAGCGACA TCGCCGTGGA GTGGGAGAGC AATGGGCAGC CGGAGAACAA CTACAAGACC   10680
ACGCCTCCCG TGCTGGACTC CGACGGCTCC TTCTTCCTCT ACAGCAAGCT CACCGTGGAC   10740
AAGAGCAGGT GGCAGCAGGG GAACGTCTTC TCATGCTCCG TGATGCATGA GGCTCTGCAC   10800
AACCACTACA CGCAGAAGAG CCTCTCCCTG TCTCCGGGTA AATGAGGATC CGTTAACGGT   10860
TACCAACTAC CTAGACTGGA TTCGTGACAA CATGCGGCCG TGATATCTAC GTATGATCAG   10920
```

FIG. 8N

```
CCTCGACTGT GCCTTCTAGT TGCCAGCCAT CTGTTGTTTG CCCCTCCCCC GTGCCTTCCT   10980
TGACCCTGGA AGGTGCCACT CCCACTGTCC TTTCCTAATA AAATGAGGAA ATTGCATCGC   11040
ATTGTCTGAG TAGGTGTCAT TCTATTCTGG GGGGTGGGGT GGGGCAGGAC AGCAAGGGGG   11100
AGGATTGGGA AGACAATAGC AGGCATGCTG GGGATGCGGT GGGCTCTATG GAACCAGCTG   11160
GGGCTCGACA GCAACGCTAG GTCGAGGCCG CTACTAACTC TCTCCTCCCT CCTTTTTCCT   11220
GCAGGACGAG GCAGGCGCGGC TATCGTGGCT GGCCACGACG GGCGTTCCTT GCCGCAGCTGT  11280
GCTCGACGTT GTCACTGAAG CGGGAAGGGA CTGGCTGCTA TTGGGCGAAG TGCCGGGGCA   11340
GGATCTCCTG TCATCTCACC TTGCTCCCTGC CGAGAAAGTA TCCATCATGG CTGATGCAAT   11400
GCGGCGGCTG CATACGCTTG ATCCGGCTAC CTGCCCATTC GACCACCAAG CGAAACATCG   11460
CATCGAGCGA GCACGTACTC GGATGGAAGC CGGTCTTGTC GATCAGGATG ATCTGGACGA   11520
AGAGCATCAG GGGCTCGCGC CAGCCGAACT GTTCGCCAGG TAAGTGAGCT CCAATTCAAG   11580
CTTCCTAGGG CGGCCAGCTA GTAGCTTTGC TTCTCAATTT CTTATTTGCA TAATGAGAAA   11640
AAAAGGAAAA TTAATTTTAA CACCAATTCA GTAGTTGATT GAGCAAATGC GTTGCCAAAA   11700
AGGATGCTTT AGAGACAGTG TTCTCTGCAC AGATAAGGAC AAACATTATT CAGAGGGAGT   11760
```

FIG. 8P

```
ACCCAGAGCT GAGACTCCTA AGCCAGTGAG TGGCACAGCA TTCTAGGGAG AAATATGCTT   11820
GTCATCACCG AAGCCTGATT CCGTAGAGCC ACACCTTGGT AAGGGCCAAT CTGCTCACAC   11880
AGGATAGAGA GGGCAGGAGC CAGGGCAGAG CATATAAGGT GAGGTAGGAT CAGTTGCTCC   11940
TCACATTTGC TTCTGACATA GTTGTGTTGG GAGCTTGGAT AGCTTGGACA GCTCAGGGCT   12000
GCCGATTTCGC ACGGCAATCC TAGCGTGAAG GCTGGTAGGA TTTTATCCCC             12060
GCTGCCATCA TGGTTCGACC ATTGAACTGC ATCGTCGCCG TGTCCCAAAA TATGGGGATT   12120
GGCAAGAACG GAGACCTACC CTGGCCTCCG CTCAGGAACG AGTTCAAGTA CTTCCAAAGA   12180
ATGACCACAA CCTCTTCAGT GGAAGGTAAA CAGAATCTGG TGATTATGGG TAGGAAAACC   12240
TGGTTCTCCA TTCCTGAGAA GAATCGACCT TTAAAGGACA GAATTAATAT AGTTCTCAGT   12300
AGAGAACTCA AAGAACCACC ACGAGGAGCT CATTTCTTG CCAAAAGTTT GGATGATGCC    12360
TTAAGACTTA TTGAACAACC GGAATTGGCA AGTAAAGTAG ACATGGTTTG GATAGTCGGA   12420
GGCAGTTCTG TTTACCAGGA AGCCATGAAT CAACCAGGCC ACCTTAGACT CTTTGTGACA   12480
AGGATCATGC AGGAATTTGA AAGTGACACC TTTTTCCCAG AAATTGATTT GGGGAAATAT   12540
AAACTTCTCC CAGAATACCC AGGCGTCCTC TCTGAGGTCC AGGAGGAAAA AGGCATCAAG   12600
```

FIG. 8Q

```
TATAAGTTTG AAGTCTACGA GAAGAAAGAC TAACAGGAAG ATGCTTTCAA GTTCTCTGCT   12660
CCCTCCTAA  AGCTATGCAT TTTATAAGA  CCATGGGACT TTTGCTGGCT TTAGATCAGC   12720
CTCGACTGTG CCTTCTAGTT GCCAGCCATC TGTTGTTGC  CCCTCCCCCG TGCCTTCCTT   12780
GACCCTGGAA GGTGCCACTC CCACTGTCCT TCCTAATAA  AATGAGGAAA TTGCATCGCA   12840
TTGTCTGAGT AGGTGTCATT CTATTCTGGG GGGTGGGGTG GGGCAGGACA GCAAGGGGGA   12900
GGATTGGGAA GACAATAGCA GGCATGCTGG GGCTCTATGG AACCAGCTGG             12960
GGCTCGAAGC GGCCGCCCAT TTCGCTGGTG GTCAGATGCG GGATGGCGGTG GGACGCGGCG  13020
GGGAGCGGTCA CACTGAGGTT TTCCGCCAGA CGCCACTGCT GCCAGGCGCT GATGTGCCCG  13080
GCTTCTGACC ATGCGGTCGC GTTCGGTTGC ACTACGCGTA CTGTGAGCCA GAGTTGCCCG   13140
GCGCTCTCCG GCTGCGGGTAG TTCAGGCAGT TCAATCAACT GTTACCTTG  TGGACCGACA   13200
TCCAGAGGCA CTTCACCGCT TGCCAGCGGC TTACCATCCA GCGCCACCAT CCAGTGCAGG   13260
AGCTCGTTAT CGCTATGACG GAACAGGTAT TCGCTGGTCA CTTCGATGGT TTGCCCGGAT   13320
AAACGGAACT GGAAAAACTG CTGCTGGTGT TTGCTTCCG  TCAGCGCTGG ATGCGGCGTG   13380
CGGTCGGCAA AGACCAGACC GTTCATACAG AACTGGCGAT CGTTCGGGCGT ATCGCCAAAA  13440
```

FIG. 8R

```
TCACCGCCGT AAGCCGACCA CGGGTTGCCG TTTCATCAT ATTTAATCAG CGACTGATCC   13500
ACCCAGTCCC AGACGAAGCC GCCCTGTAAA CGGGGATACT GACGAAACGC CTGCCAGTAT   13560
TTAGCGAAAC CGCCAAGACT GTTACCCATC GCTGGGGCGT ATTCGCAAAG GATCAGCGGG   13620
CGCGTCTCTC CGGGTAGCGA AAGCCATTTT TTGATGGACC ATTTCGGACC AGCCGGGAAG   13680
GGCTGGTCTT CATCCACGCG CGGTACATC GGGCAAATAA TATCGGTGGC CGTGGTGTCG   13740
GCTCCCGCCGC CTTCATACTG CACCGGGCGG GAAGGATCGA CAGATTTGAT CCAGCGATAC   13800
AGCGCGTCGT GATTAGCGCC GTGGCCTGAT TCATTCCCCA GCGACCAGAT GATCACACTC   13860
GGGTGATTAC GATCGCGGCTG CACCATTCGC GTTACGCCGTT CGCTCATCGC CGGTAGCCAG   13920
CGCGGGATCAT CGGTCAGACG ATTCATTGGC ACCATGCCGT GGGTTTCAAT ATTGGCTTCA   13980
TCCACCACAT ACAGGCCCGTA GCGGTCGCAC AGCGTGTACC ACAGCGGATG GTTCGGATAA   14040
TGCCAACAGC GCACGGCGTT AAAGTTGTTC TGCTTCATCA GCAGGATATC CTGACGCCATC   14100
GTCTGCTCAT CCATGACCTG ACCATGCAGA GGATGATGCT CGTGACGCGTT AACGCCTCGA   14160
ATCAGCAACG GCTTGCCGTT CAGCAGCAGC AGACCATTTT CAATCCGCAC CTCGCGGAAA   14220
CCGACATCGC AGGCTTCTGC TTCAATCAGC GTGCCGTCGG CGGTGTGCAG TTCAACCACC   14280
```

FIG. 8S

```
GCACGATAGA GATTCGGGAT TTCGGCGCTC CACAGTTTCG GGTTTTCGAC GTTCAGACGC   14340
AGTGTGACGC GATCGGCATA ACCACCACGC TCATCGATAA TTTCACCGCC GAAAGGCGCG   14400
GTGCCGCTGG CGACCTGCGT TTCACCCTGC CATAAAGAAA CTGTTACCCG TAGGTAGTCA   14460
CGCAACTCGC CGCACATCTG AACTTCAGCC TCCAGTACAG CGCGGGCTGAA ATCATCATTA  14520
AAGCGAGTGG CAACATGGAA ATCGCTGATT TGTGTAGTCG GTTTATGCAG CAACGAGACG   14580
TCACGGAAAA TGCCGCTCAT CCGCCACATA TCCTGATCTT CCAGATAACT GCCGTCACTC   14640
CAACGCAGCA CCATCACCGC GAGGCGGTTT TCTCCGGCCG GTAAAAATGC GCTCAGGTCA   14700
AATTCAGACG GCAAACGACT GTCCTGGCCG TAACCGACCC ACGCCCCGTT GCACCACAGA   14760
TGAAACGCCG AGTTAACGCC ATCAAAAATA ATTCGCGTCT GGCCTTCCTG TAGCCAGCTT   14820
TCATCAACAT TAAATGTGAG CGAGTAACAA CCCGTCGGAT TCTCCGTGGG AACAAACGGC   14880
GGATTGACCG TAATGGGATA GGTTACGTTG GTGTAGATGG GCGCATCGTA ACCGTGCATC   14940
TGCCAGTTTG AGGGGACGAC GACAGTATCG GCCTCAGGAA GATCGCACTC CAGCCAGCTT   15000
TCCGGCACCG CTTCTGGTGC CGGAAACCAG GCAAAGCGCC ATTCGCCATT CAGGCTGCGC   15060
AACTGTTGGG AAGGGCGATC GGTGCGGGCC TCTTCGCTAT TACGCCAGCT GGCGAAAGGG   15120
```

FIG. 8T

```
GGATGTGCTG CAAGGCGATT AAGTTGGGTA ACGCCAGGGT TTTCCCAGTC ACGACGTTGT  15180
AAACGACTT AATCCGTCGA GGGGCTGCCT CGAAGCAGAC GACCTTCCGT TGTGCAGCCA   15240
GCGGCGCCTG CGCCGGTGCC CACAATCGTG CGCGAACAAA CTAAACCAGA ACAAATTATA  15300
CCGGGGGCAC CGCCGCCACC ACCTTCTCCC GTGCCCTAACA TTCCAGCGCC TCCACCACCA 15360
CCACCACCAT CGATGTCTGA ATTGCCGCCC GCTCCACCAA TGCCGACGGA ACCTCAACCC  15420
GCTGCACCTT TAGACGACAG ACAACAATTG TTGGAAGCTA TTAGAAACGA AAAAAATCGC  15480
ACTCGTCTCA GACCGGTCAA ACCAAAAACG GCGCCCGAAA CCAGTACAAT AGTTGAGGTG  15540
CCGACTGTGT TGCCTAAAGA GACATTTGAG CCTAAACCGC CGTCTGCATC ACCGCCACCA  15600
CCTCCGCCTC CGCCTCCGCC GCCAGCCCCG CCTGCCGCCTC CACCGATGGT AGATTTATCA 15660
TCAGCTCCAC CACCGCCCGCC ATTAGTAGAT TGCCGTCTG AAATGTTACC ACCGCCTGCA  15720
CCATCGCTTT CTAACGTGTT GTCTGAATTA AATCGGGCA CAGTAGAGATT GAAACCCGCC   15780
CAAAAACGCC CGCAATCAGA AATAATTCCA AAAAGCTCAA CTACAAATTT GATCGCGGAC  15840
GTGTTAGCCG ACACAATTAA TAGGCGTCGT GTGGCTATGG CAAAATCGTC TTCGGAAGCA  15900
ACTTCTAACG ACGAGGGTTG GGACGACGAC GATAATCGGC CTAATAAAGC TAACACGCCC  15960
```

FIG. 8U

```
GATGTTAAAT ATGTCCAAGC TACTAGTGGT ACCGCTTGGC AGAACATATC CATCGCGTCC   16020
GCCATCTCCA GCAGCCGCAC GCGGGCGCATC TCGGGCAGCG TTGGGTCCTG GCCACGGGTG  16080
CGCATGATCG TGCTCCTGTC GTTGAGGACC CGGCTAGGCT GGCGGGGTG CCTTACTGGT    16140
TAGCAGAATG AATCACCGAT ACGCGAGCGA ACGTGAAGCG ACTGCTGCTG CAAAACGTCT   16200
GCGACCTGAG CAACAACATG AATGGTCTTC GGTTCCGTG TTTCGTAAAG TCTGGAAACG    16260
CGGAAGTCAG CGCCCTGCAC CATTATGTTC CGGATCTGCA TCGCAGGATG CTGCTGGCTA   16320
CCCTGTGGAA CACCTACATC TGTATTAACG AAGGCTGGC ATTGACCCTG AGTGATTTT     16380
CTCTGGTCCC GCCGCATCCA TACCGCCAGT TGTTTACCCT CACAACGTTC CAGTAACCGG   16440
GCATGTTCAT CATCAGTAAC CCGTATCGTG AGCATCCTCT CTCGTTTCAT CGGTATCATT   16500
ACCCCCATGA ACAGAAATCC CCCTTACACG GAGGCATCAG TGACCAAACA GGAAAAAACC   16560
GCCCTTAACA TGGCCCGCTT TATCAGAAGC CAGACATTAA CGCTTCTGGA GAAACTCAAC   16620
GAGCTGGACG CGGATGAACA GGCAGACATC TGTGAATCGC TTCACGACCA CGCTGATGAG   16680
CTTTACCGCA GCTGCCTCGC GCGTTTCGGT GATGACGGTG AAAACCTCTG ACACATGCAG   16740
CTCCCGGAGA CGGTCACAGC TTGTCTGTAA GCGGATGCCG GGAGCAGACA AGCCCGTCAG   16800
```

FIG. 8V

```
GGCGGCGGTCAG CGGGTGTGTTGG CGGGTGTGTCGG GGCGGCAGCCA TGACCCAGTCACGTAGCGAT  16860
AGCGGAGTGT ATACTGGCTT AACTATGCGG CATCAGAGCA GATTGTACTG AGAGTGCACC        16920
ATATGCGGTG TGAAATACCG CACAGATGCG TAAGGAGAAA ATACCGCATC AGGCGCTCTT        16980
CCGCTTCCTC GCTCACTGAC TCGCTGCGCT CGGTCGTTCG GCTGCGGCGA GCGGTATCAG        17040
CTCACTCAAA GGCGGTAATA CGGTTATCCA CAGAATCAGG GGATAACGCA GGAAAGAACA        17100
TGTGAGCAAA AGGCCAGCAA AAGGCCAGGA ACCGTAAAAA GGCCGCGTTG CTGGCGTTTT        17160
TCCATAGGCT CCGCCCCCCT GACGAGCATC ACAAAAATCG ACGCTCAAGT CAGAGGTGGC        17220
GAAACCCGAC AGGACTATAA AGATACCAGG CGTTTCCCCC TGGAAGCTCC CTCGTGCGCT        17280
CTCCTGTTCC GACCCTGCCG CTTACCGGAT ACCTGTCCGC CTTTCTCCCT TCGGGAAGCG        17340
TGGCGCTTTC TCATAGCTCA CGCTGTAGGT ATCTCAGTTC GGTGTAGGTC GTTCGCTCCA        17400
AGCTGGGCTG TGTGCACGAA CCCCCCGTTC AGCCCGACCG CTGCGCCTTA TCCGGTAACT        17460
ATCGTCTTGA GTCCAACCCG GTAAGACACG ACTTATCGCC ACTGGCAGCA GCCACTGGTA        17520
ACAGGATTAG CAGAGCGAGG TATGTAGGCG GTGCTACAGA GTTCTTGAAG TGGTGGCCTA        17580
ACTACGGCTA CACTAGAAGG ACAGTATTTG GTATCTGCGC TCTGCTGAAG CCAGTTACCT        17640
```

FIG. 8W

```
TCGGAAAAAG AGTTGGTAGC TCTTGATCCG GCAAACAAAC CACCGCTGGT AGCGGTGGTT   17700
TTTTGTTTG CAAGCAGCAG ATTACGCGCA GAAAAAAGG ATCTCAAGAA GATCCTTTGA    17760
TCTTTCTAC GGGGTCTGAC GCTCAGTGGA ACGAAAACTC ACGTTAAGGG ATTTGGTCA    17820
TGAGATTATC AAAAGGATC TTCACCTAGA TCCTTTTAAA TTAAAATGA AGTTTTAAAT    17880
CAATCTAAAG TATATATGAG TAAACTTGGT CTGACAGTTA CCAATGCTTA ATCAGTGAGG   17940
CACCTATCTC AGCGATCTGT CTATTTCGTT CATCCATAGT TGCCTGACTC CCCGTCGTGT   18000
AGATAACTAC GATACGGGAG GGCTTACCAT CTGGCCCCAG TGCTGCAATG ATACCGCGAG   18060
ACCCACGCTC ACCGGCTCCA GATTTATCAG CAATAAACCA GCCAGCCGGA AGGGCCGAGC   18120
GCAGAAGTGG TCCTGCAACT TTATCCGCCT CCATCCAGTC TATTAATTGT TGCCGGGAAG   18180
CTAGAGTAAG TAGTTCGCCA GTTAATAGTT TGCGCAACGT TGTTGCCATT GCTGCAGGCA   18240
TCGTGGTGTC ACGCTCGTCG TTTGGTATGG CTTCATTCAG CTCCGGTTCC CAACGATCAA   18300
GGCGAGTTAC ATGATCCCCC ATGTTGTGCA AAAAGCGGT TAGCTCCTTC GGTCCTCCGA    18360
TCGTTGTCAG AAGTAAGTTG GCCGCAGTGT TATCACTCAT GGTTATGGCA GCACTGCATA   18420
ATTCTCTTAC TCGTAAGAT GCTTTTCTGT GACTGGTGAG TACTCAACCA               18480
```

FIG. 8X

```
AGTCATTCTG AGAATAGTGT ATGCGGGGAC CGAGTTGCTC TTGCCCGGCG TCAACACGGG   18540
ATAATACCGC GCCACATAGC AGAACTTTAA AAGTGCTCAT CATTGGAAAA CGTTCTTCGG   18600
GGCGAAAACT CTCAAGGATC TTACCGCTGT TGAGATCCAG TTCGATGTAA CCCACTCGTG   18660
CACCCAACTG ATCTTCAGCA TCTTTTACTT TCACCAGCGT TTCTGGGTGA GCAAAAACAG   18720
GAAGGCAAAA TGCCGCAAAA AAGGGAATAA GGGCGACACG GAAATGTTGA ATACTCATAC   18780
TCTTCCTTTT TCAATATTAT TGAAGCATTT ATCAGGGTA TTGTCTCATG AGCGGATACA    18840
TATTTGAATG TATTTAGAAA AATAAACAAA TAGGGGTTCC GCGCACATTT CCCCGAAAAG   18900
TGCCACCTGA CGTCTAAGAA ACCATTATTA TCATGACATT AACCTATAAA AATAGGCGTA   18960
TCACGAGGCC CTTTCGTCTT CAAGAA                                        18986
```

FIG. 9

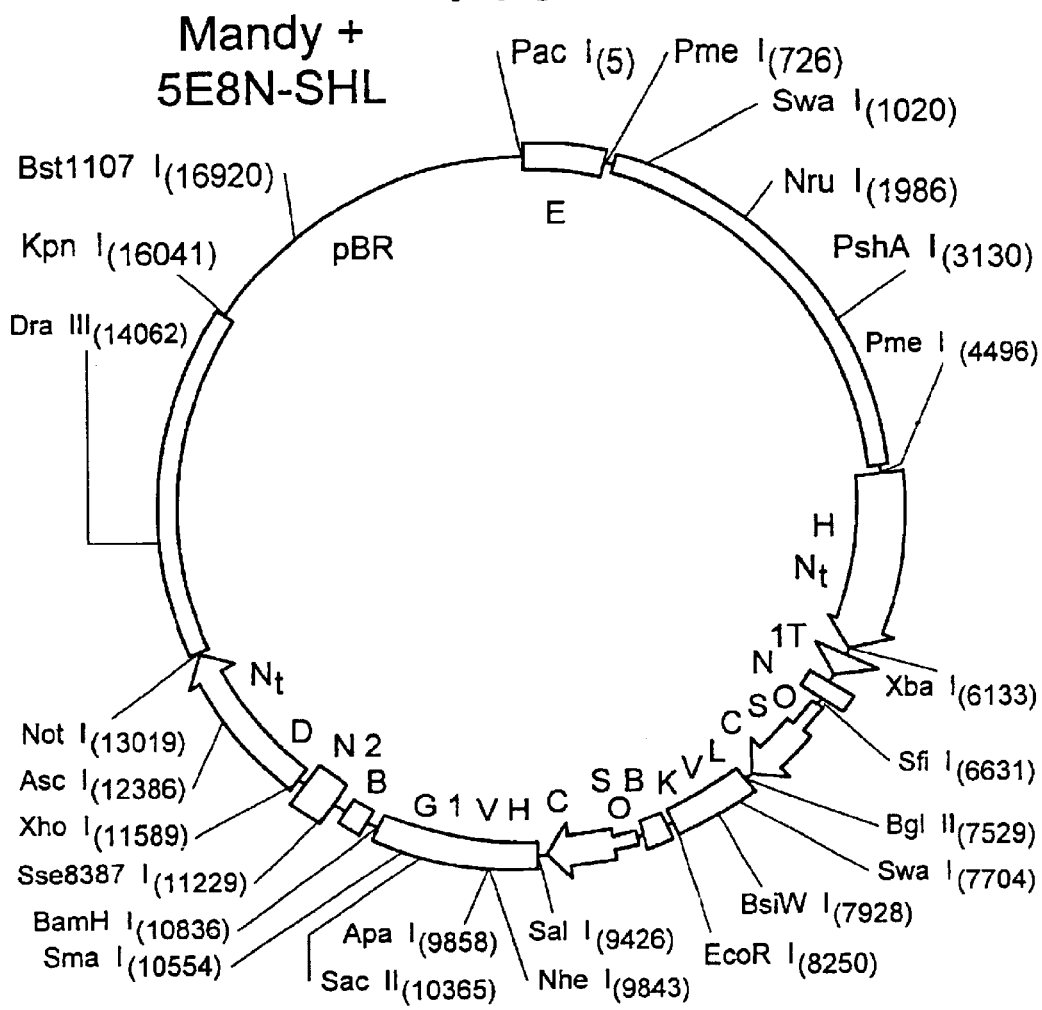

Nt D = Inactive Dihydrofolate reductase
E = CMV and SV40 enhancers
Nt H = Inactive Samonella Histidinol Dehydrogenase
T = Herpes Simplex thymidine kinas promoter and polyoma enhancer
C = Cytomegalovirus promoter/enhancer
N1 = Neomycin phosphotransferase exon 1
K = Human kappa constant
VL = Variable light chain anti-CD23 primate 5E8 and leader
VH = Variable heavy chain anti-CD-23 primate 5E8N- and leader
B = Bovine growth hormone polyadenylation
M2 = Neomycin phosphotransferase exon 2
G1 = Human Gamma 1 constant
Mandy cut XbaI Xho I and ligated to Xba I Xho I fragment
from XKG1+CD23 5E8N-SHL
Map by Mitchell Reff    Constructed by Karen McLachlan    06/26/97    19,035 bp
Noncutters = AflII, AvrII, HindIII, I-Ppol, I-Scel, PmlI, RsrII, SgfI, SrfI

FIG. 10A

```
        10         20         30         40         50         60         70
TTAATTAAGG GGCGGAGAAT GGGCGGAACT GGGCGGGAGTT AGGGGCGGGA TGGGCGGAGT TAGGGGCGGG
        80         90        100        110        120        130        140
ACTATGGTTG CTGACTAATT GAGATGCATG CTTTGCATAC AGGGGAGCCT TGGGGAGCCT GGGGACTTTC
       150        160        170        180        190        200        210
CACACCTGGT TGCTGACTAA TGCTGACTGCA TGCTTTGCAT ACTTCTGCCT GCTGGGGAGC CTGGGGACTT
       220        230        240        250        260        270        280
TCCACACCCT AACTGACACA CATTCCACAG AATTAATTCC CCTAGTTATT AATAGTAATC AATTACGGGG
       290        300        310        320        330        340        350
TCATTAGTTC ATAGCCCATA CGCGTTACAT AACTTACGGT AAATGGCCCG CCTGGCTGAC
       360        370        380        390        400        410        420
CGCCAACGA CCCCCGCCCA TTGACGTCAA TAATGACGTA TGTTCCCATA GTAACGCCAA TAGGGACTTT
       430        440        450        460        470        480        490
CCATTGACGT CAATGGGTGG AGTATTACG GTAAACTGCC CACTTGGCAG TACATCAAGT GTATCATATG
       500        510        520        530        540        550        560
CCAAGTACGC CCCCTATTGA CGTCAATGAC GGTAAATGGC CCGCCTGGCA TTATGCCCAG TACATGACCT
       570        580        590        600        610        620        630
TATGGGACTT TCCTACTTGG CAGTACATCT ACGTATTAGT CATCGCTATT ACCATGGTGA TGCGGTTTTG
       640        650        660        670        680        690        700
GCAGTACATC AATGGGCGTG GATAGCGGTT TGACTCACGG GGATTTCCAA GTCTCCACCC CATTGACGTC
       710        720        730        740        750        760        770
AATGGGAGTT TGTTTTGAAG CTGTTTAAAC AGCTTGGCCG GCCAGCTTTA TTTAACGTGT TACGTCGAG
       780        790        800        810        820        830        840
TCAATTGTAC ACTAACGACA GTGATGAAAG AAATACAAAA GCGCATAATA TTTTGAACGA CGTCGAACCT
       850        860        870        880        890        900        910
TTATTACAAA ACAAAACACA AACGAATATC GACAAAGCTA GATTGCTGCT ACAAGATTTG GCAAGTTTTG
       920        930        940        950        960        970        980
TGGCGTTGAG CGAAAATCCA TTAGATAGTC CAGCCATCGG TTCGGAAAAA CAACCCTTGT TTGAAACTAA
```

FIG. 10A

| 990 | 1000 | 1010 | 1020 | 1030 | 1040 | 1050 |
|---|---|---|---|---|---|---|
| TCGAAACCTA | TTTTACAAAT | CTATTGAGGA | TTTAATATTT | AAATTCAGAT | ATAAAGACGC | TGAAAATCAT |
| 1060 | 1070 | 1080 | 1090 | 1100 | 1110 | 1120 |
| TTGATTTCG | CTCTAACATA | CCACCCTAAA | GATTATAAAT | TTAATGAATT | ATTAAAATAC | ATCAGCAACT |
| 1130 | 1140 | 1150 | 1160 | 1170 | 1180 | 1190 |
| ATATATTGAT | AGACATTCC | AGTTTGTGAT | ATTAGTTTGT | GCGTCTCATT | ACAATGGCTG | TTATTTTAA |
| 1200 | 1210 | 1220 | 1230 | 1240 | 1250 | 1260 |
| CAACAAACAA | CTGCTCGCAG | ACAATAGTAT | AGAAAAGGGA | GGTGAACTGT | TTTTGTTAA | CGGTTCGTAC |
| 1270 | 1280 | 1290 | 1300 | 1310 | 1320 | 1330 |
| AACATTTTGG | AAAGTTATGT | CTGCTAAAAA | ATGGTGTAAT | TGAACTAGAA | GAAGCTGCGT | 1400 |
| 1340 | 1350 | 1360 | 1370 | 1380 | 1390 | 1470 |
| ACTATGCCGG | CAACATATTG | TACAAAACCG | ACGATCCCAA | ATTCATTGAT | TATATAAATT | TAATAATTAA |
| 1410 | 1420 | 1430 | 1440 | 1450 | 1460 | 1540 |
| AGCAACACAC | TCCGAAGAAC | TACCAGAAAA | TAGCACTGTT | GTAAATTACA | GAAAAACTAT | GCGCAGCGGT |
| 1480 | 1490 | 1500 | 1510 | 1520 | 1530 | 1610 |
| ACTATACACC | CCATTAAAAA | AGACATATAT | ATTTATGACA | ACAAAAAATT | TACTCTATAC | GATAGATACA |
| 1550 | 1560 | 1570 | 1580 | 1590 | 1600 | 1680 |
| TATATGGATA | CGATAATAAC | TATGTTAATT | TTTATGAGGA | GAAAATGAA | AAAGAGAAGG | AATACGAAGA |
| 1620 | 1630 | 1640 | 1650 | 1660 | 1670 | 1750 |
| AGAAGACGAC | AAGGCGTCTA | GTTTATGTGA | AAATAAAATT | ATATTGTCGC | AAATTAACTG | TGAATCATTT |
| 1690 | 1700 | 1710 | 1720 | 1730 | 1740 | 1820 |
| GAAAATGATT | TTAAATATTA | CCTCAGCGAT | TATAACTACG | CGTTTTCAAT | TATAGATAAT | ACTACAAATG |
| 1760 | 1770 | 1780 | 1790 | 1800 | 1810 | 1890 |
| TTCTTGTTGC | GTTTGGTTTG | TATCGTTAAT | AAAAAACAAA | TTTGACATTT | ATAATTGTTT | TATTATTCAA |
| 1830 | 1840 | 1850 | 1860 | 1870 | 1880 | 1960 |
| TAATTACAAA | TAGGATTGAG | ACCCTTGCAG | TTGCCAGCAA | ACGGACAGAG | CTTGTCGAGG | AGAGTTGTTG |
| 1900 | 1910 | 1920 | 1930 | 1940 | 1950 | |
| ATTCATTGTT | TGCCTCCCTG | CTGCGGGTTT | TCACGAAGT | TCATGCCAGT | CCAGCGTTTT | TGCAGCAGAA |

```
        1970        1980        1990        2000        2010        2020        2030
AAGCCGCCGA  CTTCGGTTTG  CGGTCGGCGAG TGAAGATCCC TTTCTTGTTA  CCGCCAACGC  GCAATATGCC
        2040        2050        2060        2070        2080        2090        2100
TTGCGAGGTC  GCAAAATCGG  CGAAATTCCA  TACCTGTTCA  CCGACGACGG  CGCTGACGCG  ATCAAAGACG
        2110        2120        2130        2140        2150        2160        2170
CGGTGATACA  TATCCAGCCA  TGCACACTGA  TACTCTTCAC  TCCACATGTC  GGTGTACATT  GAGTGCAGCC
        2180        2190        2200        2210        2220        2230        2240
CGGCTAACGT  ATCCACGCCG  TATTCGGTGA  TGATAATCGG  CTGATGCAGT  TTCTCCTGCC  AGGCCAGAAG
        2250        2260        2270        2280        2290        2300        2310
TTCTTTTCC   AGTACCTTCT  CTGCCGTTTC  CAAATCGCCG  CTTTGGGACAT ACCATCCGTA  ATAACGGTTC
        2320        2330        2340        2350        2360        2370        2380
AGGCACAGCA  CATCAAAGAG  ATCGCTGATG  GTATCGGTGT  GAGCGTCGCA  GAACATTACA  TTGACGCAGG
        2390        2400        2410        2420        2430        2440        2450
TGATCGGACG  CGTCGGGTCG  AGTTTACGCG  TTGCTTCCGC  CAGTGGGCGG  AAATATTCCC  GTGCACCTTG
        2460        2470        2480        2490        2500        2510        2520
CGGACGGGTA  TCCGGTTCGT  TGGCAATACT  CCACATCACC  ACGCTTGGGT  GGTTTTGTC   ACGCGCTATC
        2530        2540        2550        2560        2570        2580        2590
AGCTCTTAA   TCGCCTGTAA  GTGCGCTTGC  TGAGTTTCCC  CTCTTCGCTG  CTCTTCGCTG  TACAGTTCTT
        2600        2610        2620        2630        2640        2650        2660
TCGGCTTGTT  GCCCGCTTCG  AAACCAATGC  CTAAAGAGAG  GAGCATCTCT  ACAGCAGCAG  TTTCATCAAT
        2670        2680        2690        2700        2710        2720        2730
CACCACGATG  CCATGTTCAT  CTGCCCAGTC  GAGCATCTCT  GTTAAAGCCG  GGTAATGCGA  GGTACGGTAG
        2740        2750        2760        2770        2780        2790        2800
GAGTTGGCCC  CAATCCAGTC  CATTAATGCG  TGGTCGTGCA  TCAGCGTAAG  GTTATCGAAT  CCTTTGCCAC
        2810        2820        2830        2840        2850        2860        2870
GCAAGTCCGC  ATCTTCATGA  CGACCAAAGC  CAGTAAAGTA  CCATCAGCAC  GAACGGTTTG  GGAACTGTTC
        2880        2890        2900        2910        2920        2930        2940
GCCCTTCACT  GCCACTGACC  GGATGCCGAC  GCGAAGCGGG  TAGATATCAC  TGGTTAATCA  GCTTTTGGCT
ACTCTGTCTG
```

```
      2950       2960       2970       2980       2990       3000       3010
GTGACGCACA GTTCATAGAG ATAACCTTCA CCCGGTTGCC AGAGGTGCGG ATTCACCACT TGCAAAGTCC
      3020       3030       3040       3050       3060       3070       3080
CGCTAGTGCC TTGTCCAGTT GCAACCACCT GTTGATCCGC ATCACGCAGT TCAACGCTGA CATCACCATT
      3090       3100       3110       3120       3130       3140       3150
GGCCACCACC TGCCAGTCAA CAGACGCGTG GTTACAGTCT TGCGCGACAT GCGTCACCAC GGTGATATCG
      3160       3170       3180       3190       3200       3210       3220
TCCACCCAGG TGTTCGGCGT GGTGTAGAGC ATTACGCTGC GATGGATTCC GGCATAGTTA AAGAAATCAT
      3230       3240       3250       3260       3270       3280       3290
GGAAGTAAGA CTGCTTTTTC TTGCCGTTT CGTCGGTAAT CACCATTCCC GGGGGGATAG TCTGCCAGTT
      3300       3310       3320       3330       3340       3350       3360
CAGTTCGTTG TTCACACAAA CGGTGATACC CCTCGACGGA TTAAAGACTT CAAGCGGTCA ACTATGAAGA
      3370       3380       3390       3400       3410       3420       3430
AGTGTTCGTC TTCGTCCCAG TAAGCTATGT CTCCAGAATG TAGCCATCCA TCCTTGTCAA TCAAGGCGTT
      3440       3450       3460       3470       3480       3490       3500
GGTCGCTTCC GGATTGTTTA CATAACCGGA CATAATCATA GGTCCTCTGA CACATAATTC GCCTCTCTGA
      3510       3520       3530       3540       3550       3560       3570
TTAACGCCCA GCGTTTTCCC GGTATCCAGA TCCACAACCT TCGCTTCAAA AAATGGAACA ACTTTACCGA
      3580       3590       3600       3610       3620       3630       3640
CCGCGCCCGG TTTATCATCC CCCTCGGGTG TAATCAGAAT AGCTGATGTA GTCTCAGTGA GCCCATATCC
      3650       3660       3670       3680       3690       3700       3710
TTGTCGTATC CCTGGAAGAT GGAAGCGTTT TGCAACCGCT TCCCCGACTT CTTTCGAAAG AGGTGCGCCC
      3720       3730       3740       3750       3760       3770       3780
CCAGAAGCAA TTTCGTGTAA ATTAGATAAA TCGTATTTGT CAATCAGAGT GCTTTTGGCG AAGAATGAAA
      3790       3800       3810       3820       3830       3840       3850
ATAGGGTTGG TACTAGCAAC GCACTTTGAA TTTTGTAATC CTGAAGGGAT CGTAAAAACA GCTCTTCTTC
      3860       3870       3880       3890       3900       3910       3920
AAATCTATAC ATTAAGACGA CTCGAAATCC ACATATCAAA TATCCGAGTG TAGTAAACAT TCCAAAACCG
```

FIG. 10D

```
      3930        3940        3950        3960        3970        3980        3990
TGATGGAATG  GAACAACACT  TAAAATCGCA  GTATCCGGAA  TGATTTGATT  GCCAAAAATA  GGATCTCTGG
      4000        4010        4020        4030        4040        4050        4060
CATGCGAGAA  TCTGACGCAG  GCAGTTCTAT  GCGGAAGGGC  CACACCCTTA  GGTAACCCAG  TAGATCCAGA
      4070        4080        4090        4100        4110        4120        4130
GGAATTGTTT  TGTCACGATC  AAAGGACTCT  GGTACAAAAT  CGTATTCATT  AAAACCGGGA  GGTAGATGAG
      4140        4150        4160        4170        4180        4190        4200
ATGTGACGAA  CGTGTACATC  GACTGAAATC  CCTGGTAATC  CGTTTTAGAA  TCCATGATAA  TAATTTTCTG
      4210        4220        4230        4240        4250        4260        4270
GATTATTGGT  AATTTTTTT   GCACGTTCAA  AATTTTTTGC  AACCCCTTTT  TGGAAACAAA  CACTACGGTA
      4280        4290        4300        4310        4320        4330        4340
GGCTGCGAAA  TGTTCATACT  GTTGAGCAAT  TCACGTTCAT  TATAAATGTC  GTTCGCGGGC  GCAACTGCAA
      4350        4360        4370        4380        4390        4400        4410
CTCCGATAAA  TAACGCGCCC  AACACCGGCA  TAAAGAATTG  AAGAGAGTTT  TCACTGCATA  CGACGATTCT
      4420        4430        4440        4450        4460        4470        4480
GTGATTGTA   TTCAGCCCAT  ATCGTTTCAT  AGCTTCTGCC  AACCGAACGG  ACATTTCGAA  GTATTCCGCG
      4490        4500        4510        4520        4530        4540        4550
TACAGCCCGG  CCGTTTAAAC  GGCCCGGGCT  CAATACCCTG  ATTGACTGGA  ACAGCTGTAG  CCCTGAACAG
      4560        4570        4580        4590        4600        4610        4620
CAGCGTGCGC  TGCTGACGCG  TCCGGCGATT  TCCGCCTCTG  ACAGTATTAC  CCGGACGGTC  AGCCGATATTC
      4630        4640        4650        4660        4670        4680        4690
TGGATAATGT  GGTGACGATG  CCCTGCGTGA  ATACAGCGCT  AAATTTGATA  AAACAGAAGT
      4700        4710        4720        4730        4740        4750        4760
GACAGCGCTA  CGCGTCACCC  CTGAAGAGAT  CGCCGCCGCC  GGCGGCGCGA  TGAGCGACGA  ATTAAAACAG
      4770        4780        4790        4800        4810        4820        4830
GCGATGACCG  CTGCCGTCAA  AAATATTGAA  ACGTTCCATT  CCGCGCAGAC  GCTACCGCCT  GTAGATGTGG
      4840        4850        4860        4870        4880        4890        4900
AAACCCAGCC  AGGGCGTGCGT  TGCCAGCAGG  TTACGCGTCC  CGTCTCGTCT  GTCGGTCTGT  ATATTCCCGG
```

FIG. 10E

```
     4910        4920        4930        4940        4950        4960        4970
CGGCTCGGCT  CCGCTCTTCT  CAACGGTGCT  GATGCTGGCG  ACGCCGGGCG  GCATTGCGGG  ATGCCAGAAG
     4980        4990        5000        5010        5020        5030        5040
GTGGTTCTGT  GCTCGCCGCC  GCCCATCGCT  GATGAAATCC  TCTATGCGGC  GCAACTGTGT  GGCGTGCAGG
     5050        5060        5070        5080        5090        5100        5110
AAATCTTTAA  CGTCGGCGGC  GCGCAGGCGA  TTTGCCGCTCT GGCCTTCGGC  AGCGAGTCCG  TACCGAAAGT
     5120        5130        5140        5150        5160        5170        5180
GGATAAAATT  TTTGGCCCCG  GCAACGCCTT  TGTAACCGAA  GCCAAACGTC  AGGTCAGCCA  GCGTCTCGAC
     5190        5200        5210        5220        5230        5240        5250
GGCGCGGCTA  TCGATATGCC  AGCCGGGCGG  TCTGAAGTAC  TGGTGATCGC  AGACAGCGGC  GCAACACCGG
     5260        5270        5280        5290        5300        5310        5320
ATTCGTCGC   TTCTGACCTG  CTCTTCCCAGG CTGAGCACGG  CCCGGATTCC  CAGGTGATCG  TGCTGACGCC
     5330        5340        5350        5360        5370        5380        5390
TGATGCTGAC  ATTGCCCGCA  AGGTGGCGGA  GGGGGTAGAA  CGTCAACTGG  CGGAACTGCC  GCGGCCGGAC
     5400        5410        5420        5430        5440        5450        5460
ACCGCCCGGC  AGGCCCTGAG  CGCCAGTCGT  CTGATTGTGA  CCAAAGATTT  AGCGCAGTGC  GTCGCCATCT
     5470        5480        5490        5500        5510        5520        5530
CTAATCAGTA  TGGGCCGGAA  CACTTAATCA  TCCAGACGCG  CAATGCGCGC  GATTGGTGG   ATGCGATTAC
     5540        5550        5560        5570        5580        5590        5600
CAGCGCAGGC  TCGGTATTTC  TCGGGCGACTG GTCGCCGGAA  TCCGCCGGTG  GATTTGGTGG  ATGCGATTAC
     5610        5620        5630        5640        5650        5660        5670
CAGCGCAGGC  TCGGTATTTC  TCGGGCGACTG GTCGCCGACTG TCCGCCGGTG  AGCGGATTTC  CGGAACCAAC
     5680        5690        5700        5710        5720        5730        5740
CATGTTTTAC  CGACCTATGG  CTATACTGCT  ACCTGTTCCA  GCCTTGGGTT  AGCGGATTTC  CAGAAACGGA
     5750        5760        5770        5780        5790        5800        5810
TGACCGTTCA  GGAACTGTCG  AAAGCGGGCT  TTTCCGCTCT  GGCATCAACC  ATTGAAACAT  TGGCGGCGGC
     5820        5830        5840        5850        5860        5870        5880
AGAACGTCTG  ACCGCCCATA  AAAATGCCGT  GACCCTGAAA  GTAAACGCCC  TCAAGGAGCA  AGCATGAGCA

CTGAAAACAC  TCTCAGCGTC  GCTGACTTAG  CCCGTGAAAA  TGTCCGCAAC  CTGGAGATCC  AGACATGGAT
```

FIG. 10F

| | | | | | |
|---|---|---|---|---|---|
| 5890 | 5900 | 5910 | 5920 | 5930 | 5940 | 5950 |
| AAGATACATT | GATGAGTTTG | GACAAACCAC | AACTAGAAATG | CAGTGAAAAA | AATGCTTTAT | TTGTGAAATT |
| 5960 | 5970 | 5980 | 5990 | 6000 | 6010 | 6020 |
| TGTGATGCTA | TTGCTTTATT | TGTAACCATT | ATAAGCTGCA | ATAAACAAGT | TAACAACAAC | AATTGCATTC |
| 6030 | 6040 | 6050 | 6060 | 6070 | 6080 | 6090 |
| ATTTTATGTT | TCAGGTCAG | GGGGAGGTGT | GGGAGGTTTT | TTAAAGCAAG | TAAAACCTCT | ACAAATGTGG |
| 6100 | 6110 | 6120 | 6130 | 6140 | 6150 | 6160 |
| TATGGCTGAT | TATGATCTCT | AGGGCCGGCC | CTCGACGGCG | CGTCTAGAGC | AGTGTGGTTT | TCAAGAGGAA |
| 6170 | 6180 | 6190 | 6200 | 6210 | 6220 | 6230 |
| GCAAAAAGCC | TCTCCACCCA | GGCCTGGAAT | GTTCCACCC | AATGTCGAGC | AGTGTGGTTT | TGCAAGAGGA |
| 6240 | 6250 | 6260 | 6270 | 6280 | 6290 | 6300 |
| AGCAAAAAGC | CTCTCCACCC | AGGCCTGGAA | TGTTTCCACC | CAATGTCGAG | CAAACCCCGC | CCAGCGTCTT |
| 6310 | 6320 | 6330 | 6340 | 6350 | 6360 | 6370 |
| GTCATTGGCG | AATTGGAACA | CGCATATGCA | GTCGGGGGCGG | CGCGGTCCCA | GGTCCACTTC | GCATATTAAG |
| 6380 | 6390 | 6400 | 6410 | 6420 | 6430 | 6440 |
| GTGCGCGTG | TGGCCTCGAA | CACCGAGCGA | CCCTGCAGCC | AATATGGGAT | CGGCCATTGA | ACAAGATGGA |
| 6450 | 6460 | 6470 | 6480 | 6490 | 6500 | 6510 |
| TTGCACGCAG | GTTCTCCGGC | CGCTTGGGTG | GAGAGGCTAT | TCGGCTATGA | CTGGGCACAA | CAGACAATCG |
| 6520 | 6530 | 6540 | 6550 | 6560 | 6570 | 6580 |
| GCTGCTCTGA | TGCCGCCGTG | TTCCGGCTGT | CAGCGCAGGG | GCGCCCGGTT | CTTTTTGTCA | AGACCGACCT |
| 6590 | 6600 | 6610 | 6620 | 6630 | 6640 | 6650 |
| GTCCGGTGCC | CTGAATGAAC | TGCAGGTAAG | TGCGGCCGTC | GATGGCCGAG | GCGGCCTCGG | CCTCTGCATA |
| 6660 | 6670 | 6680 | 6690 | 6700 | 6710 | 6720 |
| AATAAAAAAA | ATTAGTCAGC | CATGCATGGG | GCGGAGAATG | GGCGGAACTG | GGCGGAGTTA | GGGGCGGGAT |
| 6730 | 6740 | 6750 | 6760 | 6770 | 6780 | 6790 |
| GGGCGGAGTT | AGGGGCGGGA | CTATGGTTGC | TGACTAATTG | AGATGCATGC | TTTGCATACT | TCTGCCTGCT |
| 6800 | 6810 | 6820 | 6830 | 6840 | 6850 | 6860 |
| GGGGAGCCTG | GGGACTTTCC | ACACCTGGTT | GCTGACTAAT | TGAGATGCAT | GCTTTGCATA | CTTCTGCCTG |

FIG. 10G

|      6870 |      6880 |      6890 |      6900 |      6910 |      6920 |      6930 |
|-----------|-----------|-----------|-----------|-----------|-----------|-----------|
| CTGGGGAGCC | TGGGACTTT | CCACACCCTA | ACTGACACAC | ATTCCACAGA | ATTAATTCCC | CTAGTTATTA |
|      6940 |      6950 |      6960 |      6970 |      6980 |      6990 |      7000 |
| ATAGTAATCA | ATTACGGGT | CATTAGTTCA | TAGCCCATAT | ATGGAGTTCC | GCGTTACATA | ACTTACGGTA |
|      7010 |      7020 |      7030 |      7040 |      7050 |      7060 |      7070 |
| AATGCCCCGC | CTGGCTGACC | GCCCAACGAC | CCCGCCCAT | TGACGTCAAT | AATGACGTAT | GTTCCCATAG |
|      7080 |      7090 |      7100 |      7110 |      7120 |      7130 |      7140 |
| TAACGCCAAT | AGGGACTTTC | CATTGACGTC | AATGGGTGGA | GTATTTACGG | TAAACTGCCC | ACTTGGCAGT |
|      7150 |      7160 |      7170 |      7180 |      7190 |      7200 |      7210 |
| ACATCAAGTG | TATCATATGC | CAAGTACGCC | CCCTATTGAC | GTCAATGACG | GTAAATGGCC | CGCCTGGCAT |
|      7220 |      7230 |      7240 |      7250 |      7260 |      7270 |      7280 |
| TATGCCCAGT | ACATGACCTT | ATGGGACTTT | CCTACTTGCC | AGTACATCTA | CGTATTAGTC | ATCGCTATTA |
|      7290 |      7300 |      7310 |      7320 |      7330 |      7340 |      7350 |
| CCATGGTGAT | GCGGTTTTGG | CAGTACATCA | ATGGGCGTGG | ATAGCGGTTT | GACTCACGGG | GATTTCCAAG |
|      7360 |      7370 |      7380 |      7390 |      7400 |      7410 |      7420 |
| TCTCCACCCC | ATTGACGTCA | ATGGGAGTTT | GTTTTGGCAC | CAAAATCAAC | GGGACTTTCC | AAAATGTCGT |
|      7430 |      7440 |      7450 |      7460 |      7470 |      7480 |      7490 |
| AACAACTCCG | CCCCATTGAC | GCAAATGGGC | GGTAGGCGTG | TACGGTGGGA | GGTCTATATA | AGCAGAGCTG |
|      7500 |      7510 |      7520 |      7530 |      7540 |      7550 |      7560 |
| GGTACGTGAA | CCGTCAGATC | GCCTGGAGAC | GCCATCACAG | ATCTCTCACC | ATGGACATGA | GGGTCCCCGC |
|      7570 |      7580 |      7590 |      7600 |      7610 |      7620 |      7630 |
| TCAGCTCCTG | GGGCTCCTTC | TGCTCTGGCT | CCCAGGTGCC | AGATGTGACA | TCCAGATGAC | CCAGTCTCCA |
|      7640 |      7650 |      7660 |      7670 |      7680 |      7690 |      7700 |
| TCTTCCCTGT | CTGCATCTGT | AGGGGACAGA | GTCACCATCA | CTTGCAGGGC | AAGTCAGGAC | ATTAGGTATT |
|      7710 |      7720 |      7730 |      7740 |      7750 |      7760 |      7770 |
| ATTTAAATTG | GTATCAGCAG | AAACCAGGAA | AAGCTCCTAA | GCTCCTGATC | TATGTTGCAT | CCAGTTTGCA |
|      7780 |      7790 |      7800 |      7810 |      7820 |      7830 |      7840 |
| AAGTGGGGTC | CCATCAAGGT | TCAGCGGCAG | TGGATCTGGG | ACAGAGTTCA | CTCTCACCGT | CAGCAGCCTG |

FIG. 10H

```
7850       7860       7870       7880       7890       7900       7910
CAGCCTGAAG ATTTTGCGAC TTATTACTGT CTACAGGTTT ATAGTACCCC TCGGACGTTC GGCCAAGGGA
7920       7930       7940       7950       7960       7970       7980
CCAAGGTGGA AATCAAACGT ACGGTGGCTG CACCATCTGT CTTCATCTTC CCGCCATCTG ATGAGCAGT
7990       8000       8010       8020       8030       8040       8050
GAAATCTGGA ACTGCCTCTG TTGTGTGCCT GCTGAATAAC TTCTATCCCA GAGAGGCCAA AGTACAGTGG
8060       8070       8080       8090       8100       8110       8120
AAGGTGGATA ACGCCCTCCA ATCGGGTAAC TCCCAGGAGA GTGTCACAGA GCAGGACAGC AAGGACAGCA
8130       8140       8150       8160       8170       8180       8190
CCTACAGCCT CAGCAGCACC CTGACGCTGA GCAAAGCAGA CTACGAGAAA CACAAAGTCT ACGCCTGCGA
8200       8210       8220       8230       8240       8250       8260
AGTCACCCAT CAGGGCCTGA GCTCGCCCGT CACAAAGAGC TTCAACAGGG GAGAGTGTTG AATTCAGATC
8270       8280       8290       8300       8310       8320       8330
CGTTAACGGT TACCAACTAC CTAGACTGGA TTCGTGACAA CATGCGGCCG TGATATCTAC GTATGATCAG
8340       8350       8360       8370       8380       8390       8400
CCTCGACTGT GCCTTCTAGT TGCCAGCCAT CTGTTGTTTG CCCCTCCCCC GTGCCTTCCT TGACCCTGGA
8410       8420       8430       8440       8450       8460       8470
AGGTGCCACT CCCACTGTCC TTTCCTAATA AAATGAGGAA ATTGCATCGC ATTGTCTGAG TAGGTGTCAT
8480       8490       8500       8510       8520       8530       8540
TCTATTCTGG GGGGTGGGGT GGGGCAGGAC AGCAAGGGGG AGGATTGGGA AGACAATAGC AGGCATGCTG
8550       8560       8570       8580       8590       8600       8610
GGGATGCGGT GGGCTCTATG GCTTCTGAGG CGGAAAGAAC CAGCTGGGAC TAGTCGCAAT TGGGGCGGAGT
8620       8630       8640       8650       8660       8670       8680
TAGGGGCGGG ATGGGGCGGG TTAGGGGCGG GGACTATGGT GCTGACTAAT TGAGATGCAT GCTTTGCATA
8690       8700       8710       8720       8730       8740       8750
CTTCTGCCTG CTGGGGAGCC TGGGGACTTT CCACACCTGG CCACCCTGG TTGCTGACTA ATTGAGATGC ATGCTTTGCA
8760       8770       8780       8790       8800       8810       8820
TACTTCTGCC TGCTGGGGAG CCTGGGGACT TTCCACACCC TAACTGACAC ACATTCCACA GAATTAATTC
```

FIG. 10I

| | | | | | |
|---|---|---|---|---|---|
| 8830 | 8840 | 8850 | 8860 | 8870 | 8880 | 8890 |
| CCCTAGTTAT | TAATAGTAAT | CAATTACGGG | GTCATTAGTT | CATAGCCCAT | ATATGGAGTT | CCGCGTTACA |
| 8900 | 8910 | 8920 | 8930 | 8940 | 8950 | 8960 |
| TAACTTACGG | TAAATGGCCC | GCCTGGCTGA | CCGCCCAACG | ACCCCCGCCC | ATTGACGTCA | ATAATGACGT |
| 8970 | 8980 | 8990 | 9000 | 9010 | 9020 | 9030 |
| ATGTTCCCAT | AGTAACGCCA | ATAGGGACTT | TCCATTGACG | TCAATGGGTG | GAGTATTTAC | GGTAAACTGC |
| 9040 | 9050 | 9060 | 9070 | 9080 | 9090 | 9100 |
| CCACTTGGCA | GTACATCAAG | TGTATCATAT | GCCAAGTACG | CCCCCTATTG | ACGTCAATGA | CGGTAAATGG |
| 9110 | 9120 | 9130 | 9140 | 9150 | 9160 | 9170 |
| CCCGCCTGGC | ATTATGCCCA | GTACATGACC | TTATGGGACT | TTCCTACTTG | GCAGTACATC | TACGTATTAG |
| 9180 | 9190 | 9200 | 9210 | 9220 | 9230 | 9240 |
| TCATCGCTGT | TACCATGGTG | ATGCGGTTTT | GGCAGTACAT | CAATGGGCGT | GGATAGCGGT | TTGACTCACG |
| 9250 | 9260 | 9270 | 9280 | 9290 | 9300 | 9310 |
| GGGATTTCCA | AGTCTCCACC | CCATTGACGT | CAATGGGAGT | TTGTTTTGGC | ACCAAAATCA | ACGGGACTTT |
| 9320 | 9330 | 9340 | 9350 | 9360 | 9370 | 9380 |
| CCAAAATGTC | GTAACAACTC | CGCCCCATTG | ACGCAAATGG | GCGGTAGGCG | TGTACGGTGG | GAGGTCTATA |
| 9390 | 9400 | 9410 | 9420 | 9430 | 9440 | 9450 |
| TAAGCAGAGC | TGGGTACGTG | AACCGTCAGA | TCGCCTGGAG | ACGCCGTCGA | CATGGGTTGG | AGCCTCATCT |
| 9460 | 9470 | 9480 | 9490 | 9500 | 9510 | 9520 |
| TGCTCTTCCT | TGTCGCTGTT | GCTACGCGTG | TCCTGTCCGA | GGTGCAGCTG | GTGGAGTCTG | GGGGCGGCTT |
| 9530 | 9540 | 9550 | 9560 | 9570 | 9580 | 9590 |
| GGCAAAGCCT | GGGGGGTCCC | TGAGACTCTC | CTGCGCAGCC | TCCGGGTTCA | GGTTCACCTT | CAATAACTAC |
| 9600 | 9610 | 9620 | 9630 | 9640 | 9650 | 9660 |
| TACATGGACT | GGTCCGCCA | GGCTCCAGGG | CAGGGGCTGG | AGTGGGTCTC | ACGTATTAGT | AGTAGTGGTG |
| 9670 | 9680 | 9690 | 9700 | 9710 | 9720 | 9730 |
| TACATGGACT | GTACGCAGAC | TCCGTGAAGG | GCAGATTCAC | CATCTCCAGA | GAGAACGCCA | AGAACACACT |
| 9740 | 9750 | 9760 | 9770 | 9780 | 9790 | 9800 |
| ATCCCACATG | ATGAACAGCC | TGAGAGCTGA | GGACACGGCT | GTCTATTACT | GTGCGAGCTT | GACTACAGGG |
| | | | | | | |
| GTTCTTCAA | | | | | | |

```
9810       9820       9830       9840       9850       9860       9870
TCTGACTCCCT GGGGCCAGGG AGTCCTGGTC ACCGTCTCCT CAGCTAGCAC CAAGGGCCCA TCGGTCTTCC
9880       9890       9900       9910       9920       9930       9940
CCCTGGCACC CTCCTCCAAG AGCACCTCTG GGGGCACAGC GGCCCTGGGC TGCCTGGTCA AGGACTACTT
9950       9960       9970       9980       9990       10000      10010
CCCCGAACCG GTGACGGTGT CGTGGAACTC AGGCGCCCTG ACCAGCGGCG TGCACACCTT CCCGGCTGTC
10020      10030      10040      10050      10060      10070      10080
CTACAGTCCT CAGGACTCTA CTCCCTCAGC AGCGTGGTGA CCGTGCCCTC CAGCAGCTTG GGCACCCAGA
10090      10100      10110      10120      10130      10140      10150
CCTACATCTG CAACGTGAAT CACAAGCCCA GCAACACCAA GGTGGACAAG AAAGTTGAGC CCAAATCTTG
10160      10170      10180      10190      10200      10210      10220
TGACAAAACT CACACATGCC CACCGTGCCC AGCACCTGAA CTCCTGGGGG GACCGTCAGT CTTCCTCTTC
10230      10240      10250      10260      10270      10280      10290
CCCCCAAAAC CCAAGGACAC CCTCATGATC TCCCGGACCC CTGAGGTCAC ATGCGTGGTG GTGGACGTGA
10300      10310      10320      10330      10340      10350      10360
GCCACGAAGA CCCTGAGGTC AAGTTCAACT GGTACGTGGA CGGCGTGGAG GTGCATAATG CCAAGACAAA
10370      10380      10390      10400      10410      10420      10430
GCCGCGGGAG GAGCAGTACA ACAGCACGTA CCGTGTGGTC AGCGTCCTCA CCGTCCTGCA CCAGGACTGG
10440      10450      10460      10470      10480      10490      10500
CTGAATGGCA AGGAGTACAA GTGCAAGGTC TCCAACAAAG CCCTCCCAGC CCCCATCGAG AAAACCATCT
10510      10520      10530      10540      10550      10560      10570
CCAAAGCCAA AGGGCAGCCC CGAGAACCAC AGGTGTACAC CCTGCCCCCA TCCCGGGATG AGCTGACCAA
10580      10590      10600      10610      10620      10630      10640
GAACCAGGTC AGCCTGACCT GCCTGGTCAA AGGCTTCTAT CCCAGCGACA TCGCCGTGGA GTGGGAGAGC
10650      10660      10670      10680      10690      10700      10710
AATGGGCAGC CGGAGAACAA CTACAAGACC ACGCCTCCCG TGCTGGACTC CGACGGCTCC TTCTTCCTCT
10720      10730      10740      10750      10760      10770      10780
ACAGCAAGCT CACCGTGGAC AAGAGCAGGT GGCAGCAGGG GAACGTCTTC TCATGCTCCG TGATGCATGA
```

| | | | | | |
|---|---|---|---|---|---|
| 10790 | 10800 | 10810 | 10820 | 10830 | 10840 | 10850 |
| GGCTCTGCAC | AACCACTACA | CGCAGAAGAG | CCTCTCCCTG | TCTCCGGGTA | AATGAGGATC | CGTTAACGGT |
| 10860 | 10870 | 10880 | 10890 | 10900 | 10910 | 10920 |
| TACCAACTAC | CTAGACTGGA | TTCGTGACAA | CATGCGGCCG | TGATATCTAC | GTATGATCAG | CCTCGACTGT |
| 10930 | 10940 | 10950 | 10960 | 10970 | 10980 | 10990 |
| GCCTTCTAGT | TGCCAGCCAT | CTGTTGTTGC | CCCCTCCCCC | GTGCCTTCCT | TGACCCTGGA | AGGTGCCACT |
| 11000 | 11010 | 11020 | 11030 | 11040 | 11050 | 11060 |
| CCCACTGTCC | TTTCCTAATA | AAATGAGGAA | ATTGCATCGC | ATTGTCTGAG | TAGGTGTCAT | TCTATTCTGG |
| 11070 | 11080 | 11090 | 11100 | 11110 | 11120 | 11130 |
| GGGGTGGGGT | GGGCAGGAC | AGCAAGGGGG | AGGATTGGGA | AGACAATAGC | AGGCATGCTG | GGGATGCGGT |
| 11140 | 11150 | 11160 | 11170 | 11180 | 11190 | 11200 |
| GGGCTCTATG | GCTTCTGAGG | CGGAAAGAAC | CAGCTGGGGC | TCGACAGCAA | CGCTAGGTCG | AGGCCGCTAC |
| 11210 | 11220 | 11230 | 11240 | 11250 | 11260 | 11270 |
| TAACTCTCTC | CTCCCTCCTT | TTTCCTGCAG | GACGAGGCAG | CGCGGCTATC | GTGGCTGGCC | ACGACGGGCG |
| 11280 | 11290 | 11300 | 11310 | 11320 | 11330 | 11340 |
| TTCCTTGCGC | AGCTGTGCTC | GACGTTGTCA | CTGAAGCGGG | AAGGGACTGG | CTGCTATTGG | GCGAAGTGCC |
| 11350 | 11360 | 11370 | 11380 | 11390 | 11400 | 11410 |
| GGGGCAGGAT | CTCCTGTCAT | CTCACCTTGC | TCCTGCCGAG | AAAGTATCCA | TCATGGCTGA | TGCAATGCGG |
| 11420 | 11430 | 11440 | 11450 | 11460 | 11470 | 11480 |
| CGGCTGCATA | CGCTTGATCC | GGCTACCTGC | CCATTCGACC | ACCAAGCGAA | ACATCGCATC | GAGCGAGCAC |
| 11490 | 11500 | 11510 | 11520 | 11530 | 11540 | 11550 |
| GTACTCGGAT | GGAAGCCGGT | CTTGTCGATC | AGGATGATCT | GGACGAAGAG | CATCAGGGGC | TCGCGCCAGC |
| 11560 | 11570 | 11580 | 11590 | 11600 | 11610 | 11620 |
| CGAACTGTTC | GCCAGGTAAG | TGAGCTCCAA | TTCAAGCTCT | CGAGCTAGGG | CGGCCAGCTA | GTAGCTTTGC |
| 11630 | 11640 | 11650 | 11660 | 11670 | 11680 | 11690 |
| TTCTCAATTT | CTTATTTGCA | TAATGAGGAA | AAAGGAAAA | TTAATTTTAA | CACCAATTCA | GTAGTTGATT |
| 11700 | 11710 | 11720 | 11730 | 11740 | 11750 | 11760 |
| GAGCAAATGC | GTTGCCAAAA | AGGATGCTTT | AGAGACAGTG | TTCTCTGCAC | AGATAAGGAC | AAACATTATT |

FIG. 10L

| | | | | | |
|---|---|---|---|---|---|
| 11770 | 11780 | 11790 | 11800 | 11810 | 11820 | 11830 |
| CAGAGGGAGT | ACCCAGAGCT | GAGACTCCTA | AGCCAGTGAG | TGGCACAGCA | TCCAGGGAGA | AATATGCTTG |
| 11840 | 11850 | 11860 | 11870 | 11880 | 11890 | 11900 |
| TCATCACCGA | AGCCTGATTC | CGTAGAGCCA | CACCCTGGTA | AGGGCCAATC | TGCTCACACA | GGATAGAGAG |
| 11910 | 11920 | 11930 | 11940 | 11950 | 11960 | 11970 |
| GGCAGGAGCC | AGGCAGAGC | ATATAAGGTG | AGGTAGGATC | AGTTGCTCCT | CACATTTGCT | TCTGACATAG |
| 11980 | 11990 | 12000 | 12010 | 12020 | 12030 | 12040 |
| TTGTGTTGGG | AGCTTGGATA | GCTTGGGGGG | GGGACAGCTC | AGGGCTGCGA | TTTCGCGCCA | AACTTGACGG |
| 12050 | 12060 | 12070 | 12080 | 12090 | 12100 | 12110 |
| CAATCCTAGC | GTGAAGGCTG | GTAGGATTT | ATCCCCGCTG | CCATCATGGT | TCGACCATTG | AACTGCATCG |
| 12120 | 12130 | 12140 | 12150 | 12160 | 12170 | 12180 |
| TCGCCGTGTC | CCAAAATATG | GGGATTGGCA | AGAACGGAGA | CCTACCCTGG | CCTCCGCTCA | GGAACGAGTT |
| 12190 | 12200 | 12210 | 12220 | 12230 | 12240 | 12250 |
| CAAGTACTTC | CAAAGAATGA | CCACAACCTC | TTCAGTGGAA | GGTAAACAGA | ATCTGGTGAT | TATGGGTAGG |
| 12260 | 12270 | 12280 | 12290 | 12300 | 12310 | 12320 |
| AAAACCTGGT | TCTCCATTCC | TGAGAAGAAT | CGACCTTTAA | AGGACAGAAT | TAATATAGTT | CTCAGTAGAG |
| 12330 | 12340 | 12350 | 12360 | 12370 | 12380 | 12390 |
| AACTCAAAGA | ACCACCACGA | GGAGCTCATT | TTCTTGCCAA | AAGTTTGGAT | GATGCCTTAA | CGTAGGCGCG |
| 12400 | 12410 | 12420 | 12430 | 12440 | 12450 | 12460 |
| CCATTAAGAC | TTATTGAACA | ACCGGAATTG | GCAAGTAAAG | TAGACATGGT | TTGGATAGTC | GGAGGCAGTT |
| 12470 | 12480 | 12490 | 12500 | 12510 | 12520 | 12530 |
| CTGTTTACCA | GGAAGCCATG | AATCAACCAG | GCAACCTCAG | ACTCTTTGTG | ACAAGGATCA | TGCAGGAATT |
| 12540 | 12550 | 12560 | 12570 | 12580 | 12590 | 12600 |
| TGAAAGTGAC | ACGTTTTCC | CAGAAATTGA | TTTGGGGAAA | TATAAACTTC | TCCCAGAATA | CCCAGGCGTC |
| 12610 | 12620 | 12630 | 12640 | 12650 | 12660 | 12670 |
| CTCTCTGAGG | TCAAGGAGGA | AAAAGGCATC | AAGTATAAGT | TTGAAGTCTA | CGAGAAGAAA | GACTAACAGG |
| 12680 | 12690 | 12700 | 12710 | 12720 | 12730 | 12740 |
| AAGATGCTTT | CAAGTTCTCT | GCTCCCCTCC | TAAAGCTATG | CATTTTTATA | AGTATAAGT | ACTTTTGCTG |

FIG. 10M

| | | | | 12810 |
|---|---|---|---|---|
| 12750 | 12760 | 12770 | 12780 | 12790 | 12800 |
| GCTTAGATC | AGCCTCGACT | GTGCCTTCTA | GTTGCCAGCC | ATCTGTTGTT | TGCCCCTCCC | CCGTGCCTTC |
| | | | | | | 12880 |
| | 12820 | 12830 | 12840 | 12850 | 12860 | 12870 |
| CTTGACCCTG | GAAGGTGCCA | CTCCCACTGT | CCTTTGCTAA | TAAAATGAGG | AAATTGCATC | GCATTGTCTG |
| | | | | | | 12950 |
| | 12890 | 12900 | 12910 | 12920 | 12930 | 12940 |
| AGTAGGTGTC | ATTCTATTCT | GGGGGGTGGG | GTGGGGCAGG | ACAGCAAGGG | GGAGGATTGG | GAAGACAATA |
| | | | | | | 13020 |
| | 12960 | 12970 | 12980 | 12990 | 13000 | 13010 |
| GCAGGCATGC | TGGGGATGCG | GTGGGCTCTA | TGGCTTCTGA | GGCGGAAAGA | ACCAGCTGGG | GCTCGAAGCG |
| | | | | | | 13090 |
| | 13030 | 13040 | 13050 | 13060 | 13070 | 13080 |
| GCCGCCCATT | TCGCTGGTGG | TCAGATGCGG | GATGGCGGTGG | GACGCGGCGG | GGAGCGTCAC | ACTGAGGTTT |
| | | | | | | 13160 |
| | 13100 | 13110 | 13120 | 13130 | 13140 | 13150 |
| TCCGCCAGAC | GCCACTGCTG | CCAGGGCGCTG | ATGTGCCGCTG | GACGCGGCGG | TGCGGTCGCG | TTCGGTTGCA |
| | | | | | | 13230 |
| | 13170 | 13180 | 13190 | 13200 | 13210 | 13220 |
| CTACGCGTAC | TGTGAGCCAG | AGTTGCCCGG | CGCTCTCCGG | CTTCTGACCA | CTGCGGTAGT | TCAGGCAGTT | CAATCAACTG |
| | | | | | | 13300 |
| | 13240 | 13250 | 13260 | 13270 | 13280 | 13290 |
| TTTACCTTGT | GGAGCGACAT | CCAGAGGCAC | TTCACCGCTT | GCCAGCGGCT | TACCATCCAG | CGCCACCATC |
| | | | | | | 13370 |
| | 13310 | 13320 | 13330 | 13340 | 13350 | 13360 |
| CAGTGCAGGA | GCTCGTTATC | AACAGGTATT | GCTATGACGG | CGCTGGTCAC | TTCGATGGTT | TGCCCGGATA |
| | | | | | | 13440 |
| | 13380 | 13390 | 13400 | 13410 | 13420 | 13430 |
| AACGGAACTG | GAAAAACTGC | TGCTGGTGTT | TTGCTTCCGT | CAGCGCTGGA | TGCGGCGTGC | GGTCGGCAAA |
| | | | | | | 13510 |
| | 13450 | 13460 | 13470 | 13480 | 13490 | 13500 |
| GACCAGACCG | TTCATACAGA | ACTGGGCGATC | CGTTCGGCTA | TCGCCAAAAT | CACCGCCGTA | AGCCGACCAC |
| | | | | | | 13580 |
| | 13520 | 13530 | 13540 | 13550 | 13560 | 13570 |
| GGGTTGCCGT | TTTCATCATA | TTTAATCAGC | GACTGATCCA | CCCAGTCCCA | GACGAAGCCG | CCCTGTAAAC |
| | | | | | | 13650 |
| | 13590 | 13600 | 13610 | 13620 | 13630 | 13640 |
| GGGGATACTG | ACGAAACGCC | TGCCAGTATT | TAGCGAAACC | GCCAAGACTG | TTACCCATCG | CGTGGGCGTA |
| | | | | | | 13720 |
| | 13660 | 13670 | 13680 | 13690 | 13700 | 13710 |
| TTCGCAAAGG | ATCAGCGGGC | GCGTCTCTCC | AGTAGCGAA | AGCCATTTT | TGATGGACCA | TTTCGGCACA |

FIG. 10N

| | | | | | |
|---|---|---|---|---|---|
| 13730 | 13740 | 13750 | 13760 | 13770 | 13780 | 13790 |
| GCCGGGAAGG | GCTGGTCTTC | ATCCACGCGC | GCGTACATCG | GGCAAATAAT | ATCGGTGGCC | GTGGTGTCGG |
| 13800 | 13810 | 13820 | 13830 | 13840 | 13850 | 13860 |
| CTCCGCCGCC | TTCATACTGC | ACCGGGCGGG | AAGGATCGAC | AGATTTGATC | CAGCGATACA | GCGCGTCGTG |
| 13870 | 13880 | 13890 | 13900 | 13910 | 13920 | 13930 |
| ATTAGCGCCG | TGGCCTGATT | CATTCCCCAG | CGACCAGATG | ATCACACTCG | GGTGATTACG | ATCGCGCTGC |
| 13940 | 13950 | 13960 | 13970 | 13980 | 13990 | 14000 |
| ACCATTCGCG | TTACGCGTTC | GCTCATCGCC | GGTAGCCAGC | GCGGATCATC | GGTCAGACGA | TTCATTGGCA |
| 14010 | 14020 | 14030 | 14040 | 14050 | 14060 | 14070 |
| CCATGCCGTG | GGTTTCAATA | TTGGCTTCAT | CCACCACATA | CAGGCCGTAG | CGGTCGCACA | GCGTGTACCA |
| 14080 | 14090 | 14100 | 14110 | 14120 | 14130 | 14140 |
| CAGCGGATGG | TTCGGATAAT | GCGAACAGCG | CACGGCGTTA | AAGTTGTTCT | GCTTCATCAG | CAGGATATCC |
| 14150 | 14160 | 14170 | 14180 | 14190 | 14200 | 14210 |
| TGCACCATCG | TCTGCTCATC | CATGACCTGA | CCATGCAGAG | GATGATGCTC | GTGACGGTTA | ACGCCTCGAA |
| 14220 | 14230 | 14240 | 14250 | 14260 | 14270 | 14280 |
| TCAGCAACGG | CTTGCCGTTC | AGCAGCAGCA | GACCATTTTC | AATCCGCACC | TCGCGGAAAC | CGACATCGCA |
| 14290 | 14300 | 14310 | 14320 | 14330 | 14340 | 14350 |
| GGCTTCTGCT | TCAATCAGCG | TGCCGTCGGC | GGTGTGCAGT | TCAACCACCG | CACGATAGAG | ATTCGGGATT |
| 14360 | 14370 | 14380 | 14390 | 14400 | 14410 | 14420 |
| TCGGCGCTCC | ACAGTTTCGG | AAAGGGCGCG | TTCAGACGCG | TGCCGCTGGC | GTGTGACGCG | CCACCACGCT |
| 14430 | 14440 | 14450 | 14460 | 14470 | 14480 | 14490 |
| CATCGATAAT | TTCACCGCCG | GCAACTCGCC | TGCCGCTGGC | GACCTGCGTT | ATCGGCATAA | ATAAAGAAAC |
| 14500 | 14510 | 14520 | 14530 | 14540 | 14550 | 14560 |
| TGTTACCCGT | AGGTAGTCAC | GCAACTCGCC | GCACATCTGA | ACTTCAGCCT | CCAGTACAGC | GCGGCTGAAA |
| 14570 | 14580 | 14590 | 14600 | 14610 | 14620 | 14630 |
| CATCATTAA | AGCGAGTGGC | AACATGGAAA | TCGCTGATTT | GTGTAGTCGG | TTTATGCAGC | AACGAGACGT |
| 14640 | 14650 | 14660 | 14670 | 14680 | 14690 | 14700 |
| CACGGAAAAT | GCCGGCTCATC | CGCCACATAT | CCTGATCTTC | CAGATAACTG | CCGTCACTCC | AGCCAGCAC |

FIG. 10P

| | | | | | |
|---|---|---|---|---|---|
| | | | | 14710 | 14720 | 14730 | 14740 | 14750 | 14760 | 14770 |
| CATCACCGCG | AGGCGGTTTT | CTCCGGCGCG | TAAAAATGCG | CTCAGGTCAA | ATTCAGACGG | CAAACGACTG |
| | | | | 14780 | 14790 | 14800 | 14810 | 14820 | 14830 | 14840 |
| TCCTGGCCGT | AACCGACCCA | GCGCCCGTTG | CACCACAGAT | GAAACGCCGA | GTTAACGCCA | TCAAAAATAA |
| | | | | 14850 | 14860 | 14870 | 14880 | 14890 | 14900 | 14910 |
| TTCGCGTCTG | GCCTTCCTGT | AGCCAGCTTT | CATCAACATT | AAATGTGAGC | GAGTAACAAC | CCGTCGGATT |
| | | | | 14920 | 14930 | 14940 | 14950 | 14960 | 14970 | 14980 |
| CTCCGTGGGA | ACAAACGGCG | GATTGACCGT | AATGGGATAG | GTCACGTTGG | TGTAGATGGG | CGCATCGTAA |
| | | | | 14990 | 15000 | 15010 | 15020 | 15030 | 15040 | 15050 |
| CCGTGCATCT | GCCAGTTTGA | GGGGACGACG | ACAGTATCGG | CCTCAGGAAG | ATCGCACTCC | AGCCAGCTTT |
| | | | | 15060 | 15070 | 15080 | 15090 | 15100 | 15110 | 15120 |
| CCGGCACCGC | TTCTGGTGCC | GGAAACCAGG | GCAAGCGCCA | TTCGCCATTC | AGGCTGCGCA | ACTGTTGGGA |
| | | | | 15130 | 15140 | 15150 | 15160 | 15170 | 15180 | 15190 |
| AGGGCGATCG | GTGCGGGCCT | CTTCGCTATT | ACGCCAGCTG | GCGAAAGGGG | GATGTGCTGC | AAGGCGATTA |
| | | | | 15200 | 15210 | 15220 | 15230 | 15240 | 15250 | 15260 |
| AGTTGGGTAA | CGCCAGGGTT | TTCCCAGTCA | CGACGTTGTA | AAACGACTTA | ATCCGTCGAG | GGGCTGCCTC |
| | | | | 15270 | 15280 | 15290 | 15300 | 15310 | 15320 | 15330 |
| GAAGCAGACG | ACCTTCCGTT | GTGCAGCCAG | CGGCGCCTGC | GCCGGTGCCC | ACAATCGTGC | GCGAACAAAC |
| | | | | 15340 | 15350 | 15360 | 15370 | 15380 | 15390 | 15400 |
| TAAACCAGAA | CAAATTATAC | CGGGCGGCACC | GCCGCCACCA | CCTTCTCCCG | TGCCTAACAT | TCCAGCGCCT |
| | | | | 15410 | 15420 | 15430 | 15440 | 15450 | 15460 | 15470 |
| CCACCACCAC | CACCACCATC | GATGTCTGAA | TTGCCGCCG | CTCCACCAAT | GCCGACGGAA | CCTCAACCCG |
| | | | | 15480 | 15490 | 15500 | 15510 | 15520 | 15530 | 15540 |
| CTGCACCTTT | AGACGACAGA | CAACAATTGT | TGGAAGCTAT | TAGAAACGAA | AAAAATCGCA | CTCGTCTCAG |
| | | | | 15550 | 15560 | 15570 | 15580 | 15590 | 15600 | 15610 |
| ACCGGTCAAA | CCAAAAACGG | CGCCCGAAAC | CAGTACAATA | GTTGAGGTGC | CGACTGTGTT | GCCTAAAGAG |
| | | | | 15620 | 15630 | 15640 | 15650 | 15660 | 15670 | 15680 |
| ACATTTGAGC | CTAACCGCC | GTCTGCATCA | CCGCCACCAC | CTCCGGCCTCC | CTCCGCCCCG | CCAGCCCGC |

FIG. 10Q

```
       15690        15700        15710        15720        15730        15740        15750
CTGGCGCCTCC  ACCGATGGTA  GATTTATCAT  CAGCTCCACC  ACCGCCGCCA  TTAGTAGATT  TGCCGTCTGA
              15760        15770        15780        15790        15800        15810        15820
AATGTTACCA   CCGCCTGCAC  CATCGCTTTC  TAACGTGTTG  TCTGAATTAA  AATCGGGCAC  AGTTAGATTG
              15830        15840        15850        15860        15870        15880        15890
AAACCCGCCC   AAAAACGCCC  GCAATCAGAA  ATAATTCCAA  AAAGCTCAAC  TACAAATTTG  ATCGCGGACG
              15900        15910        15920        15930        15940        15950        15960
TGTTAGCCGA   CACAATTAAT  AGGCGTCGTG  TGGCTATGGC  AAAATCGTCT  TCGGAAGCAA  CTTCTAACGA
              15970        15980        15990        16000        16010        16020        16030
CGAGGGTTGG   GACGACGACG  ATAATCGGCC  TAATAAAGCT  AACACGCCCG  ATGTTAAATA  TGTCCAAGCT
              16040        16050        16060        16070        16080        16090        16100
ACTAGTGGTA   CCGCTTGGCA  GAACATATCC  ATCGCGTCCG  CCATCTCCAG  CAGCCGCACG  CGGCGCATCT
              16110        16120        16130        16140        16150        16160        16170
CGGGCAGCGT   TGGGTCCTGG  CCACGGGTGC  GCATGATCGT  GCTCCTGTCG  TTGAGGACCC  GGTAGGCTG
              16180        16190        16200        16210        16220        16230        16240
GCGGGGTTGC   CTTACTGGTT  AGCAGAATGA  ATCACCGATA  CGGAGCGAA   CGTGAAGCGA  CTGCTGCTGC
              16250        16260        16270        16280        16290        16300        16310
AAAACGTCTG   CGACCTGAGC  AACAACATGA  ATGGTCTTCG  GTTTCCGTGT  TTCGTAAAGT  CTGGAAACGC
              16320        16330        16340        16350        16360        16370        16380
GGAAGTCAGC   GCCCTGCACC  ATTATGTTCC  GGATCTGCAT  CGCAGGATGC  TGCTGGCTAC  CCTGTGGAAC
              16390        16400        16410        16420        16430        16440        16450
ACCTACATCT   GTATTAACGA  AGGCGCTGGCA  TTGACCCTGA  CGCAGGATGC  TCTGGTCCCG  CCGCATCCAT
              16460        16470        16480        16490        16500        16510        16520
ACCGCCAGTT   GTTTACCCTC  ACAACGTTCC  AGTAACCGGG  CATGTTCATC  ATCAGTAACC  CGTATCGTGA
              16530        16540        16550        16560        16570        16580        16590
GCATCCCTC    TCGTTTCATC  GGTATCATTA  CCCCCATGAA  CAGAAATCCC  CCTTACACGG  AGGCATCAGT
              16600        16610        16620        16630        16640        16650        16660
GACCAAACAG   GAAAAAACCG  CCCTTAACAT  GGCCCGCTTT  ATCAGAAGCC  AGACATTAAC  GCTTCTGGAG
```

FIG. 10R

| | | | |
|---|---|---|---|
| 16670 | 16680 | 16690 | 16700 | 16710 | 16720 | 16730 |
| AAACTCAACG | AGCTGGACGC | GGATGAACAG | GCAGACATCT | GTGAATCGCT | TCACGACCAC | GCTGATGAGC |
| 16740 | 16750 | 16760 | 16770 | 16780 | 16790 | 16800 |
| TTTACCGCAG | CTGCCTCGCG | CGTTTCGGTG | ATGACGGTGA | AAACCTCTGA | CACATGCAGC | TCCCGGAGAC |
| 16810 | 16820 | 16830 | 16840 | 16850 | 16860 | 16870 |
| GGTCACAGCT | TGTCTGTAAG | CGGATGCCGG | GAGCAGACAA | GCCCGTCAGG | GCGCGTCAGC | GGGTGTTGGC |
| 16880 | 16890 | 16900 | 16910 | 16920 | 16930 | 16940 |
| GGGTGTCGGG | GCGCAGCCAT | GACCCAGTCA | CGTAGCGATA | GCGGAGTGTA | TACTGGCTTA | ACTATGCGGC |
| 16950 | 16960 | 16970 | 16980 | 16990 | 17000 | 17010 |
| ATCAGAGCAG | ATTGTACTGA | GAGTGCACCA | TATGCGGTGT | GAAATACCGC | ACAGATGCGT | AAGGAGAAAA |
| 17020 | 17030 | 17040 | 17050 | 17060 | 17070 | 17080 |
| TACCGCATCA | GGCGCTCTTC | CGCTTCCTCG | CTCACTGACT | CGCTGCGCTC | GGTCGTTCGG | CTGCGGCGAG |
| 17090 | 17100 | 17110 | 17120 | 17130 | 17140 | 17150 |
| CGGTATCAGC | TCACTCAAAG | GCGGTAATAC | GGTTATCCAC | AGAATCAGGG | GATAACGCAG | GAAAGAACAT |
| 17160 | 17170 | 17180 | 17190 | 17200 | 17210 | 17220 |
| GTGAGCAAAA | GGCCAGCAAA | AGGCCAGGAA | CCGTAAAAAG | GCCGCGTTGC | TGGCGTTTT | CCATAGGCTC |
| 17230 | 17240 | 17250 | 17260 | 17270 | 17280 | 17290 |
| CGCCCCCCTG | ACGAGCATCA | CAAAAATCGA | CGGTCAAGTC | AGAGGTGGCG | AAACCCGACA | GGACTATAAA |
| 17300 | 17310 | 17320 | 17330 | 17340 | 17350 | 17360 |
| GATACCAGGC | GTTTCCCCCT | GGAAGCTCCC | TCGTGCGCTC | TCCTGTTCCG | ACCCTGCCGC | TTACCGGATA |
| 17370 | 17380 | 17390 | 17400 | 17410 | 17420 | 17430 |
| CCTGTCCGCC | TTTCTCCCTT | CGGGAAGCGT | GGCGCTTTCT | CATAGCTCAC | GCTGTAGGTA | TCTCAGTTCG |
| 17440 | 17450 | 17460 | 17470 | 17480 | 17490 | 17500 |
| GTGTAGGTCG | TTCGCTCCAA | GCTGGGCTGT | GTGCACGAAC | CCCCCGTTCA | GCCCGACCGC | TGCGCCTTAT |
| 17510 | 17520 | 17530 | 17540 | 17550 | 17560 | 17570 |
| CCGGTAACTA | TCGTCTTGAG | TCCAACCCGG | TAAGACACGA | CTTATCGCCA | CTGGCAGCAG | CCACTGGTAA |
| 17580 | 17590 | 17600 | 17610 | 17620 | 17630 | 17640 |
| CAGGATTAGC | AGAGCGAGGT | ATGTAGGCGG | TGCTACAGAG | TTCTTGAAGT | GGTGGCCTAA | CTACGGCTAC |

FIG. 10S

```
17650              17660              17670              17680              17690              17700              17710
ACTAGAAGGA         CAGTATTTGG         TATCTGCGCT         CTGCTGAAGC         CAGTTACCTT         CGGAAAAAGA         GTTGGTAGCT
         17720              17730              17740              17750              17760              17770              17780
CTTGATCCGG         CAAACAAACC         ACCGCTGGTA         GCGGTGGTTT         TTTGTTTGC          AAGCAGCAGA         TTACGCGCAG
         17790              17800              17810              17820              17830              17840              17850
AAAAAAGGA          TCTCAAGAAG         ATCCTTTGAT         CTTTTCTACG         GGGTCTGACG         CGAAAACTCA
         17860              17870              17880              17890              17900              17910              17920
CGTTAAGGGA         TTTTGGTCAT         GAGATTATCA         AAAAGGATCT         TCACCTAGAT         CCTTTTAAAT         TAAAAATGAA
         17930              17940              17950              17960              17970              17980              17990
GTTTAAATC          AATCTAAAGT         ATATATGAGT         AAACTTGGTC         TGACAGTTAC         CAATGCTTAA         TCAGTGAGGC
         18000              18010              18020              18030              18040              18050              18060
ACCTATCTCA         GCGATCTGTC         TATTTCGTTC         ATCCATAGTT         GCCTGACTCC         CCGTCGTGTA         GATAACTACG
         18070              18080              18090              18100              18110              18120              18130
ATACGGGAGG         GCTTACCATC         TGGCCCCAGT         GCTGCAATGA         TACCGCGAGA         CCCACGCTCA         CCGGCTCCAG
         18140              18150              18160              18170              18180              18190              18200
ATTTATCAGC         AATAAACCAG         CCAGCCGGAA         GGGCCGAGCG         CAGAAGTGGT         CCTGCAACTT         TATCCGCCTC
         18210              18220              18230              18240              18250              18260              18270
CATCCAGTCT         ATTAATTGTT         GCCGGGAAGC         TAGAGTAAGT         AGTTCGCCAG         TTAATAGTTT         GCGCAACGTT
         18280              18290              18300              18310              18320              18330              18340
GTTGCCATTG         CTGCAGGCAT         CGCTCGTCGT         CGTGGTATGG         TTGGTATGGC         TTCATTCAGC         TCCGGTTCCC
         18350              18360              18370              18380              18390              18400              18410
AACGATCAAG         GCGAGTTACA         TGATCCCCCA         TGTTGTGCAA         AAAAGCGGTT         AGCTCCTTCG         GTCCTCCGAT
         18420              18430              18440              18450              18460              18470              18480
CGTGTCAGA          AGTAAGTTGG         CCGCAGTGTT         ATCACTCATG         GTTATGGCAG         CACTGCATAA         TTCTCTTACT
         18490              18500              18510              18520              18530              18540              18550
GTCATGCCAT         CCGTAAGATG         CTTTTCTGTG         ACTGGTGAGT         ACTCAACCAA         GTCATTCTGA         GAATAGTGTA
         18560              18570              18580              18590              18600              18610              18620
TGCGGGGACC         GAGTTGCTCT         TGCCCGGCGT         CAACACGGGA         TAATACCGCG         CCACATAGCA         GAACTTTAAA
```

| | | | | | | | |
|---|---|---|---|---|---|---|---|
| 18630 | 18640 | 18650 | 18660 | 18670 | 18680 | 18690 | |
| AGTGCTCATC | ATTGGAAAAC | GTTCTTCGGG | GCGAAAACTC | TCAAGGATCT | TACCGCTGTT | GAGATCCAGT | |
| 18700 | 18710 | 18720 | 18730 | 18740 | 18750 | 18760 | |
| TCGATGTAAC | CCACTCGTGC | ACCCAACTGA | TCTTCAGCAT | CTTTTACTTT | CACCAGCGTT | TCTGGGTGAG | |
| 18770 | 18780 | 18790 | 18800 | 18810 | 18820 | 18830 | |
| CAAAACAGG | AAGGCAAAAT | GCCGCAAAA | AGGGAATAAG | GGCGACACGG | AAATGTTGAA | TACTCATACT | |
| 18840 | 18850 | 18860 | 18870 | 18880 | 18890 | 18900 | |
| CTTCCTTTT | CAATATTATT | GAAGCATTA | TCAGGGTTAT | TGTCTCATGA | GCGGATACAT | ATTTGAATGT | |
| 18910 | 18920 | 18930 | 18940 | 18950 | 18960 | 18970 | |
| ATTTAGAAAA | ATAAACAAAT | AGGGGTTCCG | CGCACATTTC | CCCGAAAAGT | GCCACCTGAC | GTCTAAGAAA | |
| 18980 | 18990 | 19000 | 19010 | 19020 | 19030 | 19040 | |
| CCATTATTAT | CATGACATTA | ACCTATAAAA | ATAGGCGTAT | CACGAGGCCC | TTTCGTCTTC | AAGAA...... | |
| 19050 | 19060 | 19070 | 19080 | | | | |

METHOD FOR INTEGRATING GENES AT SPECIFIC SITES IN MAMMALIAN CELLS VIA HOMOLOGOUS RECOMBINATION AND VECTORS FOR ACCOMPLISHING THE SAME

RELATED APPLICATIONS

This application is a continuation of U.S. patent application Ser. No. 09/343,485, filed Jun. 30, 1999, now U.S. Pat. No. 6,413,777, which is a continuation of U.S. patent application Ser. No. 09/023,715, filed Feb. 13, 1998, now U.S. Pat. No. 5,998,144, which is a continuation-in-part of U.S. patent application Ser. No. 08/819,866, filed on Mar. 14, 1997, now U.S. Pat. No. 5,830,698.

FIELD OF THE INVENTION

The present invention relates to a process of targeting the integration of a desired exogenous DNA to a specific location within the genome of a mammalian cell. More specifically, the invention describes a novel method for identifying a transcriptionally active target site ("hot spot") in the mammalian genome, and inserting a desired DNA at this site via homologous recombination. The invention also optionally provides the ability for gene amplification of the desired DNA at this location by co-integrating an amplifiable selectable marker, e.g., DHFR, in combination with the exogenous DNA. The invention additionally describes the construction of novel vectors suitable for accomplishing the above, and further provides mammalian cell lines produced by such methods which contain a desired exogenous DNA integrated at a target hot spot.

BACKGROUND

Technology for expressing recombinant proteins in both prokaryotic and eukaryotic organisms is well established. Mammalian cells offer significant advantages over bacteria or yeast for protein production, resulting from their ability to correctly assemble, glycosylate and post-translationally modify recombinantly expressed proteins. After transfection into the host cells, recombinant expression constructs can be maintained as extrachromosomal elements, or may be integrated into the host cell genome. Generation of stably transfected mammalian cell lines usually involves the latter; a DNA construct encoding a gene of interest along with a drug resistance gene (dominant selectable marker) is introduced into the host cell, and subsequent growth in the presence of the drug allows for the selection of cells that have successfully integrated the exogenous DNA. In many instances, the gene of interest is linked to a drug resistant selectable marker which can later be subjected to gene amplification. The gene encoding dihydrofolate reductase (DHFR) is most commonly used for this purpose. Growth of cells in the presence of methotrexate, a competitive inhibitor of DHFR, leads to increased DHFR production by means of amplification of the DHFR gene. As flanking regions of DNA will also become amplified, the resultant coamplification of a DHFR linked gene in the transfected cell line can lead to increased protein production, thereby resulting in high level expression of the gene of interest.

While this approach has proven successful, there are a number of problems with the system because of the random nature of the integration event. These problems exist because expression levels are greatly influenced by the effects of the local genetic environment at the gene locus, a phenomena well documented in the literature and generally referred to as "position effects" (for example, see Al-Shawi et al, Mol. Cell. Biol., 10:1192–1198 (1990); Yoshimura et al, Mol. Cell. Biol., 7:1296–1299 (1987)). As the vast majority of mammalian DNA is in a transcriptionally inactive state, random integration methods offer no control over the transcriptional fate of the integrated DNA. Consequently, wide variations in the expression level of integrated genes can occur, depending on the site of integration. For example, integration of exogenous DNA into inactive, or transcriptionally "silent" regions of the genome will result in little or no expression. By contrast integration into a transcriptionally active site may result in high expression.

Therefore, when the goal of the work is to obtain a high level of gene expression, as is typically the desired outcome of genetic engineering methods, it is generally necessary to screen large numbers of transfectants to find such a high producing clone. Additionally, random integration of exogenous DNA into the genome can in some instances disrupt important cellular genes, resulting in an altered phenotype. These factors can make the generation of high expressing stable mammalian cell lines a complicated and laborious process.

Recently, the use of DNA vectors containing translationally impaired dominant selectable markers in mammalian gene expression has been described. (This is disclosed in co-owned U.S. Ser. No. 08/147,696 filed Nov. 3, 1993, now U.S. Pat. No. 5,736,137).

These vectors contain a translationally impaired neomycin phosphotransferase (neo) gene as the dominant selectable marker, artificially engineered to contain an intron into which a DHFR gene along with a gene or genes of interest is inserted. Use of these vectors as expression constructs has been found to significantly reduce the total number of drug resistant colonies produced, thereby facilitating the screening procedure in relation to conventional mammalian expression vectors. Furthermore, a significant percentage of the clones obtained using this system are high expressing clones. These results are apparently attributable to the modifications made to the neo selectable marker. Due to the translational impairment of the neo gene, transfected cells will not produce enough neo protein to survive drug selection, thereby decreasing the overall number of drug resistant colonies. Additionally, a higher percentage of the surviving clones will contain the expression vector integrated into sites in the genome where basal transcription levels are high, resulting in overproduction of neo, thereby allowing the cells to overcome the impairment of the neo gene. Concomitantly, the genes of interest linked to neo will be subject to similar elevated levels of transcription. This same advantage is also true as a result of the artificial intron created within neo; survival is dependent on the synthesis of a functional neo gene, which is in turn dependent on correct and efficient splicing of the neo introns. Moreover, these criteria are more likely to be met if the vector DNA has integrated into a region which is already highly transcriptionally active.

Following integration of the vector into a transcriptionally active region, gene amplification is performed by selection for the DHFR gene. Using this system, it has been possible to obtain clones selected using low levels of methotrexate (50 nM), containing few (<10) copies of the vector which secrete high levels of protein (>55 pg/cell/day). Furthermore, this can be achieved in a relatively short period of time. However, the success in amplification is variable. Some transcriptionally active sites cannot be amplified and therefore the frequency and extent of amplification from a particular site is not predictable.

Overall, the use of these translationally impaired vectors represents a significant improvement over other methods of random integration. However, as discussed, the problem of lack of control over the integration site remains a significant concern.

One approach to overcome the problems of random integration is by means of gene targeting, whereby the exogenous DNA is directed to a specific locus within the host genome. The exogenous DNA is inserted by means of homologous recombination occurring between sequences of DNA in the expression vector and the corresponding homologous sequence in the genome. However, while this type of recombination occurs at a high frequency naturally in yeast and other fungal organisms, in higher eukaryotic organisms it is an extremely rare event. In mammalian cells, the frequency of homologous versus non-homologous (random integration) recombination is reported to range from $\frac{1}{100}$ to $\frac{1}{5000}$ (for example, see Capecchi, *Science*, 244:1288–1292 (1989); Morrow and Kucherlapati, *Curr. Op. Biotech.*, 4:577–582 (1993)).

One of the earliest reports describing homologous recombination in mammalian cells comprised an artificial system created in mouse fibroblasts (Thomas et al, *Cell*, 44:419–428 (1986)). A cell line containing a mutated, non-functional version of the neo gene integrated into the host genome was created, and subsequently targeted with a second non-functional copy of neo containing a different mutation. Reconstruction of a functional neo gene could occur only by gene targeting. Homologous recombinants were identified by selecting for G418 resistant cells, and confirmed by analysis of genomic DNA isolated from the resistant clones.

Recently, the use of homologous recombination to replace the heavy and light immunoglobulin genes at endogenous loci in antibody secreting cells has been reported. (U.S. Pat. No. 5,202,238, Fell et al, (1993).) However, this particular approach is not widely applicable, because it is limited to the production of immunoglobulins in cells which endogenously express immunoglobulins, e.g., B cells and myeloma cells. Also, expression is limited to single copy gene levels because co-amplification after homologous recombination is not included. The method is further complicated by the fact that two separate integration events are required to produce a functional immunoglobulin: one for the light chain gene followed by one for the heavy chain gene.

An additional example of this type of system has been reported in NS/0 cells, where recombinant immunoglobulins are expressed by homologous recombination into the immunoglobulin gamma 2A locus (Hollis et al, international patent application # PCT/IB95 (00014).) Expression levels obtained from this site were extremely high—on the order of 20 pg/cell/day from a single copy integrant. However, as in the above example, expression is limited to this level because an amplifiable gene is not contegrated in this system. Also, other researchers have reported aberrant glycosylation of recombinant proteins expressed in NS/0 cells (for example, see Flesher et al, *Biotech. and Bioeng.*, 48:399–407 (1995)), thereby limiting the applicability of this approach.

The cre-loxP recombination system from bacteriophage P1 has recently been adapted and used as a means of gene targeting in eukaryotic cells. Specifically, the site specific integration of exogenous DNA into the Chinese hamster ovary (CHO) cell genome using cre recombinase and a series of lox containing vectors have been described. (Fukushige and Sauer, *Proc. Natl. Acad. Sci. USA*, 89:7905–7909 (1992).) This system is attractive in that it provides for reproducible expression at the same chromosomal location. However, no effort was made to identify a chromosomal site from which gene expression is optimal, and as in the above example, expression is limited to single copy levels in this system. Also, it is complicated by the fact that one needs to provide for expression of a functional recombinase enzyme in the mammalian cell.

The use of homologous recombination between an introduced DNA sequence and its endogenous chromosomal locus has also been reported to provide a useful means of genetic manipulation in mammalian cells, as well as in yeast cells. (See e.g., Bradley et al, *Meth. Enzymol.*, 223:855–879 (1993); Capecchi, *Science*, 244:1288–1292 (1989); Rothstein et al, *Meth. Enzymol.*, 194:281–301 (1991)). To date, most mammalian gene targeting studies have been directed toward gene disruption ("knockout") or site-specific mutagenesis of selected target gene loci in mouse embryonic stem (ES) cells. The creation of these "knockout" mouse models has enabled scientists to examine specific structure-function issues and examine the biological importance of a myriad of mouse genes. This field of research also has important implications in terms of potential gene therapy applications.

Also, vectors have recently been reported by Cell-tech (Kent, U.K.) which purportedly are targeted to transcriptionally active sites in NSO cells, which do not require gene amplification (Peakman et al, *Hum. Antibod. Hybridomas*, 5:65–74 (1994)). However, levels of immunoglobulin secretion in these unamplified cells have not been reported to exceed 20 pg/cell/day, while in amplified CHO cells, levels as high as 100 pg/cell/day can be obtained (Id.).

It would be highly desirable to develop a gene targeting system which reproducibly provided for the integration of exogenous DNA into a predetermined site in the genome known to be transcriptionally active. Also, it would be desirable if such a gene targeting system would further facilitate co-amplification of the inserted DNA after integration. The design of such a system would allow for the reproducible and high level expression of any cloned gene of interest in a mammalian cell, and undoubtedly would be of significant interest to many researchers.

In this application, we provide a novel mammalian expression system, based on homologous recombination occurring between two artificial substrates contained in two different vectors. Specifically, this system uses a combination of two novel mammalian expression vectors, referred to as a "marking" vector and a "targeting" vector.

Essentially, the marking vector enables the identification and marking of a site in the mammalian genome which is transcriptionally active, i.e., a site at which gene expression levels are high. This site can be regarded as a "hot spot" in the genome. After integration of the marking vector, the subject expression system enables another DNA to be integrated at this site, i.e., the targeting vector, by means of homologous recombination occurring between DNA sequences common to both vectors. This system affords significant advantages over other homologous recombination systems.

Unlike most other homologous systems employed in mammalian cells, this system exhibits no background. Therefore, cells which have only undergone random integration of the vector do not survive the selection. Thus, any gene of interest cloned into the targeting plasmid is expressed at high levels from the marked hot spot. Accordingly, the subject method of gene expression substantially or completely eliminates the problems inherent to systems of random integration, discussed in detail above. Moreover, this system provides reproducible and high level expression of any recombinant protein at the same transcriptionally active site in the mammalian genome. In addition, gene amplification may be effected at this particular transcriptionally active site by including an amplifiable dominant selectable marker (e.g. DHFR) as part of the marking vector.

OBJECTS OF THE INVENTION

Thus, it is an object of the invention to provide an improved method for targeting a desired DNA to a specific site in a mammalian cell.

It is a more specific object of the invention to provide a novel method for targeting a desired DNA to a specific site in a mammalian cell via homologous recombination.

It is another specific object of the invention to provide novel vectors for achieving site specific integration of a desired DNA in a mammalian cell.

It is still another object of the invention to provide novel mammalian cell lines which contain a desired DNA integrated at a predetermined site which provides for high expression.

It is a more specific object of the invention to provide a novel method for achieving site specific integration of a desired DNA in a Chinese hamster ovary (CHO) cell.

It is another more specific object of the invention to provide a novel method for integrating immunoglobulin genes, or any other genes, in mammalian cells at predetermined chromosomal sites that provide for high expression.

It is another specific object of the invention to provide novel vectors and vector combinations suitable for integrating immunoglobulin genes into mammalian cells at predetermined sites that provide for high expression.

It is another object of the invention to provide mammalian cell lines which contain immunoglobulin genes integrated at predetermined sites that provide for high expression.

It is an even more specific object of the invention to provide a novel method for integrating immunoglobulin genes into CHO cells that provide for high expression, as well as novel vectors and vector combinations that provide for such integration of immunoglobulin genes into CHO cells.

In addition, it is a specific object of the invention to provide novel CHO cell lines which contain immunoglobulin genes integrated at predetermined sites that provide for high expression, and have been amplified by methotrexate selection to secrete even greater amounts of functional immunoglobulins.

BRIEF DESCRIPTION OF THE FIGURES

FIG. 2(a) shows a map of a targeting plasmid referred to "Molly". Molly is shown here encoding the anti-CD20 immunoglobulin genes, expression of which is described in Example 1.

Lane 1: λHindIII DNA size marker
Lane 2: Desmond clone 10F3
Lane 3: Desmond clone 10C12
Lane 4: Desmond clone 15C9
Lane 4: Desmond clone 14B5
Lane 6: Desmond clone 9B2

Figure 5:
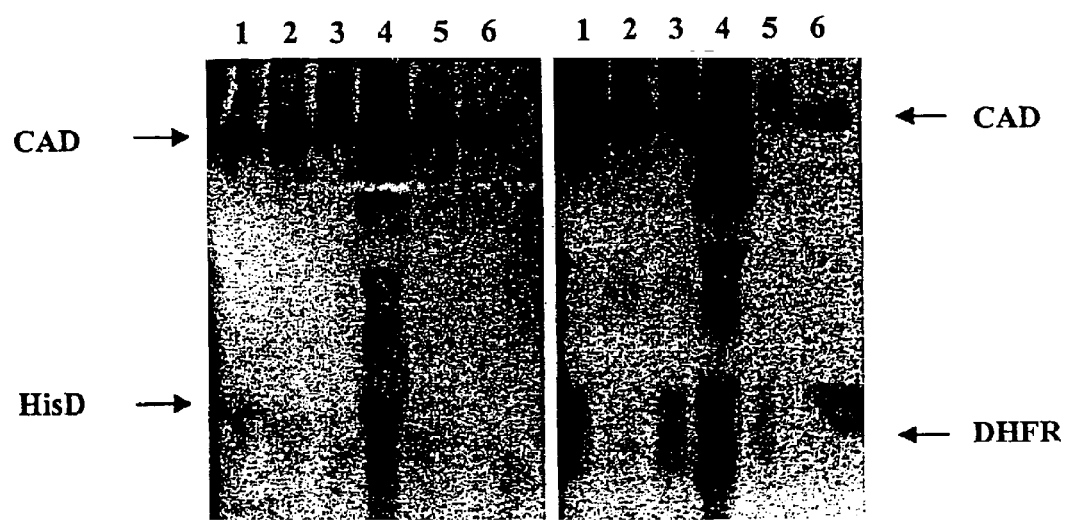

FIG. 5 shows a Northern analysis of single copy Desmond clones. Samples are as follows: Panel A: northern probed with CAD and DHFR probes, as indicated on the figure. Panel B: duplicate northern, probed with CAD and HisD probes, as indicated. The RNA samples loaded in panels A and B are as follows:

Lane 1: clone 9B2, lane 2; clone 10C12, lane 3; clone 14B5, lane 4; clone 15C9, lane 5; control RNA from CHO transfected with a HisD and DHFR containing plasmid, lane 6; untransfected CHO.

Figure 6:
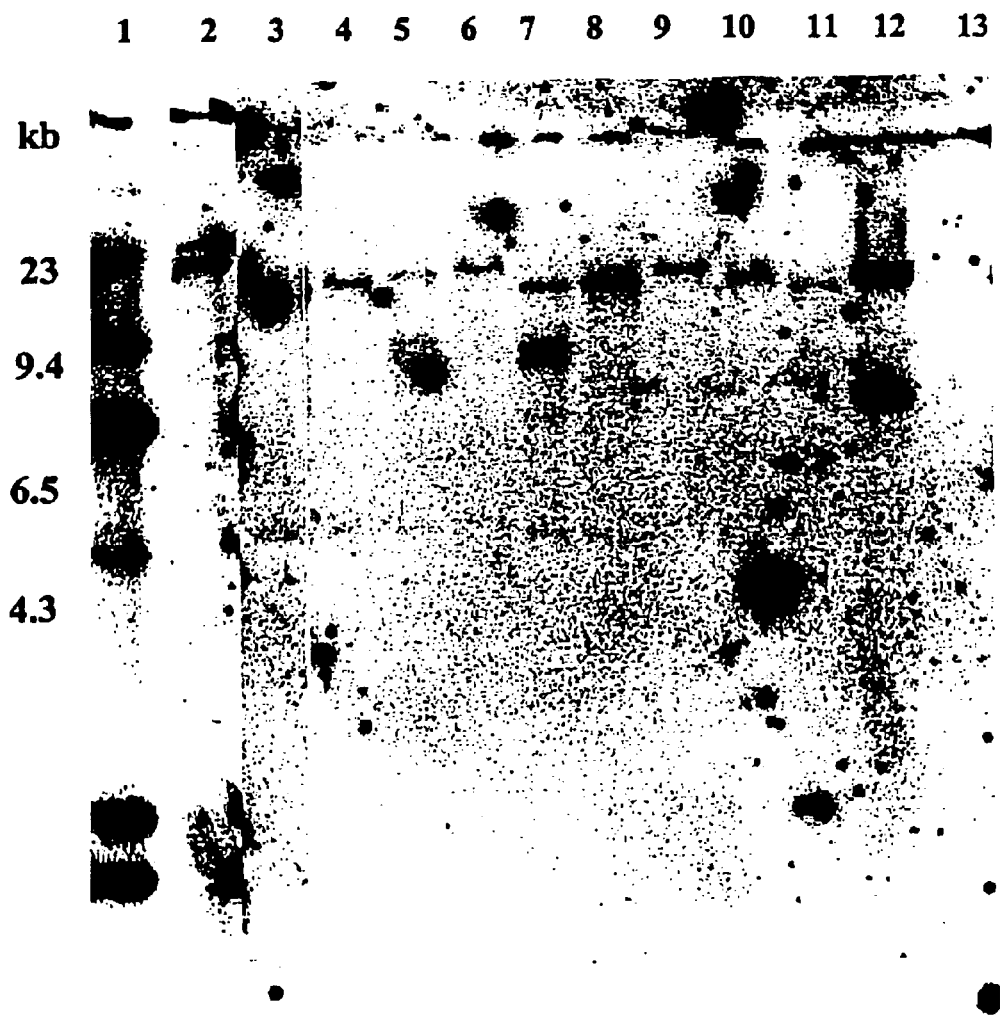

FIG. 6 shows a Southern analysis of clones resulting from the homologous integration of Molly into Desmond. Samples are as follows:

Lane 1: λHindIII DNA size markers, Lane 2: 20F4, lane 3; 5F9, lane 4; 21C7, lane 5; 24G2, lane 6; 25E1, lane 7; 28C 9, lane 8; 29F 9, lane 9; 39G11, lane 10; 42F9, lane 11; 50G10, lane 12; Molly plasmid DNA, linearized with BglII(top band) and cut with BglII and KpnI (lower band), lane 13; untransfected Desmond.

FIGS. 7A through 7G and 7P–7X (SEQ ID NO:1) contain the nucleic acid sequence of Desmond.

FIGS. 8A through 8N and 8P–8X (SEQ ID NO:2) contain the nucleic acid sequence of Molly-containing anti-CD20.

FIG. 9 contains a map of the targeting plasmid, "Mandy," shown here encoding anti-CD23 genes, the expression of which is disclosed in Example 5.

FIGS. 10A through 10N and 10P–10U (SEQ ID NO:3) contain the nucleic acid sequence of "Mandy" containing the anti-CD23 genes as disclose in Example 5.

DETAILED DESCRIPTION OF THE INVENTION

The invention provides a novel method for integrating a desired exogenous DNA at a target site within the genome of a mammalian cell via homologous recombination. Also, the invention provides novel vectors for achieving the site specific integration of a DNA at a target site in the genome of a mammalian cell.

More specifically, the subject cloning method provides for site specific integration of a desired DNA in a mammalian cell by transfection of such cell with a "marker plasmid" which contains a unique sequence that is foreign to the mammalian cell genome and which provides a substrate for homologous recombination, followed by transfection with a "target plasmid" containing a sequence which provides for homologous recombination with the unique sequence contained in the marker plasmid, and further comprising a desired DNA that is to be integrated into the mammalian cell. Typically, the integrated DNA will encode a protein of interest, such as an immunoglobulin or other secreted mammalian glycoprotein.

The exemplified homologous recombination system uses the neomycin phosphotransferase gene as a dominant selectable marker. This particular marker was utilized based on the following previously published observations;

(i) the demonstrated ability to target and restore function to a mutated version of the neo gene (cited earlier) and (ii) our development of translationally impaired expression vectors, in which the neo gene has been artificially created as two exons with a gene of interest inserted in the intervening intron; neo exons are correctly spliced and translated in vivo, producing a functional protein and thereby conferring G418 resistance on the resultant cell population. In this application, the neo gene is split into three exons. The third exon of neo is present on the "marker" plasmid and becomes integrated into the host cell genome upon integration of the marker plasmid into the mammalian cells. Exons 1 and 2 are present on the targeting plasmid, and are separated by an intervening intron into which at least one gene of interest is cloned. Homologous recombination of the targeting vector with the integrated marking vector results in correct splicing of all three exons of the neo gene and thereby expression of a functional neo protein (as determined by selection for G418 resistant colonies). Prior to designing the current expression system, we had experimentally tested the functionality of such a triply spliced neo construct in mammalian cells. The results of this control experiment indicated that all three neo exons were properly spliced and therefore suggested the feasibility of the subject invention.

However, while the present invention is exemplified using the neo gene, and more specifically a triple split neo gene, the general methodology should be efficacious with other dominant selectable markers.

As discussed in greater detail infra, the present invention affords numerous advantages to conventional gene expression methods, including both random integration and gene targeting methods. Specifically, the subject invention provides a method which reproducibly allows for site-specific integration of a desired DNA into a transcriptionally active domain of a mammalian cell. Moreover, because the subject method introduces an artificial region of "homology" which acts as a unique substrate for homologous recombination and the insertion of a desired DNA, the efficacy of subject invention does not require that the cell endogenously contain or express a specific DNA. Thus, the method is generically applicable to all mammalian cells, and can be used to express any type of recombinant protein.

The use of a triply spliced selectable marker, e.g., the exemplified triply spliced neo construct, guarantees that all G418 resistant colonies produced will arise from a homologous recombination event (random integrants will not produce a functional neo gene and consequently will not survive G418 selection). Thus, the subject invention makes it easy to screen for the desired homologous event. Furthermore, the frequency of additional random integrations in a cell that has undergone a homologous recombination event appears to be low.

Based on the foregoing, it is apparent that a significant advantage of the invention is that it substantially reduces the number of colonies that need be screened to identify high producer clones, i.e., cell lines containing a desired DNA which secrete the corresponding protein at high levels. On average, clones containing integrated desired DNA may be identified by screening about 5 to 20 colonies (compared to several thousand which must be screened when using standard random integration techniques, or several hundred using the previously described intronic insertion vectors) Additionally, as the site of integration was preselected and comprises a transcriptionally active domain, all exogenous DNA expressed at this site should produce comparable, i.e. high levels of the protein of interest.

Moreover, the subject invention is further advantageous in that it enables an amplifiable gene to be inserted on integration of the marking vector. Thus, when a desired gene is targeted to this site via homologous recombination, the subject invention allows for expression of the gene to be further enhanced by gene amplification. In this regard, it has been reported in from the literature that different genomic sites have different capacities for gene amplification (Meinkoth et al, *Mol. Cell Biol.*, 7:1415–1424 (1987). Therefore, this technique is further advantageous as it allows for the placement of a desired gene of interest at a specific site that is both transcriptionally active and easily amplified. Therefore, this should significantly reduce the amount of time required to isolate such high producers.

Specifically, while conventional methods for the construction of high expressing mammalian cell lines can take 6 to 9 months, the present invention allows for such clones to be isolated on average after only about 3–6 months. This is due to the fact that conventionally isolated clones typically must be subjected to at least three rounds of drug resistant gene amplification in order to reach satisfactory levels of gene expression. As the homologously produced clones are generated from a preselected site which is a high expression site, fewer rounds of amplification should be required before reaching a satisfactory level of production.

Still further, the subject invention enables the reproducible selection of high producer clones wherein the vector is integrated at low copy number, typically single copy. This is advantageous as it enhances the stability of the clones and avoids other potential adverse side-effects associated with high copy number. As described supra, the subject homologous recombination system uses the combination of a "marker plasmid" and a "targeting plasmid" which are described in more detail below.

The "marker plasmid" which is used to mark and identify a transcriptionally hot spot will comprise at least the following sequences:

(i) a region of DNA that is heterologous or unique to the genome of the mammalian cell, which functions as a source of homology, allows for homologous recombination (with a DNA contained in a second target plasmid). More specifically, the unique region of DNA (i) will generally comprise a bacterial, viral, yeast synthetic, or other DNA which is not normally present in the mammalian cell genome and which further does not comprise significant homology or sequence identity to DNA contained in the genome of the mammalian cell. Essentially, this sequence should be sufficiently different to mammalian DNA that it will not significantly recombine with the host cell genome via homologous recombination. The size of such unique DNA will generally be at least about 2 to 10 kilobases in size, or higher, more preferably at least about 10 kb, as several other investigators have noted an increased frequency of targeted recombination as the size of the homology region is increased (Capecchi, *Science,* 244:1288–1292 (1989).

The upper size limit of the unique DNA which acts as a site for homologous recombination with a sequence in the second target vector is largely dictated by potential stability constraints (if DNA is too large it may not be easily integrated into a chromosome and the difficulties in working with very large DNAs.

(ii) a DNA including a fragment of a selectable marker DNA, typically an exon of a dominant selectable marker gene. The only essential feature of this DNA is that it not encode a functional selectable marker protein unless it is expressed in association with a sequence contained in the target plasmid. Typically, the target plasmid will comprise the remaining exons of the dominant selectable marker gene (those not comprised in "targeting" plasmid). Essentially, a functional selectable marker should only be produced if homologous recombination occurs (resulting in the association and expression of this marker DNA (i) sequence together with the portion(s) of the selectable marker DNA fragment which is (are) contained in the target plasmid).

As noted, the current invention exemplifies the use of the neomycin phosphotransferase gene as the dominant selectable marker which is "split" in the two vectors. However, other selectable markers should also be suitable, e.g., the *Salmonella* histidinol dehydrogenase gene, hygromycin phosphotransferase gene, *herpes simplex* virus thymidine kinase gene, adenosine deaminase gene, glutamine synthetase gene and hypoxanthine-guanine phosphoribosyl transferase gene.

(iii) a DNA which encodes a functional selectable marker protein, which selectable marker is different from the selectable marker DNA (ii). This selectable marker provides for the successful selection of mammalian cells wherein the marker plasmid is successfully integrated into the cellular DNA. More preferably, it is desirable that the marker plasmid comprise two such dominant selectable marker DNAs, situated at opposite ends of the vector. This is advantageous as it enables integrants to be selected using different selection agents and further enables cells which contain the entire vector to be selected. Additionally, one marker can be an amplifiable marker to facilitate gene amplification as discussed previously. Any of the dominant selectable marker listed in (ii) can be used as well as others generally known in the art.

Moreover, the marker plasmid may optionally further comprise a rare endonuclease restriction site. This is potentially desirable as this may facilitate cleavage. If present, such rare restriction site should be situated close to the middle of the unique region that acts as a substrate for homologous recombination. Preferably such sequence will be at least about 12 nucleotides. The introduction of a double stranded break by similar methodology has been reported to enhance the frequency of homologous recombination. (Choulika et al, *Mol. Cell. Biol.*, 15:1968–1973 (1995). However, the presence of such sequence is not essential.

The "targeting plasmid" will comprise at least the following sequences:

(1) the same unique region of DNA contained in the marker plasmid or one having sufficient homology or sequence identity therewith that said DNA is capable of combining via homologous recombination with the unique region (i) in the marker plasmid. Suitable types of DNAs are described supra in the description of the unique region of DNA (1) in the marker plasmid.

(2) The remaining exons of the dominant selectable marker, one exon of which is included as (ii) in the marker plasmid listed above. The essential features of this DNA fragment is that it result in a functional (selectable) marker protein only if the target plasmid integrates via homologous recombination (wherein such recombination results in the association of this DNA with the other fragment of the selectable marker DNA contained in the marker plasmid) and further that it allow for insertion of a desired exogenous DNA. Typically, this DNA will comprise the remaining exons of the selectable marker DNA which are separated by an intron. For example, this DNA may comprise the first two exons of the neo gene and the marker plasmid may comprise the third exon (back third of neo).

(3) The target plasmid will also comprise a desired DNA, e.g., one encoding a desired polypeptide, preferably inserted within the selectable marker DNA fragment contained in the plasmid. Typically, the DNA will be inserted in an intron which is comprised between the exons of the selectable marker DNA. This ensures that the desired DNA is also integrated if homologous recombination of the target plasmid and the marker plasmid occurs. This intron may be naturally occurring or it may be engineered into the dominant selectable marker DNA fragment.

This DNA will encode any desired protein, preferably one having pharmaceutical or other desirable properties. Most typically the DNA will encode a mammalian protein, and in the current examples provided, an immunoglobulin or an immunoadhesin. However the invention is not in any way limited to the production of immunoglobulins.

As discussed previously, the subject cloning method is suitable for any mammalian cell as it does not require for efficacy that any specific mammalian sequence or sequences be present. In general, such mammalian cells will comprise those typically used for protein expression, e.g., CHO cells, myeloma cells, COS cells, BHK cells, Sp2/0 cells, NIH 3T3 and HeLa cells. In the examples which follow, CHO cells were utilized. The advantages thereof include the availability of suitable growth medium, their ability to grow efficiently and to high density in culture, and their ability to express mammalian proteins such as immunoglobulins in biologically active form.

Further, CHO cells were selected in large part because of previous usage of such cells by the inventors for the expression of immunoglobulins (using the translationally impaired dominant selectable marker containing vectors described previously). Thus, the present laboratory has considerable experience in using such cells for expression. However, based on the examples which follow, it is reasonable to expect similar results will be obtained with other mammalian cells.

In general, transformation or transfection of mammalian cells according to the subject invention will be effected according to conventional methods. So that the invention may be better understood, the construction of exemplary vectors and their usage in producing integrants is described in the examples below.

EXAMPLE 1

Design and Preparation of Marker and Targeting Plasmid DNA Vectors

The marker plasmid herein referred to as "Desmond" was assembled from the following DNA elements:

(a) Murine dihydrofolate reductase gene (DHFR), incorporated into a transcription cassette, comprising the mouse beta globin promoter 5" to the DHFR start site, and bovine growth hormone poly adenylation signal 3" to the stop codon. The DHFR transcriptional cassette was isolated from TCAE6, an expression vector created previously in this laboratory (Newman et al, 1992, *Biotechnology*, 10:1455–1460).

(b) *E. coli* β-galactosidase gene—commercially available, obtained from Promega as pSV-b-galactosidase control vector, catalog # E1081.

(c) Baculovirus DNA, commercially available, purchased from Clontech as pBAKPAK8, cat # 6145-1.

(d) Cassette comprising promoter and enhancer elements from Cytomegalovirus and SV40 virus. The cassette was generated by PCR using a derivative of expression vector TCAE8 (Reff et al, *Blood*, 83:435–445 (1994)). The enhancer cassette was inserted within the baculovirus sequence, which was first modified by the insertion of a multiple cloning site.

(e) *E. coli* GUS (glucuronidase) gene, commercially available, purchased from Clontech as pB101, cat. # 6017-1.

(f) Firefly luciferase gene, commercially available, obtained from Promega as pGEM-Luc (catalog # E1541 ).

(g) *S. typhimurium* histidinol dehydrogenase gene (HisD). This gene was originally a gift from (Donahue et el, *Gene*, 18:47–59 (1982)), and has subsequently been incorporated into a transcription cassette comprising the mouse beta globin major promoter 5' to the gene, and the SV40 polyadenylation signal 3' to the gene.

The DNA elements described in (a)–(g) were combined into a pBR derived plasmid backbone to produce a 7.7 kb contiguous stretch of DNA referred to in the attached figures as "homology". Homology in this sense refers to sequences of DNA which are not part of the mammalian genome and are used to promote homologous recombination between transfected plasmids sharing the same homology DNA sequences.

(h) Neomycin phosphotransferase gene from TN5 (Davis and Smith, *Ann. Rev. Micro.*, 32:469–518 (1978)). The complete neo gene was subcloned into pBluescript SK- (Stratagene catalog # 212205) to facilitate genetic manipulation. A synthetic linker was then inserted into a unique Pst1 site occurring across the codons for amino acid 51 and 52 of neo. This linker encoded the necessary DNA elements to create an artificial splice donor site, intervening intron and splice acceptor site within the neo gene, thus creating two separate exons, presently referred to as neo exon 1 and 2. Neo exon 1 encodes the first 51 amino acids of neo, while exon 2 encodes the remaining 203 amino acids plus the stop codon of the protein A Not1 cloning site was also created within the intron.

Neo exon 2 was further subdivided to produce neo exons 2 and 3. This was achieved as follows: A set of PCR primers were designed to amplify a region of DNA encoding neo exon 1, intron and the first 111 $\frac{2}{3}$ amino acids of exon2. The 3' PCR primer resulted in the introduction of a new 5' splice site immediately after the second nucleotide of the codon for amino acid 111 in exon 2, therefore generating a new smaller exon 2. The DNA fragment now encoding the original exon 1, intron and new exon 2 was then subcloned and propagated in a pBR based vector. The remainder of the original exon 2 was used as a template for another round of PCR amplification, which generated "exon3". The 5' primer for this round of amplification introduced a new splice acceptor site at the 5' side of the newly created exon 3, i.e. before the final nucleotide of the codon for amino acid 111. The resultant 3 exons of neo encode the following information: exon 1—the first 51 amino acids of neo; exon 2—the next 111 $\frac{2}{3}$ amino acids, and exon 3 the final 91 $\frac{1}{3}$ amino acids plus the translational stop codon of the neo gene.

Neo exon 3 was incorporated along with the above mentioned DNA elements into the marking plasmid "Desmond". Neo exons 1 and 2 were incorporated into the targeting plasmid "Molly". The Not1 cloning site created within the intron between exons 1 and 2 was used in subsequent cloning steps to insert genes of interest into the targeting plasmid.

A second targeting plasmid "Mandy" was also generated. This plasmid is almost identical to "Molly" (some restriction sites on the vector have been changed) except that the original HisD and DHFR genes contained in "Molly" were inactivated. These changes were incorporated because the Desmond cell line was no longer being cultured in the presence of Histidinol, therefore it seemed unnecessary to include a second copy of the HisD gene. Additionally, the DHFR gene was inactivated to ensure that only a single DHFR gene, namely the one present in the Desmond marked site, would be amplifiable in any resulting cell lines. "Mandy" was derived from "Molly" by the following modifications:

(i) A synthetic linker was inserted in the middle of the DHFR coding region. This linker created a stop codon and shifted the remainder of the DHFR coding region out of frame, therefore rendering the gene nonfunctional.

(ii) A portion of the HisD gene was deleted and replaced with a PCR generated HisD fragment lacking the promoter and start codon of the gene.

Figure 1A:
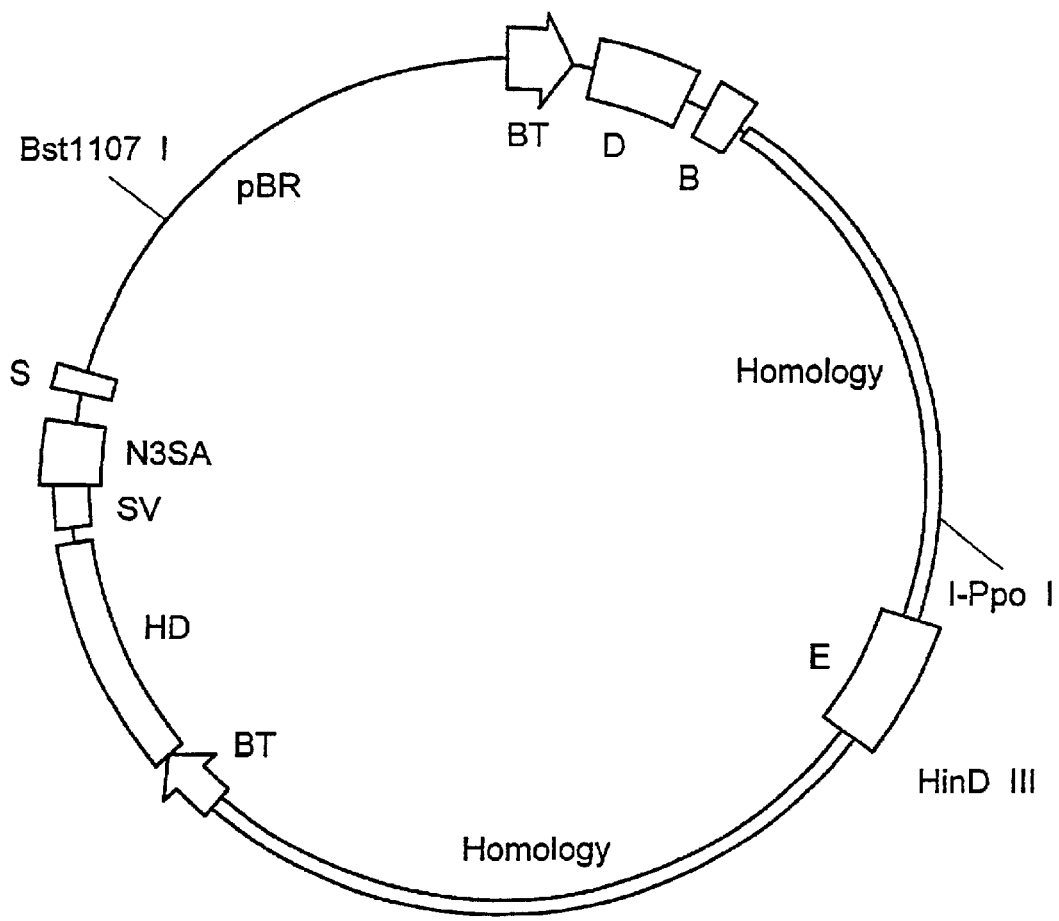
FIG. 1 depicts a map of a marking plasmid according to the invention referred to as Desmond. The plasmid is shown in circular form (1a) as well as a linearized version used for transfection (1b).
Figure 1B:
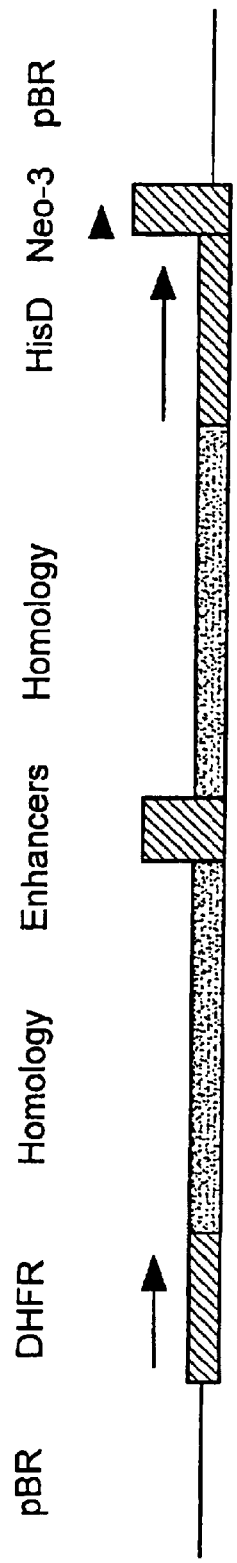
Figure 2B:
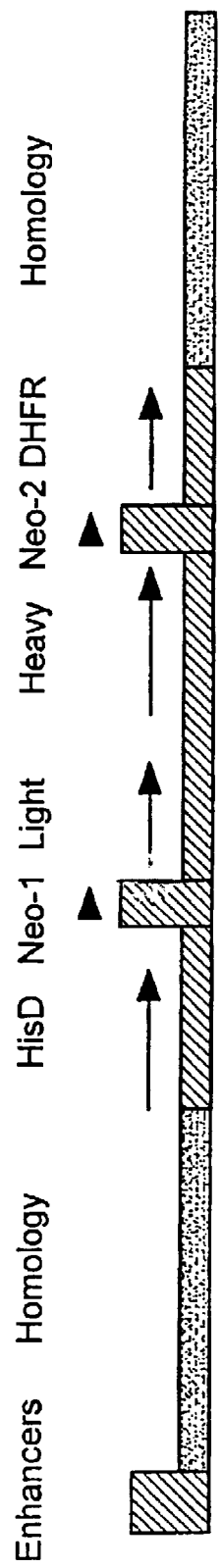
FIG. 2(b) shows a linearized version of Molly, after digestion with the restriction enzymes Kpn1and Pac1. This linearized form was used for transfection.
Figure 3:
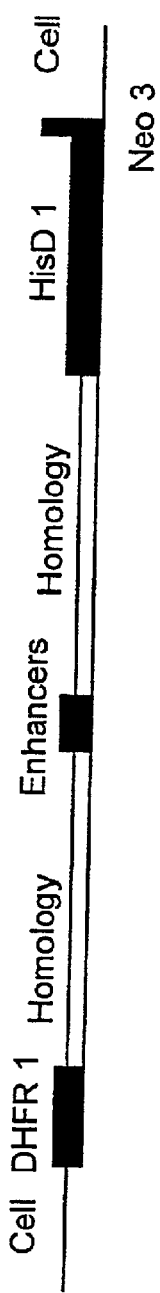
FIG. 3 depicts the potential alignment between Desmond sequences integrated into the CHO genome, and incoming targeting Molly sequences. One potential arrangement of Molly integrated into Desmond after homologous recombination is also presented.
Figure 3:
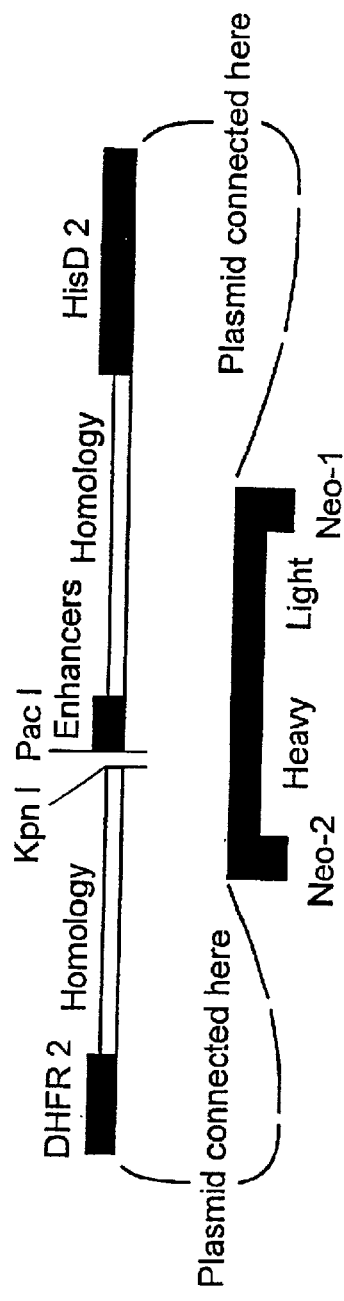
Figure 3:
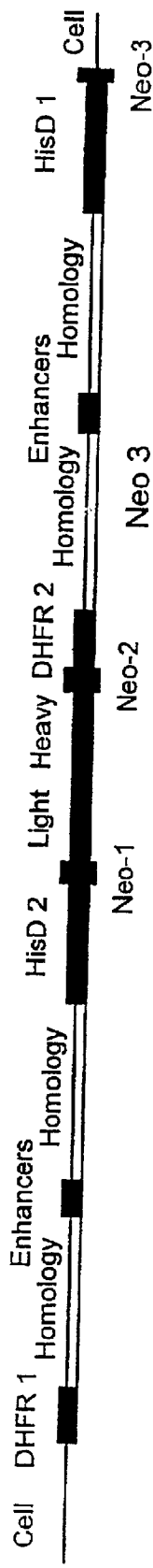

FIG. 1 depicts the arrangement of these DNA elements in the marker plasmid "Desmond". FIG. 2 depicts the arrangement of these elements in the first targeting plasmid, "Molly". FIG. 3 illustrates the possible arrangement in the CHO genome, of the various DNA elements after targeting and integration of Molly DNA into Desmond marked CHO cells. FIG. 9 depicts the targeting plasmid "Mandy."

Construction of the marking and targeting plasmids from the above listed DNA elements was carried out following conventional cloning techniques (see, e.g., Molecular Cloning, A Laboratory Manual, J. Sambrook et al, 1987, Cold Spring Harbor Laboratory Press, and Current Protocols in Molecular Biology, F. M. Ausubel et al, eds., 1987, John Wiley and Sons). All plasmids were propagated and maintained in *E. coli* XLI blue (Stratagene, cat. # 200236). Large scale plasmid preparations were prepared using Promega Wizard Maxiprep DNA Purification System ®, according to the manufacturer's directions.

EXAMPLE 2

Construction of a Marked CHO Cell Line

1. Cell Culture and Transfection Procedures to Produced Marked CHO Cell Line

Marker plasmid DNA was linearized by digestion overnight at 37° C. with Bst1107I. Linearized vector was ethanol precipitated and resuspended in sterile TE to a concentration of 1 mg/ml. Linearized vector was introduced into DHFR-Chinese hamster ovary cells (CHO cells) DG44 cells (Urlaub et al, *Som. Cell and Mol. Gen.*, 12:555–566 (1986)) by electroporation as follows.

Exponentially growing cells were harvested by centrifugation, washed once in ice cold SBS (sucrose buffered solution, 272 mM sucrose, 7 mM sodium phosphate, ph 7.4, 1 mM magnesium chloride) then resuspended in SBS to a concentration of $10^7$ cells/ml. After a 15 minute incubation on ice, 0.4 ml of the cell suspension was mixed with 40 µg linearized DNA in a disposable electroporation cuvette. Cells were shocked using a BTX electrocell manipulator (San Diego, Calif.) set at 230 volts, 400 microfaraday capacitance, 13 ohm resistance. Shocked cells were then mixed with 20 ml of prewarmed CHO growth media (CHO-S-SFMII, Gibco/BRL, catalog # 31033-012) and plated in 96 well tissue culture plates. Forty eight hours after electroporation, plates were fed with selection media (in the case of transfection with Desmond, selection media is CHO-S-SFMII without hypoxanthine or thymidine, supplemented with 2 mM Histidinol (Sigma catalog # H6647)). Plates were maintained in selection media for up to 30 days, or until some of the wells exhibited cell growth. These cells were then removed from the 96 well plates and expanded ultimately to 120 ml spinner flasks where they were maintained in selection media at all times.

EXAMPLE 3

Characterization of Marked CHO Cell Lines
(a) Southern Analysis

Figure 4:
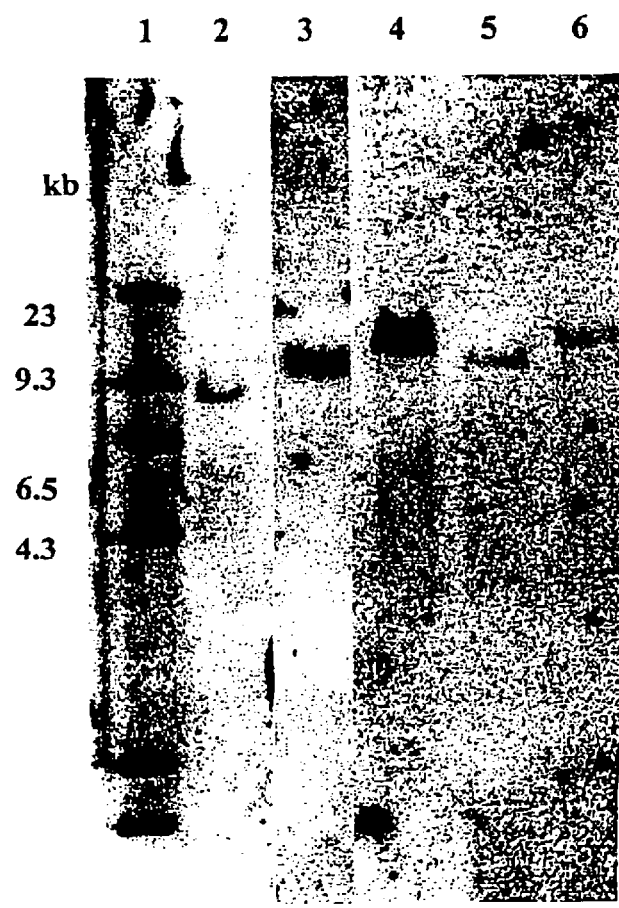
FIG. 4 shows a Southern analysis of single copy Desmond clones. Samples are as follows.

Genomic DNA was isolated from all stably growing Desmond marked CHO cells. DNA was isolated using the Invitrogen Easy ® DNA kit, according to the manufacturer's directions. Genomic DNA was then digested with HindIII overnight at 37° C., and subjected to Southern analysis using a PCR generated digoxygenin labelled probe specific to the DHFR gene. Hybridizations and washes were carried out using Boehringer Mannheim's DIG easy hyb (catalog # 1603 558) and DIG Wash and Block Buffer Set (catalog # 1585 762) according to the manufacturer's directions. DNA samples containing a single band hybridizing to the DHFR probe were assumed to be Desmond clones arising from a single cell which had integrated a single copy of the plasmid. These clones were retained for further analysis. Out of a total of 45 HisD resistant cell lines isolated, only 5 were single copy integrants. FIG. 4 shows a Southern blot containing all 5 of these single copy Desmond clones. Clone names are provided in the figure legend.
(b) Northern Analysis Total RNA was isolated from all single copy Desmond clones using TRIzol reagent (Gibco/BRL cat # 15596-026) according to the manufacturer's directions. 10–20 µg RNA from each clone was analyzed on duplicate formaldehyde gels. The resulting blots were probed with PCR generated digoxygenin labelled DNA probes to (i) DHFR message, (ii) HisD message and (iii) CAD message. CAD is a trifunctional protein involved in uridine biosynthesis (Wahl et al, *J. Biol. Chem.*, 254, 17:8679–8689 (1979)), and is expressed equally in all cell types. It is used here as an internal control to help quantitate RNA loading. Hybridizations and washes were carried out using the above mentioned Boehringer Mannheim reagents. The results of the Northern analysis are shown in FIG. 5. The single copy Desmond clone exhibiting the highest levels of both the His D and DHFR message is clone 15C9, shown in lane 4 in both panels of the figure. This clone was designated as the "marked cell line" and used in future targeting experiments in CHO, examples of which are presented in the following sections.

EXAMPLE 4

Expression of Anti-CD20 Antibody in Desmond Marked CHO Cells

C2B8, a chimeric antibody which recognizes B-cell surface antigen CD20, has been cloned and expressed previously. (Reff et al, *Blood*, 83:435–445 (1994)). A 4.1 kb DNA fragment comprising the C2B8 light and heavy chain genes, along with the necessary regulatory elements (eukaryotic promoter and polyadenylation signals) was inserted into the artificial intron created between exons 1 and 2 of the neo gene contained in a pBR derived cloning vector. This newly generated 5 kb fragment (comprising neo exon 1, C2B8 and neo exon 2) was excised and used to assemble the targeting plasmid Molly. The other DNA elements used in the construction of Molly are identical to those used to construct the marketing plasmid Desmond, identified previously. A complete map of Molly is shown in FIG. 2.

The targeting vector Molly was linearized prior to transfection by digestion with Kpn1 and Pac1, ethanol precipitated and resuspended in sterile TE to a concentration of 1.5 mg/mL. Linearized plasmid was introduced into exponentially growing Desmond marked cells essentially as described, except that 80 µg DNA was used in each electroporation. Forty eight hours postelectroporation, 96 well plates were supplemented with selection medium—CHO-SSFMII supplemented with 400 µg/mL Geneticin (G418, Gibco/BRL catalog # 10131-019). Plates were maintained in selection medium for up to 30 days, or until cell growth occurred in some of the wells. Such growth was assumed to be the result of clonal expansion of a single G418 resistant cell. The supernatants from all G418 resistant wells were assayed for C2B8 production by standard ELISA techniques, and all productive clones were eventually expanded to 120 mL spinner flasks and further analyzed.

Characterization of Antibody Secreting Targeted Cells

A total of 50 electroporations with Molly targeting plasmid were carried out in this experiment, each of which was plated into separate 96 well plates. A total of 10 viable, anti-CD20 antibody secreting clones were obtained and expanded to 120 ml spinner flasks. Genomic DNA was isolated from all clones, and Southern analyses were subsequently performed to determine whether the clones represented single homologous recombination events or whether additional random integrations had occurred in the same cells. The methods for DNA isolation and Southern hybridization were as described in the previous section. Genomic DNA was digested with EcoRI and probed with a PCR generated digoxygenin labelled probe to a segment of the CD20 heavy chain constant region. The results of this Southern analysis are presented in FIG. 6. As can be seen in the figure, 8 of the 10 clones show a single band hybridizing to the CD20 probe, indicating a single homologous recombination event has occurred in these cells. Two of the ten, clones 24G2 and 28C9, show the presence of additional band(s), indicative of an additional random integration elsewhere in the genome.

We examined the expression levels of anti-CD20 antibody in all ten of these clones, the data for which is shown in Table 1, below.

TABLE 1

Expression Level of Anti-CD20
Secreting Homologous Integrants

| Clone | Anti-CD20, pg/c/d |
| --- | --- |
| 20F4 | 3.5 |
| 25E1 | 2.4 |
| 42F9 | 1.8 |
| 39G11 | 1.5 |
| 21C7 | 1.3 |
| 50G10 | 0.9 |
| 29F9 | 0.8 |
| 5F9 | 0.3 |
| 28C9* | 4.5 |
| 24G2* | 2.1 |

*These clones contained additional randomly integrated copies of anti-CD20. Expression levels of these clones therefore reflect a contribution from both the homologous and random sites.

Expression levels are reported as picogram per cell per day (pg/c/d) secreted by the individual clones, and represented the mean levels obtained from three separate ELISAs on samples taken from 120 mL spinner flasks.

As can be seen from the data, there is a variation in antibody secretion of approximately ten fold between the highest and lowest clones. This was somewhat unexpected as we anticipated similar expression levels from all clones due to the fact the anti-CD20 genes are all integrated into the same Desmond marked site. Nevertheless, this observed range in expression extremely small in comparison to that seen using any traditional random integration method or with our translationally impaired vector system.

Clone 20F4, the highest producing single copy integrant was selected for further study. Table 2 (below) presents ELISA and cell culture data from seven day production runs of this clone.

TABLE 2

7 Day Production Run Data for 20F4

| Day | % Viable | Viable/ml (× $10^5$) | T × 2 (hr) | mg/L | pg/c/d |
|---|---|---|---|---|---|
| 1 | 96 | 3.4 | 31 | 1.3 | 4.9 |
| 2 | 94 | 6 | 29 | 2.5 | 3.4 |
| 3 | 94 | 9.9 | 33 | 4.7 | 3.2 |
| 4 | 90 | 17.4 | 30 | 6.8 | 3 |
| 5 | 73 | 14 | | 8.3 | |
| 6 | 17 | 3.5 | | 9.5 | |

Clone 20F4 was seeded at 2 × $10^5$ ml in a 120 ml spinner flask on day 0. On the following six days, cell counts were taken, doubling times calculated and 1 ml samples of supernatant removed from the flask and analyzed for secreted anti-CD20 by ELISA.

This clone is secreting on average, 3–5 pg antibody/cell/day, based on this ELISA data. This is the same level as obtained from other high expressing single copy clones obtained previously in our laboratory using the previously developed translationally impaired random integration vectors. This result indicates the following:

(1) that the site in the CHO genome marked by the Desmond marking vector is highly transcriptionally active, and therefore represents an excellent site from which to express recombinant proteins, and (2) that targeting by means of homologous recombination can be accomplished using the subject vectors and occurs at a frequency high enough to make this system a viable and desirable alternative to random integration methods.

To further demonstrate the efficacy of this system, we have also demonstrated that this site is amplifiable, resulting in even higher levels of gene expression and protein secretion. Amplification was achieved by plating serial dilutions of 20F4 cells, starting at a density of 2.5×$10^4$ cells/ml, in 96 well tissue culture dishes, and culturing these cells in media (CHO-SSFMII) supplemented with 5, 10, 15 or 20 nM methotrexate. Antibody secreting clones were screened using standard ELISA techniques, and the highest producing clones were expanded and further analyzed. A summary of this amplification experiment is presented in Table 3 below.

TABLE 3

Summary of 20F4 Amplification

| nM MTX | # Wells Assayed | Expression Level mg/l 96 well | # Wells Expanded | Expression Level pg/c/d from spinner |
|---|---|---|---|---|
| 10 | 56 | 3–13 | 4 | 10–15 |
| 15 | 27 | 2–14 | 3 | 15–18 |
| 20 | 17 | 4–11 | 1 | ND |

Methotrexate amplification of 20F4 was set up as described in the text, using the concentrations of methotrexate indicated in the above table. Supernatants from all surviving 96 well colonies were assayed by ELISA, and the range of anti-CD20 expressed by these clones is indicated in column 3. Based on these results, the highest producing clones were expanded to 120 ml spinners and several ELISAs conducted on the spinner supernatants to determine the pg/cell/day expression levels, reported in column 5.

The data here clearly demonstrates that this site can be amplified in the presence of methotrexate. Clones from the 10 and 5nM amplifications were found to produce on the order of 15–20 pg/cell/day.

A 15 nM clone, designated 20F4-15A5, was selected as the highest expressing cell line. This clone originated from a 96 well plate in which only 22 wells grew, and was therefore assumed to have arisen from a single cell. A 15 nM clone, designated 20F4-15A5, was selected as the highest expressing cell line. This clone originated from a 96 well plate in which only 22 wells grew, and was therefore assumed to have arisen from a single cell. The clone was then subjected to a further round of methotrexate amplification. As described above, serial dilutions of the culture were plated into 96 well dishes and cultured in CHO-SS-FMII medium supplemented with 200, 300 or 400 nM methotrexate. Surviving clones were screened by ELISA, and several high producing clones were expanded to spinner cultures and further analyzed. A summary of this second amplification experiment is presented in Table 4.

TABLE 4

Summary of 20F4-15A5 Amplification

| nM MTX | # Wells Assayed | Expression Level mg/l 96 well | # Wells Expanded | Expression Level pg/c/d from spinner |
|---|---|---|---|---|
| 200 | 67 | 23–70 | 1 | 50–60 |
| 250 | 86 | 21–70 | 4 | 55–60 |
| 300 | 81 | 15–75 | 3 | 40–50 |

Methotrexate amplifications of 20F4-15A5 were set up and assayed as described in the text. The highest producing wells, the numbers of which are indicated in column 4, were expanded to 120 ml spinner flasks. The expression levels of the cell lines derived from these wells is recorded as pg/c/d in column 5.

The highest producing clone came from the 250 nM methotrexate amplification. The 250 nM clone, 20F4-15A5-250A6 originated from a 96 well plate in which only wells grew, and therefore is assumed to have arisen from a single cell. Taken together, the data in Tables 3 and 4 strongly indicates that two rounds of methotrexate amplification are sufficient to reach expression levels of 60 pg/cell/day, which is approaching the maximum secretion capacity of immunoglobulin in mammalian cells (Reff, M. E., Curr. Opin. Biotech., 4:573–576 (1993)). The ability to reach this secretion capacity with just two amplification steps further enhances the utility of this homologous recombination system. Typically, random integration methods require more than two amplification steps to reach this expression level and are generally less reliable in terms of the ease of amplification. Thus, the homologous system offers a more efficient and time saving method of achieving high level gene expression in mammalian cells.

EXAMPLE 5

Expression of Anti-Human CD23 Antibody in Desmond Marked CHO Cells

CD23 is low affinity IgE receptor which mediates binding of IgE to B and T lymphocytes (Sutton, B. J., and Gould, H. J., Nature, 366:421–428 (1993)). Anti-human CD23 monoclonal antibody 5E8 is a human gamma-1 monoclonal antibody recently cloned and expressed in our laboratory. This antibody is disclosed in commonly assigned Ser. No. 08/803,085, filed on Feb. 20, 1997.

The heavy and light chain genes of 5E8 were cloned into the mammalian expression vector N5KG1, a derivative of the vector NEOSPLA (Barnett et al, in *Antibody Expression and Engineering*, H. Y Yang and T. Imanaka, eds., pp 27–40

(1995)) and two modifications were then made to the genes. We have recently observed somewhat higher secretion of immunoglobulin light chains compared to heavy chains in other expression constructs in the laboratory (Reff et al, 1997, unpublished observations). In an attempt to compensate for this deficit, we altered the 5E8 heavy chain gene by the addition of a stronger promoter/enhancer element immediately upstream of the start site. In subsequent steps, a 2.9 kb DNA fragment comprising the 5E8 modified light and heavy chain genes was isolated from the N5KG1 vector and inserted into the targeting vector Mandy. Preparation of 5E8-containing Molly and electroporation into Desmond 15C9 CHO cells was essentially as described in the preceding section.

One modification to the previously described protocol was in the type of culture medium used. Desmond marked CHO cells were cultured in protein-free CD-CHO medium (Gibco-BRL, catalog # AS21206) supplemented with 3 mg/L recombinant insulin (3 mg/mL stock, Gibco-BRL, catalog # AS22057) and 8mM L-glutamine (200 mM stock, Gibco-BRL, catalog # 25030-081). Subsequently, transfected cells were selected in the above medium supplemented with 400 µg/mL Geneticin. In this experiment, 20 electroporations were performed and plated into 96 well tissue culture dishes. Cells grew and secreted anti-CD23 in a total of 68 wells, all of which were assumed to be clones originating from a single G418 cell. Twelve of these wells were expanded to 120 ml spinner flasks for further analysis. We believe the increased number of clones isolated in this experiment (68 compared with 10 for anti-CD20 as described in Example 4) is due to a higher cloning efficiency and survival rate of cells grown in CD-CHO medium compared with CHO-SS-FMII medium. Expression levels for those clones analyzed in spinner culture ranged from 0.5–3 pg/c/d, in close agreement with the levels seen for the anti-CD20 clones. The highest producing anti-CD23 clone, designated 4H12, was subjected to methotrexate amplification in order to increase its expression levels. This amplification was set up in a manner similar to that described for the anti-CD20 clone in Example 4. Serial dilutions of exponentially growing 4H12 cells were plated into 96 well tissue culture dishes and grown in CD-CHO medium supplemented with 3 mg/L insulin, 8 mM glutamine and 30, 35 or 40 nM methotrexate. A summary of this amplification experiment is presented in Table 5.

TABLE 5

Summary of 2H12 Amplification

| nM MTX | # Wells Assayed | Expression Level mg/l 96 well | # Wells Expanded | Expression Level pg/c/d from spinner |
|---|---|---|---|---|
| 30 | 100 | 6–24 | 8 | 10–25 |
| 35 | 64 | 4–27 | 2 | 10–15 |
| 40 | 96 | 4–20 | 1 | ND |

The highest expressing clone obtained was a 30 nM clone, isolated from a plate on which 22 wells had grown. This clone, designated 4H12-30G5, was reproducibly secreting 18–22 pg antibody per cell per day. This is the same range of expression seen for the first amplification of the anti CD20 clone 20F4 (clone 20F4-15A5 which produced 15–18 pg/c/d, as described in Example 4). This data serves to further support the observation that amplification at this marked site in CHO is reproducible and efficient. A second amplification of this 30 nM cell line is currently underway. It is anticipated that saturation levels of expression will be achievable for the anti-CD23 antibody in just two amplification steps, as was the case for anti-CD20.

EXAMPLE 6

Expression of Immunoadhesin in Desmond Marked CHO Cells

CTLA-4, a member of the Ig superfamily, is found on the surface of T lymphocytes and is thought to play a role in antigen-specific T-cell activation (Dariavach et al, *Eur. J. Immunol.*, 18:1901–1905 (1988)); and Linsley et al, *J. Exp. Med.*, 174:561–569 (1991)). In order to further study the precise role of the CTLA-4 molecule in the activation pathway, a soluble fusion protein comprising the extracellular domain of CTLA-4 linked to a truncated form of the human IgG1 constant region was created (Linsley et al (Id.). We have recently expressed this CTLA-4 Ig fusion protein in the mammalian expression vector BLECH1, a derivative of the plasmid NEOSPLA (Barnett et al, in Antibody Expression and Engineering, H. Y Yang and T. Imanaka, eds., pp27–40 (1995)). An 800 bp fragment encoding the CTLA-4 Ig was isolated from this vector and inserted between the SacII and BglII sites in Molly.

Preparation of CTLA-4Ig-Molly and electroporation into Desmond clone 15C9 CHO cells was performed as described in the previous example relating to anti-CD20. Twenty electroporations were carried out, and plated into 96 well culture dishes as described previously. Eighteen CTLA-4 expressing wells were isolated from the 96 well plates and carried forward to the 120 ml spinner stage. Southern analyses on genomic DNA isolated from each of these clones were then carried out to determine how many of the homologous clones contained additional random integrants. Genomic DNA was digested with BglII and probed with a PCR generated digoxygenin labelled probe to the human IgG1 constant region. The results of this analysis indicated that 85% of the CTLA-4 clones are homologous integrants only; the remaining 15% contained one additional random integrant. This result corroborates the findings from the expression of anti-CD20 discussed above, where 80% of the clones were single homologous integrants. Therefore, we can conclude that this expression system reproducibly yields single targeted homologous integrants in at least 80% of all clones produced.

Expression levels for the homologous CTlA4-Ig clones ranged from 8–12 pg/cell/day. This is somewhat higher than the range reported for anti-CD20 antibody and anti-CD23 antibody clones discussed above. However, we have previously observed that expression of this molecule using the intronic insertion vector system also resulted in significantly higher expression levels than are obtained for immunoglobulins. We are currently unable to provide an explanation for this observation.

EXAMPLE 7

Targeting Anti-CD20 to an Alternate Desmond Marked CHO Cell Line

As we described in a preceding section, we obtained 5 single copy Desmond marked CHO cell lines (see FIGS. 4 and 5). In order to demonstrate that the success of our targeting strategy is not due to some unique property of Desmond clone 15C9 and limited only to this clone, we introduced anti-CD20 Molly into Desmond clone 9B2 (lane 6 in FIG. 4, lane 1 in FIG. 5). Preparation of Molly DNA and electroporation into Desmond 9B2 was exactly as described in the previous example pertaining to anti-CD20. We obtained one homologous integrant from this experiment. This clone was expanded to a 120 ml spinner flask, where it produced on average 1.2 pg anti-CD20/cell/day. This is considerably lower expression than we observed with Molly targeted into Desmond 15C9. However, this was the anticipated result, based on our northern analysis of the Desmond clones. As can be seen in FIG. 5, mRNA levels from clone 9B2 are considerably lower than those from 15C9, indicating the site in this clone is not as transcriptionally active as that in 15C9. Therefore, this experiment not only demonstrates the reproducibility of the system—presumably any marked Desmond site can be targeted with Molly—it also confirms the northern data that the site in Desmond 15C9 is the most transcriptionally active.

From the foregoing, it will be appreciated that, although specific embodiments of the invention have been described herein for purposes of illustration, various modifications may be made without diverting from the scope of the invention. Accordingly, the invention is not limited by the appended claims.

What is claimed is:

1. A targeting vector referred to as Molly for achieving integration of desired gene(s) in a host cell that comprises the gene map shown schematically in FIG. 2(a), except that said vector optionally may lack the anti-CD20 antibody genes identified in the figure as K, VH, VL and G1.

2. The vector of claim 1 which contains genes that provide for the expression of an antibody.

3. The vector of claim 2 wherein said antibody is a chimeric antibody.

4. The vector of claim 3 wherein said chimeric antibody is a chimeric anti-CD20 antibody.

5. The targeting vector of claim 1 which comprises the vector nucleic acid sequence of SEQ ID NO:2.

6. A marker vector referred to as Desmond for achieving integration of desired gene(s) in a host cell having the gene map shown schematically in FIG. 1(a).

7. The marker vector of claim 6 which comprises the vector nucleic acid sequence of SEQ ID NO:1.

8. A targeting vector referred to as Mandy for achieving integration of desired genes in a host cell having the gene map shown schematically in FIG. 9, with the proviso that said vector may optionally lack the anti-CD23 antibody genes identified in the figure as K, VL, VH and G1.

9. The targeting vector of claim 8 comprising vector nucleic acid sequence of SEQ ID NO:3.

10. The targeting vector of claim 8 containing genes that encode for an antibody.

11. The targeting vector of claim 10 wherein said antibody is a chimeric antibody.

12. The targeting vector of claim 11 wherein said chimeric antibody is a chimeric anti-CD23 antibody.

13. A host cell containing a vector according to any one of claims 1–12.

14. The host cell of claim 13 which is a mammalian cell.

15. The host cell of claim 14 which is selected from the group consisting of CHO, myeloma, CoS, BHK, Sp 2/0, NIH 3T3 and HeLa cells.

16. The host cell of claim 15 which is a CHO cell.

* * * * *

SEQUENCE LISTING

<160> NUMBER OF SEQ ID NOS: 3

<210> SEQ ID NO 1
<211> LENGTH: 14683
<212> TYPE: DNA
<213> ORGANISM: Artificial Sequence
<220> FEATURE:
<223> OTHER INFORMATION: Description of Artificial Sequence: Synthetic
      DNA referred to as "Desmond"

<400> SEQUENCE: 1

| | | | | | |
|---|---|---|---|---|---|
| tttctagacc | tagggcggcc | agctagtagc | tttgcttctc | aatttcttat | ttgcataatg | 60 |
| agaaaaaaag | gaaaattaat | tttaacacca | attcagtagt | tgattgagca | aatgcgttgc | 120 |
| caaaaggat | gctttagaga | cagtgttctc | tgcacagata | aggacaaaca | ttattcagag | 180 |
| ggagtaccca | gagctgagac | tcctaagcca | gtgagtggca | cagcattcta | gggagaaata | 240 |
| tgcttgtcat | caccgaagcc | tgattccgta | gagccacacc | ttggtaaggg | ccaatctgct | 300 |
| cacacaggat | agagagggca | ggagccaggg | cagagcatat | aaggtgaggt | aggatcagtt | 360 |
| gctcctcaca | tttgcttctg | acatagttgt | gttgggagct | tggatagctt | ggacagctca | 420 |
| gggctgcgat | ttcgcgccaa | acttgacggc | aatcctagcg | tgaaggctgg | taggatttta | 480 |
| tccccgctgc | catcatggtt | cgaccattga | actgcatcgt | cgccgtgtcc | caaaatatgg | 540 |
| ggattggcaa | gaacggagac | ctaccctggc | ctccgctcag | gaacgagttc | aagtacttcc | 600 |
| aaagaatgac | cacaacctct | tcagtggaag | gtaaacagaa | tctggtgatt | atgggtagga | 660 |
| aaacctggtt | ctccattcct | gagaagaatc | gacctttaaa | ggacagaatt | aatatagttc | 720 |
| tcagtagaga | actcaaagaa | ccaccacgag | gagctcattt | tcttgccaaa | agtttggatg | 780 |
| atgccttaag | acttattgaa | caaccggaat | tggcaagtaa | agtagacatg | gtttggatag | 840 |
| tcggaggcag | ttctgtttac | caggaagcca | tgaatcaacc | aggccacctt | agactctttg | 900 |
| tgacaaggat | catgcaggaa | tttgaaagtg | acacgttttt | cccagaaatt | gatttgggga | 960 |
| aatataaact | tctcccagaa | tacccaggcg | tcctctctga | ggtccaggag | gaaaaaggca | 1020 |
| tcaagtataa | gtttgaagtc | tacgagaaga | aagactaaca | ggaagatgct | ttcaagttct | 1080 |
| ctgctccect | cctaaagcta | tgcatttta | taagaccatg | ggacttttgc | tggctttaga | 1140 |
| tcagcctcga | ctgtgccttc | tagttgccag | ccatctgttg | tttgcccctc | cccgtgcct | 1200 |
| tccttgaccc | tggaaggtgc | cactcccact | gtcctttcct | aataaaatga | ggaaattgca | 1260 |
| tcgcattgtc | tgagtaggtg | tcattctatt | ctgggggtg | gggtggggca | ggacagcaag | 1320 |
| ggggaggatt | gggaagacaa | tagcaggcat | gctggggatg | cggtgggctc | tatggaacca | 1380 |
| gctgggctc | gaagcggccg | cccatttcgc | tggtggtcag | atgcgggatg | gcgtgggacg | 1440 |
| cggcggggac | cgtcacactg | aggttttccg | ccagacgcca | ctgctgccag | gcgctgatgt | 1500 |
| gcccggcttc | tgaccatgcg | gtcgcgttcg | gttgcactac | gcgtactgtg | agccagagtt | 1560 |
| gcccggcgct | ctccggctgc | ggtagttcag | gcagttcaat | caactgttta | ccttgtggag | 1620 |
| cgacatccag | aggcacttca | ccgcttgcta | gcggcttacc | atccagcgcc | accatccagt | 1680 |
| gcaggagctc | gttatcgcta | tgacggaaca | ggtattcgct | ggtcacttcg | atggtttgcc | 1740 |

-continued

```
cggataaacg gaactggaaa aactgctgct ggtgttttgc ttccgtcagc gctggatgcg      1800
gcgtgcggtc ggcaaagacc agaccgttca tacagaactg cgatcgttc ggcgtatcac       1860 caaaatcacc gccgtaagcc gaccacgggt tgccgttttc atcatattta atcagcgact      1920
gatccaccca gtcccagacg aagccgccct gtaaacgggg atactgacga aacgcctgcc      1980
agtatttagc gaaaccgcca agactgttac ccatcgcgtg ggcgtattcg caaaggatca     2040
gcgggcgcgt ctctccgggt agcgaaagcc attttttgat ggaccatttc ggaccagccg    2100
ggaagggctg gtcttcatcc acgcgcgcgt acatcgggca aataatatcg gtggccgtgg   2160
tgtcggctcc gccgccttca tactgcaccg ggcgggaagg atcgacagat ttgatccagc    2220
gatacagcgc gtcgtgatta gcgccgtggc ctgattcatt ccccagcgac cagatgatca   2280
cactcgggtg attacgatcg cgctgcacca ttcgcgttac gcgttcgctc atcgccgta     2340 gccagcgcgg atcatcggtc agacgattca ttggcaccat gccgtgggtt tcaatattgg   2400
cttcatccac cacatacagg ccgtagcggt cgcacagcgt gtaccacagc ggatggttcg   2460
gataatgcga acagcgcacg gcgttaaagt tgttctgctt catcagcagg atatcctgca    2520
ccatcgtctg ctcatccatg acctgaccat gcagaggatg atgctcgtga cggttaacgc  2580
ctcgaatcag caacggcttg ccgttcagca gcagcagacc atttccaatc cgcacctcgc   2640
ggaaaccgac atcgcaggct tctgcttcaa tcagcgtgcc gtcggcggtg tgcagttcaa  2700
ccaccgcacg atagagattc gggatttcgg cgctccacag tttcgggttt tcgacgttca  2760
gacgcagtgt gacgcgatcg gcataaccac caggctcatc gataatttca ccgccgaaag  2820
gcgcggtgcc gctggcgacc tgcgtttcac cctgccataa agaaactgtt acccgtaggt  2880
agtcacgcaa ctcgccgcac atctgaactt cagcctccag tacagcgcgg ctgaaatcat   2940
cattaaagcg agtggcaaca tggaaatcgc tgatttgtgt agtcggttta tgcagcaacg  3000
agacgtcacg gaaaatgccg ctcatccgcc acatatcctg atcttccaga taactgccgt   3060
cactccaacg cagcaccatc accgcgaggc ggttttctcc ggcgcgtaaa aatgcgctca   3120
ggtcaaattc agacggcaaa cgactgtcct ggctgtaacc gacccacgcc ccgttgcacc   3180
acagatgaaa cgccgagtta acgccatcaa aaataattcg cgtctggcct tcctgtagcc  3240
agctttcatc aacattaaat gtgagcgagt aacaacccgt cggattctcc gtgggaacaa   3300
acggcggatt gaccgtaatg ggataggtta cgttggtgta gatgggcgca tcgtaaccgt   3360
gcatctgcca gtttgagggg acgacgacag tatcggcctc aggaagatcg cactccagcc  3420
agctttccgg cactgcttct ggtgccggaa accaggcaaa cgccattcg ccattcaggc    3480 tgcgcaactg ttgggaaggg cgatcggtgc gggcctcttc gctattacgc cagctggcga  3540
aagcgggatg tgctgcaagg cgattaagtt gggtaacgcc agggttttcc cagtcacgac  3600
gttgtaaaac gacttaatcc gtcgaggggc tgcctcgaag cagacgacct tccgttgtgc  3660
agccagcggc gcctgcgccg gtgcccacaa tcgtgcgcga acaaactaaa ccagaacaaa  3720
tcataccggc ggcaccgccg ccaccacctt ctcctgtgcc taacattcca gcgcctccac  3780
cactaccacc accatcgatg tctgaattgc cgcccgctcc accaatgccg acggaacctc  3840
aacccgctgc acctttagac gacagacaac aattgttgga agctattaga aacgaaaaaa  3900
atcgcactcg tctcagaccg gctctcttaa ggtagctcaa accaaaaacg cgcccgaaa   3960 ccagtacaat agttgaggtg ccgactgtgt tgcctaaaga gacatttgag cttaaaccgc    4020
cgtctgcacc accgccacca cctccgcctc cgctccgcc gccagcccg cctgcgcctc     4080 caccgatggt agattcatca tcagctccac caccgccgcc attagtagat ttgccgtctg   4140
```

```
aaatgttacc accgcctgca ccatcgcttt ctaacgtgtt gtctgaatta aaatcgggca   4200
cagttagatt gaaacccgcc caaaaacgcc cgcaatcaga ataattccaa aaaagctcaa   4260
ctacaaattt gatcgcggac gtgttagccg acacaattaa taggcgtcgt gtggctatgg   4320
caaaatcgtc ttcggaagca acttctaacg acgagggttg ggacgacgac gataatcggc   4380
ctaataaagc taacacgccc gatgttaaat atgtccaagc tactagtggt accttaatta   4440
aggggcggag aatgggcgga actgggcgga gttagggcg ggatgggcgg agttagggc    4500
gggactatgt tgctgactaa attgagatgc atgctttgca tacttctgcc tgctggggag    4560
cctgggact ttccacacct ggttgctgac taattgagat gcatgctttg catacttctg    4620
cctgctgggg agcctgggga cttttccacac cctaactgac acacattcca cagaattaat   4680
tccctagtt attaatagta atcaattacg gggtcattag ttcatagccc atatatggag    4740
ttccgcgtta cataacttac ggtaaatggc ccgcctggct gaccgctcaa cgaccccgc    4800
ccattgacgt caataatgac gtatgttccc atagtaacgc caatagggac tttccattga    4860
cgtcaatggg tggactattt acggtaaact gcccacttgg cagtacatca agtgtatcat   4920
atgccaagta cgccccctat tgacgtcaat gacggtaaat ggcccgcctg gcattatgcc   4980
cagtacatga ccttatggga ctttcctact tggcagtaca tctacgtatt agtcatcgct   5040
attaccatgg tgatgcggtt ttggcagtac atcaatgggc gtggatagcg gtttgactca   5100
cggggatttc caagtctcca cccccattgac gtcaatggga gtttgttttg aagcttggcc   5160
ggccatataa acgcggcca gctttatta acgtgtttac gtcgagtcaa ttgtacacta   5220
acgacagtga tgaaagaaat acaaaagcgc ataatatttt gaacgacgtc gaacctttat   5280
tacaaaacaa aacacaaacg aatatcgaca aagctagatt gctgctacaa gatttggcaa   5340
gttttgtggc gttgagcgaa atccattag atagtccagc catcggttcg gaaaaacaac   5400
ccttgtttga aactaatcga aacctatttt acaaatctat tgaggattta atatttaaat   5460
tcagatataa agacgctgaa atcatttga ttttcgctct aacataccac cctaaagatt    5520
ataaatttaa tgaattatta aaatacatca gcaactatat attgatagac atttccagtt    5580
tgtgatatta gtttgtgcgt ctcattacaa tggctgttat ttttaacaac aaacaactgc   5640
tcgcagacaa tagtatagaa aagggaggtg aactgttttt gtttaacggt tcgtacaaca   5700
ttttggaaag ttatgttaat ccggtgctgc taaaaaatgg tgtaattgaa ctagaagaag   5760
ctgcgtacta tgccggcaac atattgtaca aaaccgacga tcccaaattc attgattata   5820
taaatttaat aattaaagca acacactccg aagaactacc agaaaatagc actgttgtaa   5880
attacagaaa aactatgcgc agcggtacta tacaccccat taaaaaagac atatatattt   5940
atgacaacaa aaaatttact ctatacgata gatacatata tggatacgat aataactatg   6000
ttaatttta tgaggagaaa aatgaaaaag agaaggaata cgaagaagaa gacgacaagg   6060
cgtctagttt atgtgaaaat aaaattatat tgtcgcaaat taactgtgaa tcatttgaaa    6120
atgattttaa atattacctc agcgattata actacgcgtt tcaattata gataacacta    6180
caaatgttct tgttgcgttt ggtttgtatc gttaataaaa aacaaattta gcatttataa   6240
ttgttttatt attcaataat tacaaatagg attgagaccc ttgcagttgc cagcaaacgg   6300
acagagcttg tcgaggagag ttgttgattc attgtttgcc tccctgctgc ggttttttgac   6360
cgaagttcat gccagtccag cgttttttgca gcagaaaagc cgccgacttc ggtttgcggt   6420
cgcgagtgaa gatcccttc ttgttaccgc caacgcgcaa tatgccttgc gaggtcgcaa   6480
```

```
aatcggcgaa attccatacc tgttcaccga cgacggcgct gacgcgatca aagacgcggt  6540
gatacatatc cagccatgca cactgatact cttcactcca catgtcggtg tacattgagt  6600
gcagcccggc taacgtatcc acgccgtatt cggtgatgat aatcggctga tgcagtttct  6660
cctgccaggc cagaagttct ttttccagta ccttctctgc cgtttccaaa tcgccgcttt  6720
ggacatacca tccgtaataa cggttcaggc acagcacatc aaagagatcg ctgatggtat  6780
cggtgtgagc gtcgcagaac attacattga cgcaggtgat cggacgcgtc gggtcgagtt  6840
tacgcgttgc ttccgccagt ggcgcgaaat attcccgtgc accttgcgga cgggtatccg  6900
gttcgttggc aatactccac atcaccacgc ttgggtggtt tttgtcacgc gctatcagct  6960
ctttaatcgc ctgtaagtgc gcttggtgag tttccccgtt gactgcctct tcgttgtaca  7020
gttctttcgg cttgttgccc gcttcgaaac caatgcctaa agagaggtta aagccgacag  7080
cagcagtttc atcaatcacc acgatgccat gttcatctgc ccagtcgagc atctcttcag  7140
cgtaagggta atgcgaggta cggtaggagt tggccctaat ccagtccatt aatgcgtggt  7200
cgtgcaccat cagcacgtta tcgaatcctt tgccacgcaa gtccgcatct tcatgacgac  7260
caaagccagt aaagtagaac ggtttgtggt taatcaggaa ctgttcgccc ttcactgcca  7320
ctgaccggat gccgacgcga agcgggtaga tatcacactc tgtctggctt ttggctgtga  7380
cgcacagttc atagagataa ccttcacccg gttgccagag gtgcggattc ccacttgca   7440
aagtcccgct agtgccttgt ccagttgcaa ccacctgttg atccgcatca cgcagttcaa  7500
cgctgacatc accattggcc accacctgcc agtcaacaga cgcgtggtta cagtcttgcg  7560
cgacatgcgt cactacggtg atatcgtcca cccaggtgtt cggcgtggtg tagagcatta  7620
cgctgcgatg gattccggca tagttaaaga aatcatggaa gtaagattgc tttttcttgc  7680
cgttttcgtt ggtaatcacc attcccggcg ggatagtctg ccagttcagt tcgttgttca  7740
cacaaacggt gatacccctc gacggattaa agacttcaag cggtcaacta tgaagaagtg  7800
ttcgtcttcg tcccagtaag ctatgtctct agaatgtagc catccatcct tgtcaatcaa  7860
ggcgttggtc gcttccggat tgtttacata accggacata atcataggtc ctctgacaca  7920
taatacgcct ctctgattaa cgcccagcgt tttcccggta tccagatcca caaccttcgc  7980
ttcaaaaaat ggaacaactt taccgaccgc gcccggttta tcatccccct cgggtgtaat  8040
cagaatagct gatgtagtct cagtgagccc atatccttgt cgtatccctg gaagatggaa  8100
gcgttttgca accgcttccc cgacttcttt cgaaagaggt gcgccccag aagcaatttc   8160
gtgtaaatta gataaatcgt atttgtcaat cagagtgctt ttggcgaaga atgaaaatag  8220
ggttggtact agcaacgcac tttgaatttt gtaatcctga agggatcgta aaacagctc   8280
ttcttcaaat ctatacatta agacgactcg aaatctacat atcaaatatc cgagtgtagt  8340
aaacattcca aaaccgtgat ggaatggaac aacacttaaa atcgcagtat ccggaatgat  8400
ttgattgcca aaaataggat ctctggcatg cgagaatcta gcgcaggcag ttctatgcgg  8460
aagggccaca cccttaggta acccagtaga tccagaggaa ttgttttgtc acgatcaaag  8520
gactctggta caaaatcgta ttcattaaaa ccgggaggta gatgagatgt gacgaaggtg  8580
tacatcgact gaaatccctg gtaatccgtt ttagaatcca tgataataat tttctggatt  8640
attggtaatt ttttttgcac gttcaaaatt ttttgcaacc ccttttggga aacaaacact  8700
acggtaggct gcgaaatgtt catactgttg agcaattcac gttcattata aatgtcgttc  8760
gcgggcgcaa ctgcaactcc gataaataac gcgcccaaca ccggcataaa gaattggaaga 8820
gagttttcac tgcatacgac gattctgtga tttgtattca gcccatatcg tttcatagct  8880
```

```
tctgccaacc gaacggacat ttcgaagtat tccgcgtacg tgatgttcac ctcgatatgt   8940
gcatctgtaa aaggaattgt tccaggaacc agggcgtatc tcttcatagc cttatgcagt   9000
tgctctccag cggttccatt ctctagcttt gcttctcaat ttcttatttg cataatgaga   9060
aaaaaaggaa aattaatttt aacaccaatt cagtagttga ttgagcaaat gcgttgccaa   9120
aaaggatgct ttagagacag tgttctctgc acagataagg acaaacatca ttcagaggga   9180
gtacccagag ctgagactcc taagccagtg agtggcacag cattctaggg agaaatatgc   9240
ttgtcatcac cgaagcctga ttccgtagag ccacaccttg gtaagggcca atctgctcac   9300
acaggataga gagggcagga gccagggcag agcatataag gtgaggtagg atcagttgct   9360
cctcacattt gcttctgaca tagttgtgtt gggagcttgg atcgatccac catgggcttc   9420
aatacctga ttgactggaa cagctgtagc cctgaacagc agcgtgcgct gctgacgcgt    9480
ccggcgattt ccgcctctga cagtattacc cggacggtca gcgatattct ggataatgca   9540
aaaacgcgcg gtgacgatgc cctgcgtgaa tacagcgcta aatttgataa aacagaagtg   9600
acagcgctac gcgtcacccc tgaagagatc gccgccgccg gcgcgcgtct gagcgacgaa   9660
ttaaaacagg cgatgaccgc tgccgtcaaa aatattgaaa cgttccattc cgcgcagacg   9720
ctaccgcttg tagatgtgga aacccagcca ggcgtgcgtt gccagcaggt tacgcgtccc   9780
gtctcgtctg tcggtctgta tattcccggc ggctcggctc cgctcttctc aacggtgctg   9840
atgctggcga cgccggcgcg cattgcggga tgctagaagg tggttctgtg ctcgccgccg   9900
cccatcgctg atgaaatcct ctatgcgcg caactgtgtg gcgtgcagga attctttaac    9960
ctcggcggcg cgcaggcgat tgccgctctg gccttcggca gcgagtccgt accgaaagtg  10020
gataaaattt ttggccccgg caacgccttt gtaaccgaag ccaaacgtca ggtcagccag  10080
cgtctcgacg gcgcggctat cgatatgcca gccgagccgt ctgaagtact ggtgatcgca  10140
gacagcggcc caacaccgga tttcgtcgct tctgacctgc tctcccagac tgagcacggc  10200
ccggattccc aggtgatcct gctgacgcct gatgctgaca ttgcccgcaa ggtggcggag  10260
gcggtagaac gtcaactggc ggaactgccg cgcgcggaca ccgcctggca ggccctgagc  10320
gccagtcgtc tgattgtgac caaagattta gcgcagtgcg tcgccatctc taatcagtat  10380
gggccggaac acttaatcat ccagacgcgc aatgcgcgcg atttggtgga tgcgattacc  10440
agcgcaggct cggtatttct cggcgactgg tcgccggaat ccgccggtga ttacgcttcc  10500
ggaaccaacc atgttttacc gacctatggc catactgcta cctgttccag ccttgggtta  10560
gcggatttcc agaaacggat gaccgttcag gaactgtcga aagcgggctt ttccgctctg  10620
gcatcaacca ttgaaacatt ggcggggggca gaacgtctga ccgcccataa aaatgccgtg  10680
accctgcgcg taaacgccct caaggagcaa gcatgagcac tgaaaacact ctcagcgtcg  10740
ctgacttagc ccgtgaaaat gtccgcaacc tggagatcca gacatgataa gatacattga  10800
tgagtttgga caaaccacaa ctagaatgca gtgaaaaaaa tgctttattt gtgaaatttg  10860
tgatgctatt gctttatttg taaccattat aagctgcaat aaacaagtta acaacaacaa  10920
ttgcattcat tttatgtttc aggttcaggg ggaggtgtgg gaggtttttt aaagcaagta  10980
aaacctctac aaatgtggta tggctgatta tgatctctag ctcgacgggg cgcctggccg  11040
ctactaactc tctcctcct ccttttttcct gcaggctcaa ggcgcgcatg cccgacggcg   11100
aggatctcgt cgtgacccat ggcgatgcct gcttgccgaa tatcatggtg gaaaatggcc  11160
gcttttctgg attcatcgac tgtggccggc tgggtgtggc ggaccgctat caggacatag  11220
```

```
cgttggctac ccgtgatatt gctgaagagc ttggcggcga atgggctgac cgcttcctcg    11280
tgctttacgg tatcgccgct cccgattcgc agcgcatcgc cttctatcgc cttcttgacg    11340
agttcttctg agcgggactc tggggttcga atgaccgac  caagcgacgc ccaacctgcc    11400
atcacgagat ttcgattcca ccgccgcctt ctatgaaagg ttgggcttcg aatcgttttt    11460
ccgggacgcc ggctggatga tcctccagcg cggggatctc atgctggagt tcttcgccca    11520
ccccaacttg tttattgcag cttataatgg ttacaaataa agcaatagca tcacaaattt    11580
cacaaataaa gcattttttt cactgcattc tagttgtggt ttgtccaaac tcatcaatct    11640
atcttatcat gtctggatcg cggccggtct ctctctagcc ctaggtctag acttggcaga    11700
acatatccat cgcgtccgcc atccagca   gccgcacgcg cgcatctcg  ggcagcgttg    11760 ggtcctggcc acgggtgcgc atgatcgtgc tcctgtcgtt gaggacccgg ctaggctggc    11820
ggggttgcct tactggttag cagaatgaat caccgatacg cgagcgaacg tgaagcgact    11880
gctgctgcaa aacgtctgcg acctgagcaa caacatgaat ggtcttcggt ttccgtgttt    11940
cgtaaagtct ggaaacgcgg aagtcagcgc cctgcaccat tatgttccgg atctgcatcg    12000
caggatgctg ctggctaccc tgtggaacac ctacatctgt attaacgaag cgctggcatt    12060
gaccctgagt gattttttctc tggtcccgcc gcatccatac cgccagttgt ttaccctcac    12120
aacgttccag taaccgggca tgttcatcat cagtaacccg tatcgtgagc atcctctctc    12180
gtttcatcgg tatcattacc cccatgaaca gaaatccccc ttacacggag gcatcagtga    12240
ccaaacagga aaaaccgcc  cttaacatgg cccgctttat cagaagccag acattaacgc    12300
ttctggagaa actcaacgag ctggacgcgg atgaacaggc agacatctgt gaatcgcttc    12360
acgaccacgc tgatgagctt taccgcagct gcctcgcgcg tttcggtgat gacggtgaaa    12420
acctctgaca catgcagctc ccggagacgg tcacagcttg tctgtaagcg gatgccggga    12480
gcagacaagc ccgtcaggc  gcgtcagcgg gtgttggcgg gtgtcggggc gcagccatga    12540
cccagtcacg tagcgatagc ggagtgtata ctggcttaac tatgcggcat cagagcagat    12600
tgtactgaga gtgcaccata tgcggtgtga aataccgcac agatgcgtaa ggagaaaata    12660
ccgcatcagg cgctcttccg cttcctcgct cactgactcg ctgcgctcgg tcgttcggct    12720
gcggcgagcg gtatcagctc actcaaaggc ggtaatacgg ttatccacag aatcagggga    12780
taacgcagga aagaacatgt gagcaaaagg ccagcaaaag gccaggaacc gtaaaaaggc    12840
cgcgttgctg gcgtttttcc ataggctccg ccccccctgac gagcatcaca aaaatcgacg    12900
ctcaagtcag aggtggcgaa acccgacagg actataaaga taccaggcgt ttccccctgg    12960
aagctccctc gtgcgctctc ctgttccgac cctgccgctt accggatacc tgtccgcctt    13020
tctcccttcg ggaagcgtgg cgctttctca tagctcacgc tgtaggtatc tcagttcggt    13080
gtaggtcgtt cgctccaagc tgggctgtgt gcacgaaccc cccgttcagc ccgaccgctg    13140
cgccttatcc ggtaactatc gtcttgagtc aacccggta  agacacgact tatcgccact    13200
ggcagcagcc actggtaaca ggattagcag agcgaggtat gtaggcggtg ctacagagtt    13260
cttgaagtgg tggcctaact acggctacac tagaaggaca gtatttggta tctgcgctct    13320
gctgaagcca gttaccttcg gaaaagagt  tggtagctct tgatccggca acaaaccac     13380 cgctggtagc ggtggttttt ttgtttgcaa gcagcagatt acgcgcagaa aaaaaggatc    13440
tcaagaagat cctttgatct tttctacggg gtctgacgct cagtggaacg aaaactcacg    13500
ttaagggatt ttggtcatga gattatcaaa aaggatcttc acctagatcc ttttaaatta    13560
aaaatgaagt tttaaatcaa tctaaagtat atatgagtaa acttggtctg acagttacca    13620
```

-continued

```
atgcttaatc agtgaggcac ctatctcagc gatctgtcta tttcgttcat ccatagttgc   13680
ctgactcccc gtcgtgtaga taactacgat acgggagggc ttaccatctg gccccagtgc   13740
tgcaatgata ccgcgagacc cacgctcacc ggctccagat ttatcagcaa taaaccagcc   13800
agccggaagg gccgagcgca gaagtggtcc tgcaacttta ccgcctcca tccagtctat    13860 taattgttgc cggaagcta gagtaagtag ttcgccagtt aatagtttgc gcaacgttgt    13920
tgccattgct gcaggcatcg tggtgtcacg ctcgtcgttt ggtatggctt cattcagctc   13980
cggttcccaa cgatcaaggc gagttacatg atcccccatg ttgtgcaaaa aagcggttag   14040
ctccttcggt cctccgatcg ttgtcagaag taagttggcc gcagtgttat cactcatggt   14100
tatggcagca ctgcataatt ctcttactgt catgccatcc gtaagatgct tttctgtgac   14160
tggtgagtac tcaaccaagt cattctgaga atagtgtatg cggcgaccga gttgctcttg   14220
cccggcgtca acacgggata ataccgcgcc acatagcaga actttaaaag tgctcatcat   14280
tggaaaacgt tcttcggggc gaaaactctc aaggatctta ccgctgttga tccagttc    14340 gatgtaaccc actcgtgcac ccaactgatc ttcagcatct tttactttca ccagcgtttc   14400
tgggtgagca aaaacaggaa ggcaaaatgc cgcaaaaaag gaataagggc gacacggaa    14460 atgttgaata ctcatactct ccttttttca atattattga agcatttatc agggttattg   14520
tctcatgagc ggatacatat ttgaatgtat ttagaaaaat aaacaaatag gggttccgcg   14580
cacatttccc cgaaaagtgc cacctgacgt ctaagaaacc attattatca tgacattaac   14640
ctataaaaat aggcgtatca cgaggccctt tcgtcttcaa gaa                     14683
```

<210> SEQ ID NO 2
<211> LENGTH: 18986
<212> TYPE: DNA
<213> ORGANISM: Artificial Sequence
<220> FEATURE:
<223> OTHER INFORMATION: Description of Artificial Sequence: Synthetic
DNA referred to as "Molly"

<400> SEQUENCE: 2

```
ttaattaagg ggcggagaat gggcggaact gggcggagtt aggggcggga tgggcggagt    60
taggggcggg actatggttg ctgactaatt gagatgcatg ctttgcatac ttctgcctgc   120
tggggagcct ggggactttc cacacctggt tgctgactaa ttgagatgca tgctttgcat   180
acttctgcct gctggggagc ctggggactt ccacaccct aactgacaca cattccacag   240
aattaattcc cctagttatt aatagtaatc aattacgggg tcattaggtc atagcccata   300
tatggagttc cgcgttacat aacttacggt aaatggcccg cctggctgac cgcccaacga   360 ccccgccca ttgacgtcaa taatgacgta tgttcccata gtaacgccaa tagggacttt    420
ccattgacgt caatgggtgg actatttacg gtaaactgcc cacttggcag tacatcaagt   480
gtatcatatg ccaagtacgc ccctattga cgtcaatgac ggtaaatggc ccgcctggca    540
ttatgcccag tacatgacct tatgggactt tcctacttgg cagtacatct acgtattagt   600
catcgctatt accatggtga tgcggttttg gcagtacatc aatgggcgtg atagcggtt    660 tgactcacgg ggatttccaa gtctccaccc cattgacgtc aatgggagtt tgttttgaag   720 cttgccggc catataaacg gcggccagct ttatttaacg tgtttacgtc gagtcaattg    780
tacactaacg acagtgatga agaaatacac aaagcgcata atattttgaa cgacgtcgaa   840 ccttttattac aaaacaaaac acaaacgaat atcgacaaag ctagattgct gctacaagat   900
ttggcaagtt ttgtggcgtt gagcgaaaat ccattagata gtccagccat cggttcggaa   960
```

```
aaacaaccct tgtttgaaac taatcgaaac ctattttaca aatctattga ggatttaata    1020
tttaaattca gatataaaga cgctgaaaat catttgattt tcgctctaac ataccaccct    1080
aaagattata aatttaatga attattaaaa tacatcagca actatatatt gatagacatt    1140
tccagtttgt gatattagtt tgtgcgtctc attacaatgg ctgttatttt taacaacaaa    1200
caactgctcg cagacaatag tatagaaaag ggaggtgaac tgttttttgtt taacggttcg    1260 tacaacattt tggaaagtta tgttaatccg gtgctgctaa aaaatggtgt aattgaacta    1320
gaagaagctg cgtactatgc cggcaacata ttgtacaaaa ccgacgatcc caaattcatt    1380
gattatataa atttaataat taaagcaaca cactccgaag aactaccaga aaatagcact    1440
gttgtaaatt acagaaaaac tatgcgcagc ggtactatac accccattaa aaagacata     1500 tatatttatg acaacaaaaa atttactcta tacgatagat acatatatgg atacgataat    1560
aactatgtta attttatga ggagaaaaat gaaaagaga aggaatacga agaagaagac      1620
gacaaggcgt ctagtttatg tgaaaataaa attatattgt cgcaaattaa ctgtgaatca    1680
tttgaaaatg attttaaata ttacctcagc gattataact acgcgttttc aattatagat    1740
aatactacaa atgttcttgt tgcgtttggt ttgtatcgtt aataaaaaac aaatttagca    1800
tttataattg ttttattatt caataattac aaataggatt gagacccttg cagttgccag    1860
caaacggaca gagcttgtcg aggagagttg ttgattcatt gtttgcctcc ctgctgcggt    1920
ttttcaccga agttcatgcc agtccagcgt ttttgcagca gaaaagccgc cgacttcggt    1980
ttgcggtcgc gagtgaagat ccctttcttg ttaccgccaa cgcgcaatat gccttgcgag    2040
gtcgcaaaat cggcgaaatt ccatacctgt tcaccgacga cggcgctgac gcgatcaaag    2100
acgcggtgat acatatccag ccatgcacac tgatactctt cactccacat gtcggtgtac    2160
attgagtgca gcccggctaa cgtatccacg ccgtattcgg tgatgataat cggctgatgc    2220
agtttctcct gccaggccag aagttctttt tccagtacct tctctgccgt ttccaaatcg    2280
ccgctttgga cataccatcc gtaataacgg ttcaggcaca gcacatcaaa gagatcgctg    2340
atggtatcgg tgtgagcgtc gcagaacatt acattgacgc aggtgatcgg acgcgtcggg    2400
tcgagtttac gcgttgcttc cgccagtggc gcgaaatatt cccgtgcacc ttgcggacgg    2460
gtatccggtt cgttggcaat actccacatc accacgcttg ggtggttttt gtcacgcgct    2520
atcagctctt taatcgcctg taagtgcgct tgctgagttt ccccgttgac tgcctcttcg    2580
ctgtacagtt ctttcggctt gttgcccgct tcgaaaccaa tgcctaaaga gaggttaaag    2640
ccgacagcag cagtttcatc aatcaccacg atgccatgtt catctgccca gtcgagcatc    2700
tcttcagcgt aagggtaatg cgaggtacgg taggagttgg ccccaatcca gtccattaat    2760
gcgtggtcgt gcaccatcag cacgttatcg aatccttttgc cacgcaagtc cgcatcttca    2820
tgacgaccaa agccagtaaa gtagaacggt ttgtggttaa tcaggaactg ttcgcccttc    2880
actgccactg accggatgcc gacgcgaagc gggtagatat cacactctgt ctggcttttg    2940
gctgtgacgc acagttcata gagataacct tcacccggtt gccagaggtg cggattcacc    3000
acttgcaaag tcccgctagt gccttgtcca gttgcaacca cctgttgatc cgcatcacgc    3060
agttcaacgc tgcatcacc attggccacc acctgccagt caacgacgc gtggttacag     3120 tcttgcgcga catgcgtcac cacggtgata tcgtccaccc aggtgttcgg cgtggtgtag    3180
agcattacgc tgcgatggat tccggcatag ttaaagaaat catggaagta agactgcttt    3240
ttcttgccgt tttcgtcggt aatcaccatt cccggcggga tagtctgcca gttcagttcg    3300
```

```
ttgttcacac aaacggtgat acccctcgac ggattaaaga cttcaagcgg tcaactatga    3360
agaagtgttc gtcttcgtcc cagtaagcta tgtctccaga atgtagccat ccatccttgt    3420
caatcaaggc gttggtcgct tccggattgt ttacataacc ggacataatc ataggtcctc    3480
tgacacataa ttcgcctctc tgattaacgc ccagcgtttt cccggtatcc agatccacaa    3540
ccttcgcttc aaaaaatgga acaactttac cgaccgcgcc cggtttatca tcccctcgg    3600
gtgtaatcag aatagctgat gtagtctcag tgagcccata tccttgtcgt atccctggaa    3660
gatggaagcg ttttgcaacc gcttccccga cttctttcga agaggtgcg cccccagaag    3720
caatttcgtg taaattagat aaatcgtatt tgtcaatcag agtgcttttg gcgaagaatg    3780
aaaatagggt tggtactagc aacgcacttt gaattttgta atcctgaagg gatcgtaaaa    3840
acagctcttc ttcaaatcta tacattaaga cgactcgaaa tccacatatc aaatatccga    3900
gtgtagtaaa cattccaaaa ccgtgatgga atggaacaac acttaaaatc gcagtatccg    3960
gaatgatttg attgccaaaa ataggatctc tggcatgcga gaatctagcg caggcagttc    4020
tatgcggaag ggccacaccc ttaggtaacc cagtagatcc agaggaattg ttttgtcacg    4080
atcaaaggac tctggtacaa aatcgtattc attaaaaccg ggaggtagat gagatgtgac    4140
gaacgtgtac atcgactgaa atccctggta atccgtttta gaatccatga taataatttt    4200
ctggattatt ggtaattttt tttgcacgtt caaaatttt tgcaacccct ttttggaaac    4260
aaacactacg gtaggctgcg aaatgttcat actgttgagc aattcacgtt cattataaat    4320
gtcgttcgcg ggcgcaactg caactccgat aaataacgcg cccaacaccg gcataaagaa    4380
ttgaagagag ttttcactgc atacgacgat tctgtgattt gtattcagcc catatcgttt    4440
catagcttct gccaaccgaa cggacatttc gaagtattcc gcgtacgtga tgttcacctc    4500
gatatgtgca tctgtaaaag gaattgttcc aggaaccagg gcgtatctct tcatagcctt    4560
atgcagttgc tctccagcgg ttccatcctc tagctttgct tctcaatttc ttatttgcat    4620
aatgagaaaa aaaggaaaat taattttaac accaattcag tagttgattg agcaaatgcg    4680
ttgccaaaaa ggatgcttta gagacagtgt tctctgcaca gataaggaca aacattattc    4740
agagggagta cccagagctg agactcctaa gccagtgagt ggcacagcat tctagggaga    4800
aatatgcttg tcatcaccga agcctgattc cgtagagcca caccttggta agggccaatc    4860
tgctcacaca ggatagagag ggcaggagcc agggcagagc atataaggtg aggtaggatc    4920
agttgctcct cacatttgct tctgacatag ttgtgttggg agcttggatc gatccaccat    4980
gggcttcaat accctgattg actggaacag ctgtagccct gaacagcagc gtgcgctgct    5040
gacgcgtccg gcgatttccg cctctgacag tattacccgg acggtcagcg atattctgga    5100
taatgtaaaa acgcgcggtg acgatgccct gcgtgaatac agcgctaaat ttgataaaac    5160
agaagtgaca gcgctacgcg tcaccctga agagatcgcc gccgccggcg cgcgtctgag    5220
cgacgaatta aaacaggcga tgaccgctgc cgtcaaaaat attgaaacgt tccattccgc    5280
gcagacgcta ccgcctgtag atgtggaaac ccagccaggc gtgcgttgcc agcaggttac    5340
gcgtcccgtc tcgtctgtcg gtctgtatat tcccggcggc tcggctccgc tcttctcaac    5400
ggtgctgatg ctggcgacgc cggcgcgcat tgcgggatgc cagaaggtgg ttctgtgctc    5460
gccgccgccc atcgctgatg aaatcctcta tgcggcgcaa ctgtgtggcg tgcaggaaat    5520
ctttaacgtc ggcggcgcgc aggcgattgc cgctctggcc ttcggcagcg agtccgtacc    5580
gaaagtggat aaaattttg gccccggcaa cgcctttgta accgaagcca aacgtcaggt    5640
cagccagcgt ctcgacggcg cggctatcga tatgccagcc gggccgtctg aagtactggt    5700
```

```
gatcgcagac agcggcgcaa caccggattt cgtcgcttct gacctgctct cccaggctga   5760
gcacggcccg gattcccagg tgatcctgct gacgcctgat gctgacattg cccgcaaggt   5820
ggcggaggcg gtagaacgta aactggcgga actgccgcgc gcggacaccg cccggcaggc   5880
cctgagcgcc agtcgtctga ttgtgaccaa agatttagcg cagtgcgtcg ccatctctaa   5940
tcagtatggg ccggaacact taatcatcca gacgcgcaat gcgcgcgatt tggtggatgc   6000
gattaccagc gcaggctcgg tatttctcgg cgactggtcg ccggaatccg ccggtgatta   6060
cgcttccgga accaaccatg ttttaccgac ctatggctat actgctacct gttccagcct   6120
tgggttagcg gatttccaga aacggatgac cgttcaggaa ctgtcgaaag cgggcttttc   6180
cgctctggca tcaaccattg aaacattggc ggcggcagaa cgtctgaccg cccataaaaa   6240
tgccgtgacc ctgcgcgtaa acgccctcaa ggagcaagca tgagcactga aaacactctc   6300
agcgtcgctg acttagcccg tgaaaatgtc cgcaacctgg agatccagac atgataagat   6360
acattgatga gtttggacaa accacaacta gaatgcagtg aaaaaaatgc tttatttgtg   6420
aaatttgtga tgctattgct ttatttgtaa ccattataag ctgcaataaa caagttaaca   6480
acaacaattg cattcatttt atgtttcagg ttcaggggga ggtgtgggag gttttttaaa   6540
gcaagtaaaa cctctacaaa tgtggtatgg ctgattatga tctctagctc gacggcgcgc   6600
ctctagagca gtgtggtttt gcaagaggaa gcaaaaagcc tctccaccca ggcctggaat   6660
gtttccaccc aatgtcgagc agtgtggttt gcaagagga agcaaaaagc ctctccaccc   6720
aggcctggaa tgtttccacc caatgtcgag caaaccccgc ccagcgtctt gtcattggcg   6780
aattcgaaca cgcagatgca gtcggggcgg cgcggtccca gtcccacttc gcatattaag   6840
gtgacgcgtg tggcctcgaa caccgagcga ccctgcagcc aatatgggat cggccattga   6900
acaagatgga ttgcacgcag gttctccggc cgcttgggtg gagaggctat tcggctatga   6960
ctgggcacaa cagacaatcg gctgctctga tgccgccgtg ttccggctgt cagcgcaggg   7020
gcgcccggtt cttttttgtca agaccgacct gtccggtgcc ctgaatgaac tgcaggtaag   7080
tgcggccgtc gatggccgag gcggcctcgg cctctgcata aataaaaaaa attagtcagc   7140
catgcatggg gcggagaatg ggcggaactg ggcggagtta ggggcgggat gggcggagtt   7200
aggggcggga ctatggttgc tgactaattg agatgcatgc tttgcatact tctgcctgct   7260
ggggagcctg gggactttcc acacctggtt gctgactaat tgagatgcat gctttgcata   7320
cttctgcctg ctggggagcc tggggacttt ccacacccta actgacacac attccacaga   7380
attaattccc ctagttatta atagtaatca attacgggt cattagttca tagcccatat   7440
atggagttcc gcgttacata acttacggta aatggcccgc ctggctgacc gcccaacgac   7500
ccccgcccat tgacgtcaat aatgacgtat gttcccatag taacgccaat agggactttc   7560
cattgacgtc aatgggtgga ctatttacgg taaactgccc acttggcagt acatcaagtg   7620
tatcatatgc caagtacgcc ccctattgac gtcaatgacg gtaaatggcc cgcctggcat   7680
tatgcccagt acatgacctt atgggacttt cctacttggc agtacatcta gctattagtc   7740
atcgctatta ccatggtgat gcggttttgg cagtacatca atgggcgtgg atagcggttt   7800
gactcacggg gatttccaag tctccacccc attgacgtca atgggagttt gttttggcac   7860
caaaatcaac gggactttcc aaaatgtcgt aacaactccg ccccattgac gcaaatgggc   7920
ggtaggcgtg tacggtggga ggtctatata agcagagctg gtacgtgaa ccgtcagatc   7980 gcctggagac gccatcacag atctctcact atggattttc aggtgcagat tatcagcttc   8040
```

-continued

```
ctgctaatca gtgcttcagt cataatgtcc agaggacaaa ttgttctctc ccagtctcca    8100
gcaatcctgt ctgcatctcc aggggagaag gtcacaatga cttgcagggc cagctcaagt    8160
gtaagttaca tccactggtt ccagcagaag ccaggatcct cccccaaacc ctggatttat    8220
gccacatcca acctggcttc tggagtccct gttcgcttca gtggcagtgg gtctgggact    8280
tcttactctc tcacaatcag cagagtggag gctgaagatg ctgccactta ttactgccag    8340
cagtggacta gtaacccacc cacgttcgga gggggaccaa agctggaaat caaacgtacg    8400
gtggctgcac catctgtctt catcttcccg ccatctgatg agcagttgaa atctggaact    8460
gcctctgttg tgtgcctgct gaataacttc tatcccagag aggccaaagt acagtggaag    8520
gtggataacg ccctccaatc gggtaactcc caggagagtg tcacagagca ggacagcaag    8580
gacagcacct acagcctcag cagcaccctg acgctgagca agcagactac gagaaacac    8640 aaagtctacg cctgcgaagt cacccatcag ggcctgagct cgcccgtcac aaagagcttc    8700
aacaggggag agtgttgaat tcagatccgt taacggttac caactaccta gactggattc    8760
gtgacaacat gcggccgtga tatctacgta tgatcagcct cgactgtgcc ttctagttgc    8820
cagccatctg ttgtttgccc ctcccccgtg ccttccttga ccctggaagg tgccactccc    8880
actgtccttt cctaataaaa tgaggaaatt gcatcgcatt gtctgagtag gtgtcattct    8940
attctggggg gtggggtggg gcaggacagc aaggggagg attgggaaga caatagcagg    9000
catgctgggg atgcggtggg ctctatggaa ccagctgggg ctcgacagct atgccaagta    9060
cgccccctat tgacgtcaat gacggtaaat ggcccgcctg gcattatgcc cagtacatga    9120
ccttatggga ctttcctact tggcagtaca tctacgtatt agtcatcgct attaccatgg    9180
tgatgcggtt ttggcagtac atcaatgggc gtggatagcg gtttgactca cggggatttc    9240
caagtctcca ccccattgac gtcaatggga gtttgttttg gcaccaaaat caacgggact    9300
ttccaaaatg tcgtaacaac tccgccccat tgacgcaaat gggcggtagg cgtgtacggt    9360
gggaggtcta tataagcaga gctgggtacg tcctcacatt cagtgatcag cactgaacac    9420
agacccgtcg acatgggttg gagcctcatc ttgctcttcc ttgtcgctgt tgctacgcgt    9480
gtcctgtccc aggtacaact gcagcagcct ggggctgagc tggtgaagcc tggggcctca    9540
gtgaagatgt cctgcaaggc ttctggctac acatttacca gttacaatat gcactgggta    9600
aaacagacac ctggtcgggg cctggaatgg attggagcta tttatcccgg aaatggtgat    9660
acttcctaca atcagaagtt caaaggcaag gccacattga ctgcagacaa atcctccagc    9720
acagcctaca tgcagctcag cagcctgaca tctgaggact ctgcggtcta ttactgtgca    9780
agatcgactt actacggcgg tgactggtac ttcaatgtct ggggcgcagg gaccacggtc    9840
accgtctctg cagctagcac caaggcccca tcggtcttcc cctggcacc ctcctccaag    9900 agcacctctg ggggcacagc ggccctgggc tgcctggtca aggactactt ccccgaaccg    9960
gtgacggtgt cgtggaactc aggcgccctg accagcggcg tgcacacctt cccggctgtc    10020
ctacagtcct caggactcta ctccctcagc agcgtggtga ccgtgccctc cagcagcttg    10080
ggcacccaga cctacatctg caacgtgaat cacaagccca gcaacaccaa ggtggacaag    10140
aaagcagagc ccaaatcttg tgacaaaact cacacatgcc caccgtgccc agcacctgaa    10200
ctcctggggg gaccgtcagt cttcctcttc cccccaaaac ccaaggacac cctcatgatc    10260
tcccggaccc ctgaggtcac atgcgtggtg gtggacgtga gccacgaaga ccctgaggtc    10320
aagttcaact ggtacgtgga cggcgtggag gtgcataatg ccaagacaaa gccgcgggag    10380
gagcagtaca acagcacgta ccgtgtggtc agcgtcctca ccgtcctgca ccaggactgg    10440
```

```
ctgaatggca aggagtacaa gtgcaaggtc tccaacaaag ccctcccagc ccccatcgag   10500
aaaaccatct ccaaagccaa agggcagccc cgagaaccac aggtgtacac cctgccccca   10560
tcccgggatg agctgaccaa gaaccaggtc agcctgacct gcctggtcaa aggcttctat   10620
cccagcgaca tcgccgtgga gtgggagagc aatgggcagc cggagaacaa ctacaagacc   10680
acgcctcccg tgctggactc cgacggctcc ttcttcctct acagcaagct caccgtggac   10740
aagagcaggt ggcagcaggg gaacgtcttc tcatgctccg tgatgcatga ggctctgcac   10800
aaccactaca cgcagaagag cctctcgctg tctccgggta aatgaggatc cgttaacggt   10860
taccaactac ctagactgga ttcgtgacaa catgcggccg tgatatctac gtatgatcag   10920
cctcgactgt gccttctagt tgccagccat ctgttgtttg cccctccccc gtgccttcct   10980
tgaccctgga aggtgccact cccactgtcc tttcctaata aaatgaggaa attgcatcgc   11040
attgtctgag taggtgtcat tctattctgg gggtggggt ggggcaggac agcaaggggg   11100
aggattggga agacaatagc aggcatgctg gggatgcggt gggctctatg gaaccagctg   11160
gggctcgaca gcaacgctag gtcgaggccg ctactaactc tctcctcccct ccttttttcct   11220 gcaggacgag gcagcgcggc tatcgtggct ggccacgacg ggcgttcctt gcgcagctgt   11280
gctcgacgtt gtcactgaag cgggaaggga ctggctgcta ttgggcgaag tgccggggca   11340
ggatctcctg tcatctcacc ttgctcctgc cgagaaagta tccatcatgg ctgatgcaat   11400
gcggcggctg catacgcttg atccggctac ctgcccattc gaccaccaag cgaaacatcg   11460
catcgagcga gcacgtactc ggatggaagc cggtcttgtc gatcaggatg atctggacga   11520
agagcatcag gggctcgcgc cagccgaact gttcgccagg taagtgagct ccaattcaag   11580
cttcctaggg cggccagcta gtagctttgc ttctcaattt cttatttgca taatgagaaa   11640
aaaaggaaaa ttaattttaa caccaattca gtagttgatt gagcaaatgc gttgccaaaa   11700
aggatgcttt agagacagtg ttctctgcac agataaggac aaacattatt cagagggagt   11760
acccagagct gagactccta agccagtgag tggcacagca ttctagggag aaatatgctt   11820
gtcatcaccg aagcctgatt ccgtagagcc acaccttggt aagggccaat ctgctcacac   11880
aggatagaga gggcaggagc cagggcagag catataaggt gaggtaggat cagttgctcc   11940
tcacatttgc ttctgacata gttgtgttgg gagcttggat agcttggaca gctcagggct   12000
gcgatttcgc gccaaacttg acggcaatcc tagcgtgaag gctggtagga ttttatcccc   12060
gctgccatca tggttcgacc attgaactgc atcgtcgccg tgtcccaaaa tatggggatt   12120
ggcaagaacg gagacctacc ctggcctccg ctcaggaacg agttcaagta cttccaaaga   12180
atgaccacaa cctcttcagt ggaaggtaaa cagaatctgg tgattatggg taggaaaacc   12240
tggttctcca ttcctgagaa gaatcgacct ttaaaggaca gaattaatat agttctcagt   12300
agagaactca agaaccacc acgaggagct cattttcttg ccaaaagttt ggatgatgcc   12360
ttaagactta ttgaacaacc ggaattggca agtaaagtag acatggtttg gatagtcgga   12420
ggcagttctg tttaccagga agccatgaat caaccaggcc accttagact ctttgtgaca   12480
aggatcatgc aggaatttga aagtgacacg ttttcccag aaattgattt ggggaaatat   12540
aaacttctcc cagaatAccc aggcgtcctc tctgaggtcc aggaggaaaa aggcatcaag   12600
tataagtttg aagtctacga gaagaaagac taacaggaag atgctttcaa gttctctgct   12660
cccctcctaa agctatgcat ttttataaga ccatgggact tttgctggct ttagatcagc   12720
ctcgactgtg ccttctagtt gccagccatc tgttgtttgc ccctcccccg tgccttcctt   12780
```

```
gaccctggaa ggtgccactc ccactgtcct ttcctaataa aatgaggaaa ttgcatcgca    12840
ttgtctgagt aggtgtcatt ctattctggg gggtggggtg gggcaggaca gcaagggggga   12900 ggattgggaa gacaatagca ggcatgctgg ggatgcggtg ggctctatgg aaccagctgg    12960
ggctcgaagc ggccgcccat ttcgctggtg gtcagatgcg ggatggcgtg ggacgcggcg    13020
gggagcgtca cactgaggtt ttccgccaga cgccactgct gccaggcgct gatgtgcccg    13080
gcttctgacc atgcggtcgc gttcggttgc actacgcgta ctgtgagcca gagttgcccg    13140
gcgctctccg gctgcggtag ttcaggcagt tcaatcaact gtttaccttg tggaccgaca    13200
tccagaggca cttcaccgct tgccagcggc ttaccatcca gcgccaccat ccagtgcagg    13260
agctcgttat cgctatgacg gaacaggtat tcgctggtca cttcgatggt ttgcccggat    13320
aaacggaact ggaaaaactg ctgctggtgt tttgcttccg tcagcgctgg atgcggcgtg    13380
cggtcggcaa agaccagacc gttcatacag aactggcgat cgttcggcgt atcgccaaaa    13440
tcaccgccgt aagccgacca cgggttgccg ttttcatcat atttaatcag cgactgatcc    13500
acccagtccc agacgaagcc gccctgtaaa cggggatact gacgaaacgc ctgccagtat    13560
ttagcgaaac cgccaagact gttacccatc gctgggggcgt attcgcaaag gatcagcggg    13620
cgcgtctctc cgggtagcga aagccatttt ttgatggacc attcggacc agccgggaag    13680 ggctggtctt catccacgcg cgcgtacatc gggcaaataa tatcggtggc cgtggtgtcg    13740
gctccgccgc cttcatactg caccgggcgg gaaggatcga cagatttgat ccagcgatac    13800
agcgcgtcgt gattagcgcc gtggcctgat tcattcccca cgaccagat gatcacactc     13860 gggtgattac gatcgcgctg caccattcgc gttacgcgtt cgctcatcgc cggtagccag    13920
cgcggatcat cggtcagacg attcattggc accatgccgt gggtttcaat attggcttca    13980
tccaccacat acaggccgta gcggtcgcac agcgtgtacc acagcggatg gttcggataa    14040
tgccaacagc gcacgcgtt aaagttgttc tgcttcatca gcaggatatc ctgcaccatc     14100
gtctgctcat ccatgacctg accatgcaga ggatgatgct cgtgacggtt aacgcctcga    14160
atcagcaacg gcttgccgtt cagcagcagc agaccatttt caatccgcac ctcgcggaaa    14220
ccgacatcgc aggcttctgc ttcaatcagc gtgccgtcgg cggtgtgcag ttcaaccacc    14280
gcacgataga gattcgggat ttcggcgctc cacagtttcg ggttttcgac gttcagacgc    14340
agtgtgacgc gatcggcata accaccacgc tcatcgataa tttcaccgcc gaaaggcgcg    14400
gtgccgctgg cgacctgcgt ttcaccctgc cataaagaaa ctgttacccg taggtagtca    14460
cgcaactcgc cgcacatctg aacttcagcc tccagtacag cgcggctgaa atcatcatta    14520
aagcgagtgg caacatggaa atcgctgatt tgtgtagtcg gtttatgcag caacgagacg    14580
tcacggaaaa tgccgctcat cccgccacata tcctgatctt ccagataact gccgtcactc    14640
caacgcagca ccatcaccgc gaggcggttt tctccggcgc gtaaaaatgc gctcaggtca    14700
aattcagacg gcaaacgact gtcctggccg taaccgaccc acgccccgtt gcaccacaga    14760
tgaaacgccg agttaacgcc atcaaaaata ttcgcgtct ggccttcctg tagccagctt     14820
tcatcaacat taaatgtgag cgagtaacaa cccgtcggat tctccgtggg aacaaacggc    14880
ggattgaccg taatgggata ggttacgttg gtgtagatgg cgcatcgta accgtgcatc     14940 tgccagttg aggggacgac gacagtatcg gcctcaggaa gatcgcactc cagccagctt     15000
tccggcaccg cttctggtgc cggaaaccag gcaaagcgcc attcgccatt caggctgcgc    15060
aactgttggg aagggcgatc ggtgcgggcc tcttcgctat tacgccagct ggcgaaaggg    15120
ggatgtgctg caaggcgatt aagttgggta acgccagggt tttcccagtc acgacgttgt    15180
```

-continued

```
aaaacgactt aatccgtcga ggggctgcct cgaagcagac gaccttccgt tgtgcagcca    15240
gcggcgcctg cgccggtgcc cacaatcgtg cgcgaacaaa ctaaaccaga acaaattata    15300
ccggcggcac cgccgccacc accttctccc gtgcctaaca ttccagcgcc tccaccacca    15360
ccaccaccat cgatgtctga attgccgccc gctccaccaa tgccgacgga acctcaaccc    15420
gctgcacctt tagacgacag acaacaattg ttggaagcta ttagaaacga aaaaaatcgc    15480
actcgtctca gaccggtcaa accaaaaacg gcgcccgaaa ccagtacaat agttgaggtg    15540
ccgactgtgt tgcctaaaga gacatttgag cctaaaccgc cgtctgcatc accgccacca    15600
cctccgcctc cgcctccgcc gccagccccg cctgcgcctc caccgatggt agatttatca    15660
tcagctccac caccgccgcc attagtagat ttgccgtctg aaatgttacc accgcctgca    15720
ccatcgcttt ctaacgtgtt gtctgaatta aaatcgggca cagttagatt gaaacccgcc    15780
caaaaacgcc cgcaatcaga aataattcca aaaagctcaa ctacaaattt gatcgcggac    15840
gtgttagccg acacaattaa taggcgtcgt gtggctatgg caaaatcgtc ttcggaagca    15900
acttctaacg acgagggttg ggacgacgac gataatcggc ctaataaagc taacacgccc    15960
gatgttaaat atgtccaagc tactagtggt accgcttggc agaacatatc catcgcgtcc    16020
gccatctcca gcagccgcac gcggcgcatc tcgggcagcg ttgggtcctg gccacgggtg    16080
cgcatgatcg tgctcctgtc gttgaggacc cggctaggct ggcggggttg ccttactggt    16140
tagcagaatg aatcaccgat acgcgagcga acgtgaagcg actgctgctg caaaacgtct    16200
gcgacctgag caacaacatg aatggtcttc ggtttccgtg tttcgtaaag tctggaaacg    16260
cggaagtcag cgccctgcac cattatgttc cggatctgca tcgcaggatg ctgctggcta    16320
ccctgtggaa cacctacatc tgtattaacg aagcgctggc attgaccctg agtgattttt    16380
ctctggtccc gccgcatcca taccgccagt tgtttaccct cacaacgttc cagtaaccgg    16440
gcatgttcat catcagtaac ccgtatcgtg agcatcctct ctcgtttcat cggtatcatt    16500 accccccatga acagaaatcc cccttacacg gaggcatcag tgaccaaaca ggaaaaaacc    16560
gcccttaaca tggcccgctt tatcagaagc cagacattaa cgcttctgga gaaactcaac    16620
gagctggacg cggatgaaca ggcagacatc tgtgaatcgc ttcacgacca cgctgatgag    16680
ctttaccgca gctgcctcgc gcgtttcggt gatgacggtg aaaacctctg acacatgcag    16740
ctcccggaga cggtcacagc ttgtctgtaa gcggatgccg ggagcagaca gcccgtcag    16800 ggcgcgtcag cgggtgttgg cgggtgtcgg ggcgcagcca tgacccagtc acgtagcgat    16860
agcggagtgt atactggctt aactatgcgg catcagagca gattgtactg agagtgcacc    16920
atatgcggtg tgaaataccg cacagatgcg taaggagaaa ataccgcatc aggcgctctt    16980
ccgcttcctc gctcactgac tcgctgcgct cggtcgttcg gctgcggcga gcggtatcag    17040
ctcactcaaa ggcggtaata cggttatcca cagaatcagg ggataacgca ggaaagaaca    17100
tgtgagcaaa aggccagcaa aaggccagga accgtaaaaa ggccgcgttg ctggcgtttt    17160
tccataggct ccgcccccct gacgagcatc acaaaaatcg acgctcaagt cagaggtggc    17220
gaaacccgac aggactataa agataccagg cgtttccccc tggaagctcc ctcgtgcgct    17280
ctcctgttcc gaccctgccg cttaccggat acctgtccgc ctttctccct tcgggaagcg    17340
tggcgctttc tcatagctca cgctgtaggt atctcagttc ggtgtaggtc gttcgctcca    17400
agctgggctg tgtgcacgaa ccccccgttc agcccgaccg ctgcgcctta tccggtaact    17460
atcgtcttga gtccaacccg gtaagacacg acttatcgcc actggcagca gccactggta    17520
```

-continued

```
acaggattag cagagcgagg tatgtaggcg gtgctacaga gttcttgaag tggtggccta     17580
actacggcta cactagaagg acagtatttg gtatctgcgc tctgctgaag ccagttacct     17640
tcggaaaaag agttggtagc tcttgatccg gcaaacaaac caccgctggt agcggtggtt     17700
tttttgtttg caagcagcag attacgcgca gaaaaaagg atctcaagaa gatcctttga      17760
tcttttctac gggtctgac gctcagtgga acgaaaactc acgttaaggg attttggtca      17820
tgagattatc aaaaggatc ttcacctaga tccttttaaa ttaaaaatga agttttaaat      17880
caatctaaag tatatatgag taaacttggt ctgacagtta ccaatgctta atcagtgagg     17940
cacctatctc agcgatctgt ctatttcgtt catccatagt tgcctgactc cccgtcgtgt     18000
agataactac gatacgggag ggcttaccat ctggccccag tgctgcaatg ataccgcgag     18060
acccacgctc accggctcca gatttatcag caataaacca gccagccgga agggccgagc     18120
gcagaagtgg tcctgcaact ttatccgcct ccatccagtc tattaattgt tgccgggaag     18180
ctagagtaag tagttcgcca gttaatagtt tgcgcaacgt tgttgccatt gctgcaggca     18240
tcgtggtgtc acgctcgtcg tttggtatgg cttcattcag ctccggttcc caacgatcaa     18300
ggcgagttac atgatccccc atgttgtgca aaaaagcggt tagctccttc ggtcctccga     18360
tcgttgtcag aagtaagttg gccgcagtgt tatcactcat ggttatggca gcactgcata     18420
attctcttac tgtcatgcca tccgtaagat gcttttctgt gactggtgag tactcaacca     18480
agtcattctg agaatagtgt atgcggcgac cgagttgctc ttgcccggcg tcaacacggg     18540
ataataccgc gccacatagc agaactttaa aagtgctcat cattggaaaa cgttcttcgg     18600
ggcgaaaact ctcaaggatc ttaccgctgt tgagatccag ttcgatgtaa cccactcgtg     18660
cacccaactg atcttcagca tcttttactt tcaccagcgt ttctgggtga gcaaaaacag     18720
gaaggcaaaa tgccgcaaaa aagggaataa gggcgacacg gaaatgttga atactcatac     18780
tcttcctttt tcaatattat tgaagcattt atcagggtta ttgtctcatg agcggataca     18840
tatttgaatg tatttagaaa aataaacaaa tagggttcc gcgcacattt ccccgaaaag      18900
tgccacctga cgtctaagaa accattatta tcatgacatt aacctataaa aataggcgta     18960
tcacgaggcc ctttcgtctt caagaa                                          18986
```

<210> SEQ ID NO 3
<211> LENGTH: 19040
<212> TYPE: DNA
<213> ORGANISM: Artificial Sequence
<220> FEATURE:
<223> OTHER INFORMATION: Description of Artificial Sequence: Synthetic
      DNA referred to as "Mandy"

<400> SEQUENCE: 3

```
ttaattaagg ggcggagaat gggcggaact gggcggagtt aggggcggga tgggcggagt     60 tagggggcggg actatggttg ctgactaatt gagatgcatg cttttgcatac ttctgcctgc   120 tggggagcct ggggactttc cacacctggt tgctgactaa ttgagatgca tgctttgcat     180
acttctgcct gctggggagc ctggggactt ccacaccct aactgacaca cattccacag     240
aattaattcc cctagttatt aatagtaatc aattacgggg tcattagttc atagcccata     300
tatggagttc cgcgttacat aacttacggt aaatggcccg cctggctgac cgcccaacga     360 ccccccgccca ttgacgtcaa taatgacgta tgttcccata gtaacgccaa tagggacttt     420
ccattgacgt caatgggtgg agtatttacg gtaaactgcc cacttggcag tacatcaagt     480
gtatcatatg ccaagtacgc cccctattga cgtcaatgac ggtaaatggc ccgcctggca     540
```

```
ttatgcccag tacatgacct tatgggactt tcctacttgg cagtacatct acgtattagt    600
catcgctatt accatggtga tgcggttttg gcagtacatc aatgggcgtg gatagcggtt    660
tgactcacgg ggatttccaa gtctccaccc cattgacgtc aatgggagtt tgttttgaag    720
ctgtttaaac agcttggccg ccagctttta tttaacgtgt ttacgtcgag tcaattgtac    780
actaacgaca gtgatgaaag aaatacaaaa gcgcataata ttttgaacga cgtcgaacct    840
ttattacaaa acaaaacaca aacgaatatc gacaaagcta gattgctgct acaagatttg    900
gcaagttttg tggcgttgag cgaaaatcca ttagatagtc cagccatcgg ttcggaaaaa    960
caacccttgt ttgaaactaa tcgaaaccta ttttacaaat ctattgagga tttaatattt   1020
aaattcagat ataaagacgc tgaaaatcat ttgattttcg ctctaacata ccaccctaaa   1080
gattataaat ttaatgaatt attaaaatac atcagcaact atatattgat agacatttcc   1140
agtttgtgat attagtttgt gcgtctcatt acaatggctg ttatttttaa caacaaacaa   1200
ctgctcgcag acaatagtat agaaaaggga ggtgaactgt ttttgtttaa cggttcgtac   1260
aacattttgg aaagttatgt taatccggtg ctgctaaaaa atggtgtaat tgaactagaa   1320
gaagctgcgt actatgccgg caacatattg tacaaaaccg acgatcccaa attcattgat   1380
tatataaatt taataattaa agcaacacac tccgaagaac taccagaaaa tagcactgtt   1440
gtaaattaca gaaaaactat gcgcagcggt actatacacc ccattaaaaa agacatatat   1500
atttatgaca acaaaaaatt tactctatac gatagataca tatatggata cgataataac   1560
tatgttaatt tttatgagga gaaaaatgaa aagagaagg aatacgaaga agaagacgac   1620
aaggcgtcta gtttatgtga aaataaaatt atattgtcgc aaattaactg tgaatcattt   1680
gaaaatgatt ttaaatatta cctcagcgat tataactacg cgttttcaat tatagataat   1740
actacaaatg ttcttgttgc gtttggtttg tatcgttaat aaaaaacaaa tttgacattt   1800
ataattgttt tattattcaa taattacaaa taggattgag acccttgcag ttgccagcaa   1860
acggacagag cttgtcgagg agagttgttg attcattgtt tgcctccctg ctgcggtttt   1920
tcaccgaagt tcatgccagt ccagcgtttt tgcagcagaa aagccgccga cttcggtttg   1980
cggtcggcga gtgaagatcc ctttcttgtt accgccaacg cgcaatatgc cttgcgaggt   2040
cgcaaaatcg gcgaaattcc atacctgttc accgacgacg cgcctgacgc gatcaaagac   2100
gcggtgatac atatccagcc atgcacactg atactcttca ctccacatgt cggtgtacat   2160
tgagtgcagc ccggctaacg tatccacgcc gtattcggtg atgataatcg gctgatgcag   2220
tttctcctgc caggccagaa gttcttttc cagtaccttc tctgccgttt ccaaatcgcc   2280
gctttgggac ataccatccg taataacggt tcaggcacag cacatcaaag agatcgctga   2340
tggtatcggt gtgagcgtcg cagaacatta cattgacgca ggtgatcgga cgcgtcgggt   2400
cgagtttacg cgttgcttcc gccagtggcg cgaaatattc ccgtgcacct gcggacgggt   2460
tatccggttc gttggcaata ctccacatca ccacgcttgg gtggttttg tcacgcgcta   2520 tcagctcttt aatcgcctgt aagtgcgctt gctgagtttc cccgttgact gcctcttcgc   2580
tgtacagttc tttcggcttg ttgcccgctt cgaaccaat gcctaaagag aggttaaagc   2640
cgacagcagc agtttcatca atcaccacga tgccatgttc atctgcccag tcgagcatct   2700
cttcagcgta agggtaatgc gaggtacggt aggagttggc cccaatccag tccattaatg   2760
cgtggtcgtg caccatcagc acgttatcga atcctttgcc acgcaagtcc gcatcttcat   2820
gacgaccaaa gccagtaaag tagaacggtt tgtggtaat caggaactgt tcgcccttca   2880
ctgccactga ccggatgccg acgcgaagcg ggtagatatc acactctgtc tggcttttgg   2940
```

```
ctgtgacgca cagttcatag agataacctt cacccggttg ccagaggtgc ggattcacca    3000
cttgcaaagt cccgctagtg ccttgtccag ttgcaaccac ctgttgatcc gcatcacgca    3060
gttcaacgct gacatcacca ttggccacca cctgccagtc aacagacgcg tggttacagt    3120
cttgcgcgac atgcgtcacc acggtgatat cgtccaccca ggtgttcggc gtggtgtaga    3180
gcattacgct gcgatggatt ccggcatagt taaagaaatc atggaagtaa gactgctttt    3240
tcttgccgtt ttcgtcggta atcaccattc ccggcgggat agtctgccag ttcagttcgt    3300
tgttcacaca aacggtgata cccctcgacg gattaaagac ttcaagcggt caactatgaa    3360
gaagtgttcg tcttcgtccc agtaagctat gtctccagaa tgtagccatc catccttgtc    3420
aatcaaggcg ttggtcgctt ccggattgtt tacataaccg acataatca taggtcctct    3480
gacacataat tcgcctctct gattaacgcc cagcgttttc ccggtatcca gatccacaac    3540
cttcgcttca aaaatggaa caactttacc gaccgcgccc ggtttatcat cccctcggg    3600
tgtaatcaga atagctgatg tagtctcagt gagcccatat ccttgtcgta tccctggaag    3660
atggaagcgt tttgcaaccg cttccccgac ttctttcgaa agaggtgcgc cccagaagc    3720
aatttcgtgt aaattagata atcgtatt gtcaatcaga gtgcttttgg cgaagaatga    3780
aaataggggtt ggtactagca acgcactttg aattttgtaa tcctgaaggg atcgtaaaaa    3840
cagctcttct tcaaatctat acattaagac gactcgaaat ccacatatca aatatccgag    3900
tgtagtaaac attccaaaac cgtgatggaa tggaacaaca cttaaaatcg cagtatccgg    3960
aatgatttga ttgccaaaaa taggatctct ggcatgcgag aatctgacgc aggcagttct    4020
atgcggaagg gccacaccct taggtaaccc agtagatcca gaggaattgt tttgtcacga    4080
tcaaaggact ctggtacaaa atcgtattca ttaaaaccgg gaggtagatg agatgtgacg    4140
aacgtgtaca tcgactgaaa tccctggtaa tccgttttag aatccatgat aataattttc    4200
tggattattg gtaattttt ttgcacgttc aaaatttttt gcaacccctt tttgaaaaca    4260
aacactacgg taggctgcga aatgttcata ctgttgagca attcacgttc attataaatg    4320
tcgttcgcgg gcgcaactgc aactccgata ataacgcgc ccaacaccgg cataaagaat    4380
tgaagagagt tttcactgca tacgacgatt ctgtgatttg tattcagccc atatcgtttc    4440
atagcttctg ccaaccgaac ggacatttcg aagtattccg cgtacagccc ggccgtttaa    4500
acggccgggc ttcaataccc tgattgactg gaacagctgt agccctgaac agcagcgtgc    4560
gctgctgacg cgtccggcga tttccgcctc tgacagtatt acccggacgg tcagcgatat    4620
tctggataat gtaaaaacgc gcggtgacga tgccctgcgt gaatacagcg ctaaatttga    4680
taaaacagaa gtgacagcgc tacgcgtcac ccctgaagag atcgccgccg ccggcgcgcg    4740
tctgagcgac gaattaaaac aggcgatgac cgctgccgtc aaaaatattg aaacgttcca    4800
ttccgcgcag acgctaccgc ctgtagatgt ggaaacccag ccaggcgtgc gttgccagca    4860
ggttacgcgt cccgtctcgt ctgtcggtct gtatattccc ggcggctcgg ctccgctctt    4920
ctcaacggtg ctgatgctgg cgacgccggc gcgcattgcg ggatgccaga aggtggttct    4980
gtgctcgccg ccgcccatcg ctgatgaaat cctctatgcg gcgcaactgt gtggcgtgca    5040
ggaaatcttt aacgtcggcg gcgcgcaggc gatttgccgc tctggccttc ggcagcgagt    5100
ccgtaccgaa agtggataaa atttttggcc ccggcaacgc ctttgtaacc gaagccaaac    5160
gtcaggtcag ccagcgtctc gacgcgcgcg ctatcgatat gccagccggg cggtctgaag    5220
tactggtgat cgcagacagc ggcgcaacac cggatttcgt cgcttctgac ctgctcttcc    5280
```

-continued

```
caggctgagc acggcccgga ttcccaggtg atcctgctga cgcctgatgc tgacattgcc    5340
cgcaaggtgg cggaggcggt agaacgtcaa ctggcggaac tgccgcgcgc ggacaccgcc    5400
cggcaggccc tgagcgccag tcgtctgatt gtgaccaaag atttagcgca gtgcgtcgcc    5460
atctctaatc agtatgggcc ggaacactta atcatccaga cgcgcaatgc gcgcgatttg    5520
gtggatgcga ttaccagcgc aggctcggta tttctcggcg actggtcgcc ggaatccgcc    5580
ggtgattacg cttccggaac caaccatgtt ttaccgacct atggctatac tgctacctgt    5640
tccagccttg ggttagcgga tttccagaaa cggatgaccg ttcaggaact gtcgaaagcg    5700
ggcttttccg ctctggcatc aaccattgaa acattggcgg cggcagaacg tctgaccgcc    5760
cataaaaatg ccgtgaccct gcgcgtaaac gccctcaagg agcaagcatg agcactgaaa    5820
acactctcag cgtcgctgac ttagcccgtg aaaatgtccg caacctggag atccagacat    5880
ggataagata cattgatgag tttggacaaa ccacaactag aatgcagtga aaaaaatgct    5940
ttatttgtga aatttgtgat gctattgctt tatttgtaac cattataagc tgcaataaac    6000
aagttaacaa caacaattgc attcatttta tgtttcaggt tcaggggag gtgtgggagg    6060 ttttttaaag caagtaaaac ctctacaaat gtggtatggc tgattatgat ctctagggcc    6120
ggccctcgac ggcgcgtcta gagcagtgtg gttttcaaga ggaagcaaaa agcctctcca    6180
cccaggcctg gaatgtttcc acccaatgtc gagcagtgtg gttttgcaag aggaagcaaa    6240
aagcctctcc acccaggcct ggaatgtttc cacccaatgt cgagcaaacc ccgcccagcg    6300
tcttgtcatt ggcgaattgg aacacgcata tgcagtcggg gcggcgcggt cccaggtcca    6360
cttcgcatat taaggtggcg cgtgtggcct cgaacaccga gcgaccctgc agccaatatg    6420
ggatcggcca ttgaacaaga tggattgcac gcaggttctc cggccgcttg ggtggagagg    6480
ctattcggct atgactgggc acaacagaca atcggctgct ctgatgccgc cgtgttccgg    6540
ctgtcagcgc aggggcgccc ggttcttttt gtcaagaccg acctgtccgg tgccctgaat    6600
gaactgcagg taagtgcggc cgtcgatggc cgaggcggcc tcggcctctg cataaataaa    6660
aaaaattagt cagccatgca tggggcggag aatgggcgga actgggcgga gttaggggcg    6720
ggatgggcgg agttaggggc gggactatgg ttgctgacta attgagatgc atgctttgca    6780
tacttctgcc tgctggggag cctggggact ttccacacct ggttgctgac taattgagat    6840
gcatgctttg catacttctg cctgctgggg agcctgggga ctttccacac cctaactgac    6900
acacattcca cagaattaat tccctagtt attaatagta atcaattacg ggtcattag    6960 ttcatagccc atatatggag ttccgcgtta cataacttac ggtaaatggc ccgcctggct    7020
gaccgcccaa cgacccccgc ccattgacgt caataatgac gtatgttccc atagtaacgc    7080
caatagggac tttccattga cgtcaatggg tggagtattt acggtaaact gcccacttgg    7140
cagtacatca agtgtatcat atgccaagta cgccccctat tgacgtcaat gacggtaaat    7200
ggcccgcctg gcattatgcc cagtacatga cctcatggga ctttcctact tccagtaca    7260 tctacgtatt agtcatcgct attaccatgg tgatgcggtt ttggcagtac atcaatgggc    7320
gtggatagcg gtttgactca cggggatttc caagtctcca ccccattgac gtcaatggga    7380
gtttgttttg gcaccaaaat caacgggact ttccaaaatg tcgtaacaac tccgccccat    7440
tgacgcaaat gggcggtagg cgtgtacggt gggaggtcta tataagcaga gctgggtacg    7500
tgaaccgtca gatcgcctgg agacgccatc acagatctct caccatggac atgagggtcc    7560
ccgctcagct cctggggctc cttctgctct ggctcccagg tgccagatgt gacatccaga    7620
tgacccagtc tccatcttcc ctgtctgcat ctgtagggga cagagtcacc atcacttgca    7680
```

-continued

```
gggcaagtca ggacattagg tattatttaa attggtatca gcagaaacca ggaaaagctc    7740
ctaagctcct gatctatgtt gcatccagtt tgcaaagtgg ggtcccatca aggttcagcg    7800
gcagtggatc tgggacagag ttcactctca ccgtcagcag cctgcagcct gaagattttg    7860
cgacttatta ctgtctacag gtttatagta cccctcggac gttcggccaa gggaccaagg    7920
tggaaatcaa acgtacggtg gctgcaccat ctgtcttcat cttcccgcca tctgatgagc    7980
agttgaaatc tggaactgcc tctgttgtgt gcctgctgaa taacttctat cccagagagg    8040
ccaaagtaca gtggaaggtg gataacgccc tccaatcggg taactcccag gagagtgtca    8100
cagagcagga cagcaaggac agcacctaca gcctcagcag caccctgacg ctgagcaaag    8160
cagactacga gaaacacaaa gtctacgcct gcgaagtcac ccatcagggc ctgagctcgc    8220
ccgtcacaaa gagcttcaac aggggagagt gttgaattca gatccgttaa cggttaccaa    8280
ctacctagac tggattcgtg acaacatgcg gccgtgatat ctacgtatga tcagcctcga    8340
ctgtgccttc tagttgccag ccatctgttg tttgcccctc ccccgtgcct tccttgaccc    8400
tggaaggtgc cactcccact gtcctttcct aataaaatga ggaaattgca tcgcattgtc    8460
tgagtaggtg tcattctatt ctggggggtg ggtggggca ggacagcaag ggggaggatt    8520
gggaagacaa tagcaggcat gctggggatg cggtgggctc tatggcttct gaggcggaaa    8580
gaaccagctg ggactagtcg caattgggcg gagttagggg cgggatgggc ggagttaggg    8640
gcggggacta tggtgctgac taattgagat gcatgctttg catacttctg cctgctgggg    8700
agcctgggga cttttccacac ctggttgctg actaattgag atgcatgctt tgcatacttc    8760
tgcctgctgg ggagcctggg gactttccac accctaactg acacacattc cacagaatta    8820 attccctag ttattaatag taatcaatta cggggtcatt agttcatagc ccatatatgg    8880
agttccgcgt tacataactt acggtaaatg gcccgcctgg ctgaccgccc aacgaccccc    8940
gcccattgac gtcaataatg acgtatgttc ccatagtaac gccaatagg actttccatt    9000 gacgtcaatg ggtggagtat ttacggtaaa ctgcccactt ggcagtacat caagtgtatc    9060
atatgccaag tacgccccct attgacgtca atgacggtaa atggcccgcc tggcattatg    9120
cccagtacat gaccttatgg gactttccta cttggcagta catctacgta ttagtcatcg    9180
ctgttaccat ggtgatgcgg ttttggcagt acatcaatgg gcgtggatag cggtttgact    9240
cacggggatt tccaagtctc cacccccattg acgtcaatgg gagtttgttt tggcaccaaa    9300
atcaacggga ctttccaaaa tgtcgtaaca actccgcccc attgacgcaa atgggcggta    9360
ggcgtgtacg gtgggaggtc tatataagca gagctgggta cgtgaaccgt cagatcgcct    9420
ggagacgccg tcgacatggg ttggagcctc atcttgctct tccttgtcgc tgttgctacg    9480
cgtgtcctgt ccgaggtgca gctggtggag tctggggcg gcttggcaaa gcctgggggg    9540
tccctgagac tctcctgcgc agcctccggg ttcaggttca ccttcaataa ctactacatg    9600
gactgggtcc gccaggctcc agggcagggg ctggagtggg tctcacgtat tagtagtagt    9660
ggtgatccca catggtacgc agactccgtg aagggcagat tcaccatctc cagagagaac    9720
gccaagaaca cactgtttct tcaaatgaac agcctgagag ctgaggacac ggctgtctat    9780
tactgtgcga gcttgactac agggtctgac tccctgggc cagggagtcc tggtcaccgt    9840
ctcctcagct agcaccaagg gcccatcggt cttccccctg gcaccctcct ccaagagcac    9900
ctctgggggc acagcggccc tgggctgcct ggtcaaggac tacttccccg aaccggtgac    9960
ggtgtcgtgg aactcaggcg ccctgaccag cggcgtgcac accttcccgg ctgtcctaca   10020
```

-continued

```
gtcctcagga ctctactccc tcagcagcgt ggtgaccgtg ccctccagca gcttgggcac    10080
ccagacctac atctgcaacg tgaatcacaa gcccagcaac accaaggtgg acaagaaagt    10140
tgagcccaaa tcttgtgaca aaactcacac atgcccaccg tgcccagcac ctgaactcct    10200 gggggggaccg tcagtcttcc tcttccccccc aaaacccaag acaccctca tgatctcccg    10260 gaccccctgag gtcacatgcg tggtggtgga cgtgagccac gaagaccctg aggtcaagtt    10320
caactggtac gtggacggcg tggaggtgca taatgccaag acaaagccgc gggaggagca    10380
gtacaacagc acgtaccgtg tggtcagcgt cctcaccgtc ctgcaccagg actggctgaa    10440
tggcaaggag tacaagtgca aggtctccaa caaagccctc ccagccccca tcgagaaaac    10500
catctccaaa gccaaagggc agccccgaga accacaggtg tacaccctgc ccccatcccg    10560
ggatgagctg accaagaacc aggtcagcct gacctgcctg gtcaaaggct tctatcccag    10620
cgacatcgcc gtggagtggg agagcaatgg gcagccggag aacaactaca agaccacgcc    10680
tcccgtgctg gactccgacg gctccttctt cctctacagc aagctcaccg tggacaagag    10740
caggtggcag caggggaacg tcttctcatg ctccgtgatg catgaggctc tgcacaacca    10800
ctacacgcag aagagcctct ccctgtctcc gggtaaatga ggatccgtta acggttacca    10860
actacctaga ctggattcgt gacaacatgc ggccgtgata tctacgtatg atcagcctcg    10920
actgtgcctt ctagttgcca gccatctgtt gtttgccccc tcccccgtgc cttccttgac    10980
cctggaaggt gccactccca ctgtcctttc ctaataaaat gaggaaattg catcgcattg    11040
tctgagtagg tgtcattcta ttctgggggg tggggtgggg caggacagca agggggagga    11100
ttgggaagac aatagcaggc atgctgggga tgcggtgggc tctatggctt ctgaggcgga    11160
aagaaccagc tggggctcga cagcaacgct aggtcgaggc cgctactaac tctctcctcc    11220 ctccttttc ctgcaggacg aggcagcgcg gctatcgtgg ctggccacga cgggcgttcc    11280
ttgcgcagct gtgctcgacg ttgtcactga agcgggaagg gactggctgc tattgggcga    11340
agtgccgggg caggatctcc tgtcatctca ccttgctcct gccgagaaag tatccatcat    11400
ggctgatgca atgcggcggc tgcatacgct tgatccggct acctgcccat tcgaccacca    11460
agcgaaacat cgcatcgagc gagcacgtac tcggatggaa gccggtcttg tcgatcagga    11520
tgatctggac gaagagcatc agggctcgc gccagccgaa ctgttcgcca ggtaagtgag    11580
ctccaattca agctctcgag ctagggcggc cagctagtag ctttgcttct caatttctta    11640
tttgcataat gagaaaaaaa ggaaaattaa ttttaacacc aattcagtag ttgattgagc    11700
aaatgcgttg ccaaaaagga tgctttagag acagtgttct ctgcacagat aaggacaaac    11760
attattcaga gggagtaccc agagctgaga ctcctaagcc agtgagtggc acagcatcca    11820
gggagaaata tgcttgtcat caccgaagcc tgattccgta gagccacacc ctggtaaggg    11880
ccaatctgct cacacaggat agagagggca ggagccaggc agagcatata aggtgaggta    11940
ggatcagttg ctcctcacat ttgcttctga catagttgtg ttgggagctt ggatagcttg    12000 gggggggggac agctcaggge tgcgatttcg cgccaaactt gacggcaatc ctagcgtgaa    12060
ggctggtagg attttatccc cgctgccatc atggttcgac cattgaactg catcgtcgcc    12120
gtgtcccaaa atatggggat tggcaagaac ggagacctac cctggcctcc gctcaggaac    12180
gagttcaagt acttccaaag aatgaccaca acctcttcag tggaaggtaa acagaatctg    12240
gtgattatgg gtaggaaaac ctggttctcc attcctgaga agaatcgacc tttaaaggac    12300
agaattaata tagttctcag tagagaactc aaagaaccac cacgaggagc tcatttctt    12360 gccaaaagtt tggatgatgc cttaacgtag gcgcgccatt aagacttatt gaacaaccgg    12420
```

| | |
|---|---|
| aattggcaag taaagtagac atggtttgga tagtcggagg cagttctgtt taccaggaag | 12480 |
| ccatgaatca accaggcaac ctcagactct ttgtgacaag gatcatgcag gaatttgaaa | 12540 |
| gtgacacgtt tttcccagaa attgatttgg ggaaatataa acttctccca gaatacccag | 12600 |
| gcgtcctctc tgaggtcaag gaggaaaaag gcatcaagta taagtttgaa gtctacgaga | 12660 |
| agaaagacta acaggaagat gctttcaagt tctctgctcc cctcctaaag ctatgcattt | 12720 |
| ttataagacc atgggacttt tgctggcttt agatcagcct cgactgtgcc ttctagttgc | 12780 |
| cagccatctt ttgtttgccc ctcccccgtg ccttccttga ccctggaagg tgccactccc | 12840 |
| actgtccttt cctaataaaa tgaggaaatt gcatcgcatt gtctgagtag gtgtcattct | 12900 |
| attctggggg gtggggtggg gcaggacagc aaggggagg attgggaaga caatagcagg | 12960 |
| catgctgggg atgcggtggg ctctatggct tctgaggcgg aaagaaccag ctgggctcg | 13020 |
| aagcggccgc ccatttcgct ggtggtcaga tgcgggatgg cgtgggacgc ggcggggagc | 13080 |
| gtcacactga ggttttccgc cagacgccac tgctgccagg cgctgatgtg cccggcttct | 13140 |
| gaccatgcgg tcgcgttcgg ttgcactacg cgtactgtga gccagagttg cccggcgctc | 13200 |
| tccggctgcg gtagttcagg cagttcaatc aactgtttac cttgtggagc gacatccaga | 13260 |
| ggcacttcac cgcttgccag cggcttacca tccagcgcca ccatccagtg caggagctcg | 13320 |
| ttatcgctat gacggaacag gtattcgctg gtcacttcga tggtttgccc ggataaacgg | 13380 |
| aactggaaaa actgctgctg gtgttttgct tccgtcagcg ctggatgcgg cgtgcggtcg | 13440 |
| gcaaagacca gaccgttcat acagaactgg cgatccgttc ggctatcgcc aaaatcaccg | 13500 |
| ccgtaagccg accacggggtt gccgttttca tcatatttaa tcagcgactg atccacccag | 13560 |
| tcccagacga agccgccctg taaacgggga tactgacgaa acgcctgcca gtatttagcg | 13620 |
| aaaccgccaa gactgttacc catcgcgtgg gcgtattcgc aaaggatcag cgggcgcgtc | 13680 |
| tctccaggta gcgaaagcca ttttttgatg gaccatttcg gcacagccgg gaagggctgg | 13740 |
| tcttcatcca cgcgcgcgta catcgggcaa ataatatcgg tggccgtggt gtcggctccg | 13800 |
| ccgccttcat actgcaccgg gcgggaagga tcgacagatt tgatccagcg atacagcgcg | 13860 |
| tcgtgattag cgccgtggcc tgattcattc cccagcgacc agatgatcac actcgggtga | 13920 |
| ttacgatcgc gctgcaccat tcgcgttacg cgttcgctca tcgccggtag ccagcgcgga | 13980 |
| tcatcggtca gacgattcat tggcaccatg ccgtgggttt caatattggc ttcatccacc | 14040 |
| acatacaggc cgtagcggtc gcacagcgtg taccacagcg gatggttcgg ataatgcgaa | 14100 |
| cagcgcacgg cgttaaagtt gttctgcttc atcagcagga tatcctgcac catcgtctgc | 14160 |
| tcatccatga cctgaccatg cagaggatga tgctcgtgac ggttaacgcc tcgaatcagc | 14220 |
| aacggcttgc cgttcagcag cagcagacca ttttcaatcc gcacctcgcg gaaaccgaca | 14280 |
| tcgcaggctt ctgcttcaat cagcgtgccg tcggcggtgt gcagttcaac caccgcacga | 14340 |
| tagagattcg ggatttcggc gctccacagt ttcgggtttt cgacgttcag acgtagtgtg | 14400 |
| acgcgatcgg cataaccacc acgctcatcg ataatttcac cgccgaaagg cgcggtgccg | 14460 |
| ctggcgacct gcgtttcacc ctgccataaa gaaactgtta cccgtaggta gtcacgcaac | 14520 |
| tcgccgcaca tctgaacttc agcctccagt acagcgcggc tgaaatcatc attaaagcga | 14580 |
| gtggcaacat ggaaatcgct gatttgtgta gtcggtttat gcagcaacga gacgtcacgg | 14640 |
| aaaatgccgc tcatccgcca catatcctga tcttccagat aactgccgtc actccagcgc | 14700 |
| agcaccatca ccgcgaggcg gttttctccg gcgcgtaaaa atgcgctcag gtcaaattca | 14760 |

```
gacggcaaac gactgtcctg gccgtaaccg acccagcgcc cgttgcacca cagatgaaac    14820
gccgagttaa cgccatcaaa aataattcgc gtctggcctt cctgtagcca gctttcatca    14880
acattaaatg tgagcgagta acaacccgtc ggattctccg tgggaacaaa cggcggattg    14940
accgtaatgg gataggtcac gttggtgtag atgggcgcat cgtaaccgtg catctgccag    15000
tttgagggga cgacgacagt atcggcctca ggaagatcgc actccagcca gctttccggc    15060
accgcttctg gtgccggaaa ccagggcaag cgccattcgc cattcaggct gcgcaactgt    15120
tgggaagggc gatcggtgcg ggcctcttcg ctattacgcc agctggcgaa aggggatgt    15180 gctgcaaggc gattaagttg ggtaacgcca gggttttccc agtcacgacg ttgtaaaacg    15240
acttaatccg tcgaggggct gcctcgaagc agacgacctt ccgttgtgca gccagcggcg    15300
cctgcgccgg tgcccacaat cgtgcgcgaa caaactaaac cagaacaaat tataccggcg    15360
gcaccgccgc caccaccttc tcccgtgcct aacattccag cgcctccacc accaccacca    15420
ccatcgatgt ctgaattgcc gccgctcca ccaatgccga cggaacctca acccgctgca    15480
cctttagacg acagacaaca attgttggaa gctattagaa acgaaaaaaa tcgcactcgt    15540
ctcagaccgg tcaaaccaaa aacggcgccc gaaaccagta caatagttga ggtgccgact    15600
gtgttgccta aagagacatt tgagcctaaa ccgccgtctg catcaccgcc accacctccg    15660
cctccgcctc cgccgccagc cccgcctgcg cctccaccga tggtagattt atcatcagct    15720
ccaccaccgc cgccattagt agatttgccg tctgaaatgt taccaccgcc tgcaccatcg    15780
ctttctaacg tgttgtctga attaaaatcg ggcacagtta gattgaaacc cgcccaaaaa    15840
cgcccgcaat cagaaataat tccaaaaagc tcaactacaa atttgatcgc ggacgtgtta    15900
gccgacacaa ttaataggcg tcgtgtggct atggcaaaat cgtcttcgga agcaacttct    15960
aacgacgagg gttgggacga cgacgataat cggcctaata aagctaacac gcccgatgtt    16020
aaatatgtcc aagctactag tggtaccgct tggcagaaca tatccatcgc gtccgccatc    16080
tccagcagcc gcacgcggcg catctcgggc agcgttgggt cctggccacg ggtgcgcatg    16140
atcgtgctcc tgtcgttgag gacccggcta ggctggcggg gttgccttac tggttagcag    16200
aatgaatcac cgatacgcga gcgaacgtga agcgactgct gctgcaaaac gtctgcgacc    16260
tgagcaacaa catgaatggt cttcggtttc cgtgtttcgt aaagtctgga acgcggaag    16320 tcagcgccct gcaccattat gttccggatc tgcatcgcag gatgctgctg gctaccctgt    16380
ggaacaccta catctgtatt aacgaagcgc tggcattgac cctgagtgat ttttctctgg    16440
tcccgccgca tccataccgc cagttgttta ccctcacaac gttccagtaa ccgggcatgt    16500
tcatcatcag taacccgtat cgtgagcatc ctctctcgtt tcatcggtat cattaccccc    16560
atgaacagaa atcccccta cacggaggca tcagtgacca acaggaaaa aaccgccctt    16620 aacatggccc gctttatcag aagccagaca ttaacgcttc tggagaaact caacgagctg    16680
gacgcggatg aacaggcaga catctgtgaa tcgcttcacg accacgctga tgagctttac    16740
cgcagctgcc tcgcgcgttt cggtgatgac ggtgaaaacc tctgacacat gcagctcccg    16800
gagacggtca cagcttgtct gtaagcggat gccgggagca gacaagcccg tcagggcgcg    16860
tcagcgggtg ttggcgggtg tcggggcgca gccatgaccc agtcacgtag cgatagcgga    16920
gtgtatactg gcttaactat gcggcatcag agcagattgt actgagagtg caccatatgc    16980
ggtgtgaaat accgcacaga tgcgtaagga gaaataccg catcaggcgc tcttccgctt    17040
cctcgctcac tgactcgctg cgctcggtcg ttcggctgcg gcgagcggta tcagctcact    17100
caaaggcggt aatacggtta tccacagaat caggggataa cgcaggaaag aacatgtgag    17160
```

-continued

```
caaaaggcca gcaaaaggcc aggaaccgta aaaaggccgc gttgctggcg ttttcccata    17220
ggctccgccc ccctgacgag catcacaaaa atcgacgctc aagtcagagg tggcgaaacc    17280
cgacaggact ataaagatac caggcgtttc cccctggaag ctccctcgtg cgctctcctg    17340
ttccgaccct gccgcttacc ggatacctgt ccgcctttct cccttcggga agcgtggcgc    17400
tttctcatag ctcacgctgt aggtatctca gttcggtgta ggtcgttcgc tccaagctgg    17460
gctgtgtgca cgaaccccc gttcagcccg accgctgcgc cttatccggt aactatcgtc     17520
ttgagtccaa cccggtaaga cacgacttat cgccactggc agcagccact ggtaacagga    17580
ttagcagagc gaggtatgta ggcggtgcta cagagttctt gaagtggtgg cctaactacg    17640
gctacactag aaggacagta tttggtatct gcgctctgct gaagccagtt accttcggaa    17700
aaagagttgg tagctcttga tccggcaaac aaaccaccgc tggtagcggt ggtttttttg    17760
tttgcaagca gcagattacg cgcagaaaaa aaggatctca agaagatcct ttgatctttt    17820
ctacggggtc tgacgctcag tggaacgaaa actcacgtta agggattttg gtcatgagat    17880
tatcaaaaag gatcttcacc tagatccttt taaattaaaa atgaagtttt aaatcaatct    17940
aaagtatata tgagtaaact tggtctgaca gttaccaatg cttaatcagt gaggcaccta    18000
tctcagcgat ctgtctattt cgttcatcca tagttgcctg actccccgtc gtgtagataa    18060
ctacgatacg ggagggctta ccatctggcc ccagtgctgc aatgataccg cgagacccac    18120
gctcaccggc tccagattta tcagcaataa accagccagc cggaagggcc gagcgcagaa    18180
gtggtcctgc aactttatcc gcctccatcc agtctattaa ttgttgccgg gaagctagag    18240
taagtagttc gccagttaat agtttgcgca acgttgttgc cattgctgca ggcatcgtgg    18300
tgtcacgctc gtcgtttggt atggcttcat tcagctccgg ttcccaacga tcaaggcgag    18360
ttacatgatc ccccatgttg tgcaaaaaag cggttagctc cttcggtcct ccgatcgttg    18420
tcagaagtaa gttggccgca gtgttatcac tcatggttat ggcagcactg cataattctc    18480
ttactgtcat gccatccgta agatgctttt ctgtgactgg tgagtactca accaagtcat    18540
tctgagaata gtgtatgcgg cgaccgagtt gctcttgccc ggcgtcaaca cgggataata    18600
ccgcgccaca tagcagaact ttaaaagtgc tcatcattgg aaaacgttct cgggcgaa     18660 aactctcaag gatcttaccg ctgttgagat ccagttcgat gtaacccact cgtgcaccca    18720
actgatcttc agcatctttt actttcacca gcgtttctgg gtgagcaaaa acaggaaggc    18780
aaaatgccgc aaaaaaggga ataagggcga cacggaaatg ttgaatactc atactcttcc    18840 ttttcaata ttattgaagc atttatcagg gttattgtct catgagcgga tacatatttg     18900
aatgtattta gaaaaataaa caatagggg ttccgcgcac atttccccga aaagtgccac     18960
ctgacgtcta agaaaccatt attatcatga cattaaccta taaaaatagg cgtatcacga    19020
ggccctttcg tcttcaagaa                                                19040
```